(12) United States Patent
Paulus

(10) Patent No.: US 7,553,832 B2
(45) Date of Patent: Jun. 30, 2009

(54) METHODS AND COMPOSITIONS FOR SPECIFIC INHIBITION OF PROTEIN SPLICING BY SMALL MOLECULES

(75) Inventor: Henry Paulus, Boston, MA (US)

(73) Assignee: Boston Biomedical Research Institute, Watertown, MA (US)

( * ) Notice: Subject to any disclaimer, the term of this patent is extended or adjusted under 35 U.S.C. 154(b) by 310 days.

(21) Appl. No.: 11/338,383

(22) Filed: Jan. 24, 2006

(65) Prior Publication Data

US 2006/0217381 A1 Sep. 28, 2006

Related U.S. Application Data

(60) Provisional application No. 60/646,456, filed on Jan. 24, 2005.

(51) Int. Cl.
*A61K 31/33* (2006.01)
*C07K 2/00* (2006.01)
*C07K 14/00* (2006.01)

(52) U.S. Cl. .................. 514/183; 530/300; 530/344; 530/350; 530/412; 435/69.1; 435/69.2; 435/69.7; 435/71.1; 435/71.3

(58) Field of Classification Search .............. None
See application file for complete search history.

(56) References Cited

U.S. PATENT DOCUMENTS

| | | | |
|---|---|---|---|
| 5,496,714 | A | 3/1996 | Comb et al. |
| 5,795,731 | A | 8/1998 | Belfort |
| 5,834,247 | A | 11/1998 | Comb et al. |
| 6,521,425 | B2 | 2/2003 | Perler et al. |
| 2004/0137511 | A1 | 7/2004 | Masson et al. |
| 2004/0166561 | A1 | 8/2004 | Poulter et al. |

OTHER PUBLICATIONS http://medical-dictionary.thefreedictionary.com/Small+molecule.*
http://www.allwords.com/word-small+molecule+drug.html.*
http://www.astrazeneca-annualreports.com/2007/additional_information/glossary/n-t.asp.*
http://en.wikipedia.org/wiki/Small_molecule.*
Klabunde et al. "Crystal structure of GyrA intein from *Mycobacterium xenopi* reveals structural basis of protien splicing." Nat. Struct. Biol., 1998, 5, 31-6.*
Perler "Protein Splicing of Inteins and Hedgehog Autoproteolysis: Structure, Function and Evolution," Cell, 1998, 92, 1-4.*
Wickelgran "Spinning Junk into Gold" Science, 2003, 300, 1646-9.*
Perler & Adam "Protein Splicing and its Applications," Curr. Op. Biotech., 2000, 11, 377-83.*
Cantor et al., "Intein-mediated Rapid Purification of Cre Recombinase," Prot. Express. Purif., 2001, 22, 135-40.*
Wu et al., "Intein-mediated purification of cytotoxic endonuclease I-TevI by insertional inactivation and pH-controllable splicing," Nucleic Acids Res., 2002, 30, 4864-71.*
Chin et al., "Protein trans-splicing in transgenic plant chloroplast: Reconstruction of herbicide resistance from split genes," Proc. Natl. Acad. Sci. USA, 2003, 100, 4510-5.*
Muir et al., "Expressed protein ligation: A general method for protein engineering," Proc. Natl. Acad. Sci., 1998, 95, 6705-10.*
Mootz et al., "Conditional protein splicing: a new tool to control protein structure and function in vitro and in vivo.," J. Am. Chem. Soc., 2003, 125, 10561-9.*
Skretas & Wood, "Regulation of protein activity with small molecule-controlled inteins," Protein Sci., 2005, 14, 523-32.*
Brenzel & Mootz, "Design of an intein that can be inhibited with a small molecule ligand," J. Am. Chem. Soc., 2005, 127, 4176-7.*
Mills, K.V., & Paulus, H., Reversible Inhibition of Protein Splicing by Zinc Ion, J. Biol. Chem. 276, 10832-10838 (Apr. 2001).
Ghosh et al., Zinc Inhibition of Protein trans-Splicing and Identification of Regions Essential for Splicing and Association of a Split Intein, J. Biol. Chem. 276: 24051-24058 (Jun. 2001).
Mills, K.V., et al., Protein splicing in trans by purified N- and C-terminal fragments of the *Mycobacterium tuberculosis* RecA intein, Proc. Natl. Acad. Sci. USA 95: 3453-3458 (Mar. 1998).
Chong et al., Modulation of Protein Splicing of the *Saccharomyces cerevisiae* Vacuolar Membrane ATPase Intein, J. Biol. Chem. 273: 10567-10577 (Apr. 1998).
Pietrokovsky, S., Modular organization of inteins and C-terminal autocatalytic domains, Protein Science 7: 64-71 (Jan. 1998).
Gangopadhyay et al., An in Vitro Screening System for Protein Splicing Inhibitors Based on Green Fluorescent Protein as an Indicator, Anal. Chem. 75(10): 2456-2462 (May 2003).
Crameri et al., Improved Green Fluorescent Protein by Molecular Evolution Using DNA Shuffling, Nature Biotech. 14(3): 315-319 (Mar. 1996).
T. Ozawa et al., A fluorescent indicator for detecting protein-protein interactions in vivo based on protein splicing, Anal. Chem. 72: 5151-5157 (Nov. 2000)).
Niwa et al., Chemical Nature of the Light Emitter of the Aequorea Green Fluorescent Protein, Proc. Natl. Acad. Sci. USA 93: 13617-13622 (Nov. 1996).

* cited by examiner

*Primary Examiner*—Cecilia Tsang
*Assistant Examiner*—Christina Marchetti Bradley
(74) *Attorney, Agent, or Firm*—Pierce Atwood LLP; Kevin M. Farrell; David J. Wilson

(57) ABSTRACT

The present invention relates to compositions (i.e., various organic small molecules as exemplified herein) and methods for the inhibition of protein splicing and especially relates to the inhibition of protein autosplicing of intein-containing proteins. Additionally, the present invention relates to the use of the inhibitors of protein splicing of the invention for the treatment of various diseases including but not limited to tuberculosis. Furthermore, the invention provides the first instance of small molecule inhibitors of protein splicing with drug-like characteristics.

21 Claims, 20 Drawing Sheets

Figure 2

```
         N1
 1  C L T A S T R I L R A D T G A E V A F G E L M R S G E R P M    Mtu DnaB
 1  C L A E G T R I F D P V T G T T H R I E D V D G R K P I H      Mtu RecA
                              N2

31  V W S L D E R L R M V A R P M I N V F P S G R K E V F R L R    Mtu DnaB
31  V V A A K D G T L H A R P V S W F E D Q G T R D V I G L R      Mtu RecA
                          N3                              N4

61  L A S G R E V E A T G S H P F M K F E G W T P L A Q L K V G    Mtu DnaB
61  I A G G A I V W A T P D H K V L T E Y G W R A A G E L R K G    Mtu RecA

91  D R I A A P - - - - -                                          Mtu DnaB
91  D R V A Q P - - - - -                                          Mtu RecA

Homing endonuclease domain (not shown)

379 - - - D A Y W D T V V E I T S I G D D Q H V F D G T V S G T H  Mtu DnaB
404 - - - E L R Y S V I R E V L P T R R A R T F D L E V E E L H    Mtu RecA
                          C1                    C2

406 N F V A N G I S L H N                                          Mtu DnaB
430 T L V A E G V V H N                                            Mtu RecA
```

Figure 2

Compound #3

1,2,3-tri(methylsulfonyl)-
5-(trifluoromethyl)benzene

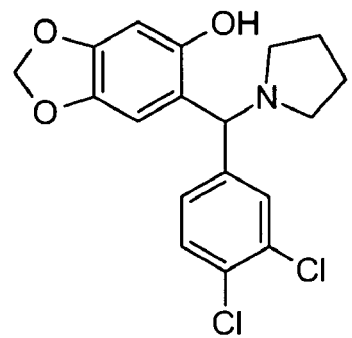
Formula 11 (Compound #1)
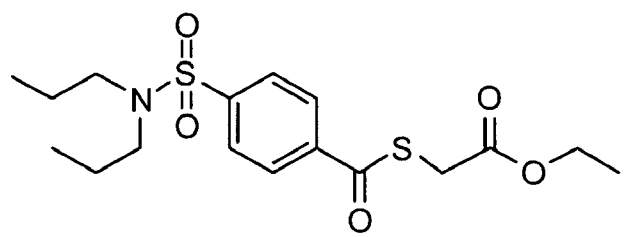
Formula 12 (Compound#2)
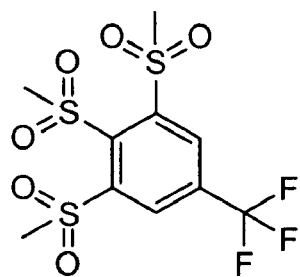
Formula 13 (Compound #3)
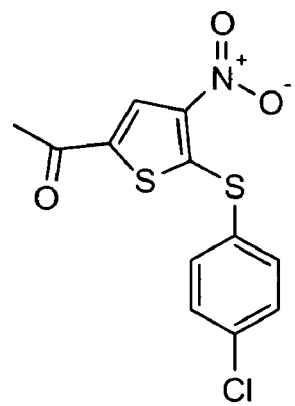
Formula 14 (Compound #4)
Figure 8A

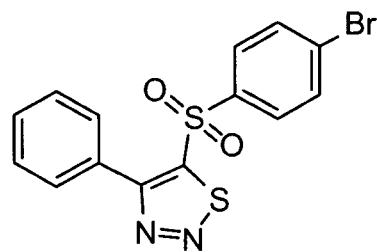
Formula 15 (Compound #6)
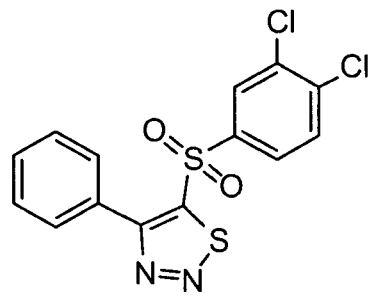
Formula 16 (Compound #7)
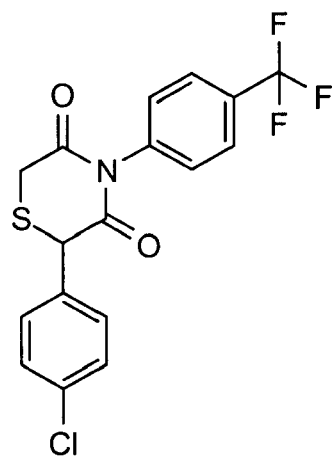
Formula 17 (Compound #8)
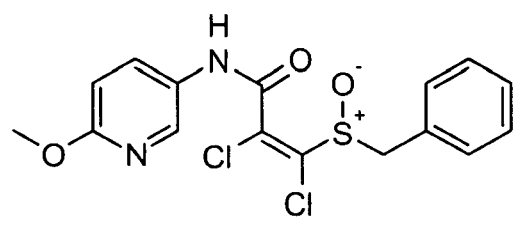
Formula 18 (Compound #9)
Figure 8B

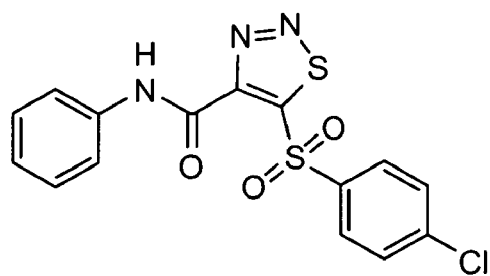
Formula 19 (Compound #10)
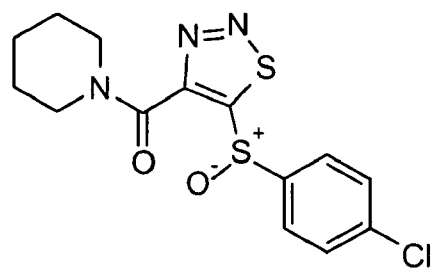
Formula 20 (Compound #11)
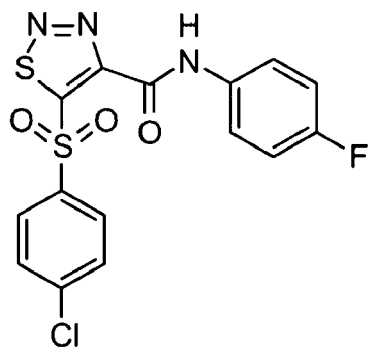
Formula 21 (Compound #12)
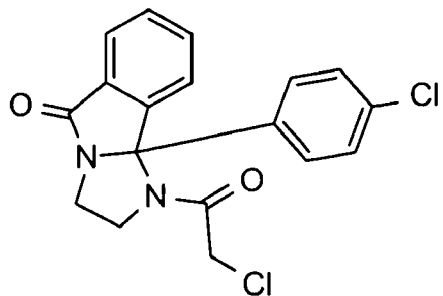
Figure 9A
Formula 22 (Compound #13)

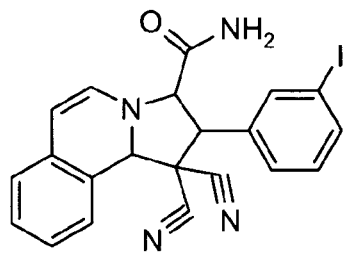
Formula 23 (Compound #17)
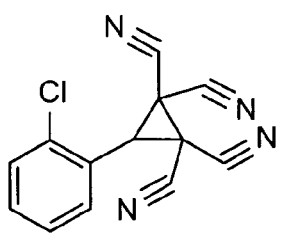
Formula 24 (Compound #21)
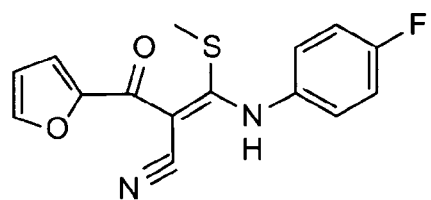
Formula 25 (Compound #22)
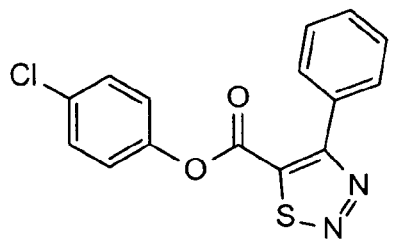
Formula 26 (Compound #23)
Figure 9B

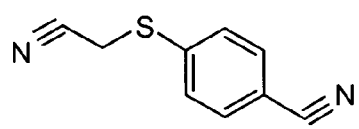
Formula 27 (Compound #24)
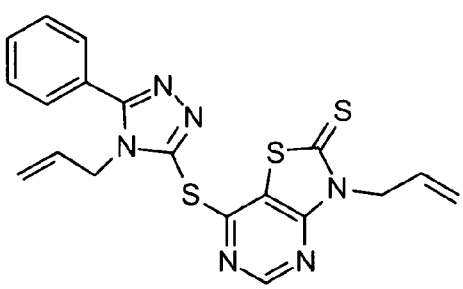
Formula 28 (Compound #27)
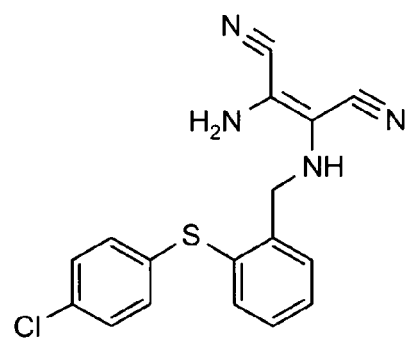
Formula 29 (Compound #29)
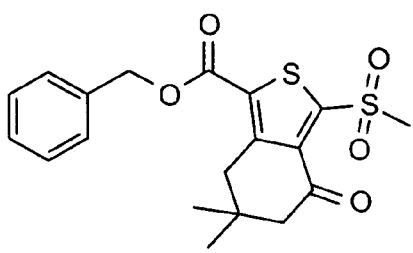
Formula 30 (Compound #30)
Figure 10A

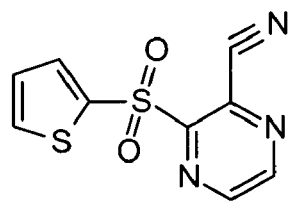
Formula 31 (Compound #31)
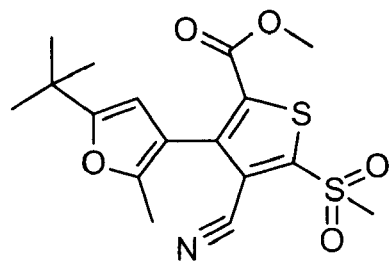
Formula 32 (Compound #33)
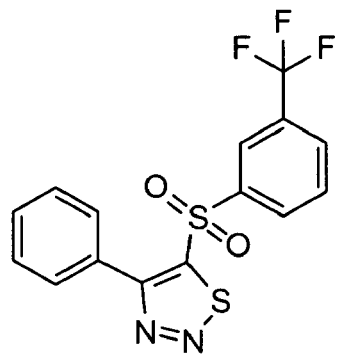
Formula 33 (Compound #35)
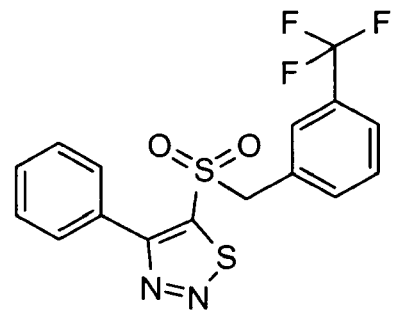
Formula 34 (Compound #36)
Figure 10B

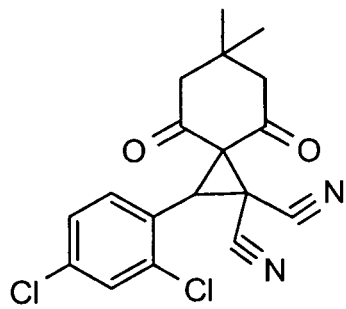
Formula 35 (Compound #37)
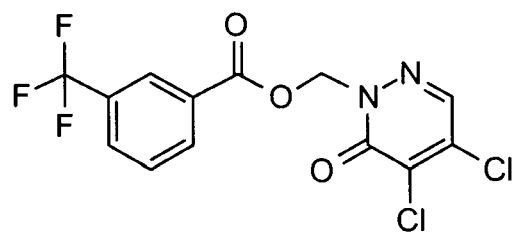
Formula 36 (Compound#38)
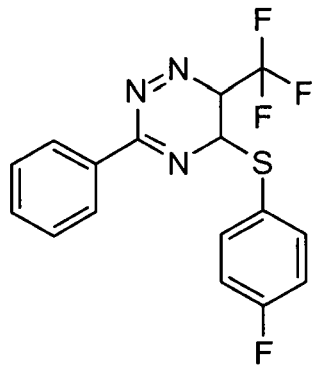
Formula 37 (Compound #39)
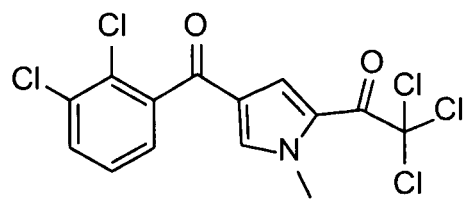
Formula 38 (Compound #40)
Figure 11A

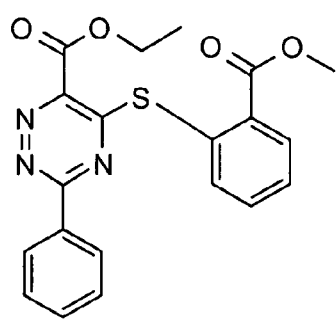
Formula 39 (Compound #41)
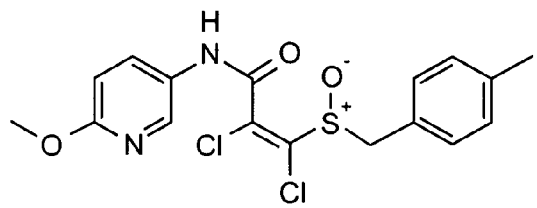
Formula 40 (Compound #43)
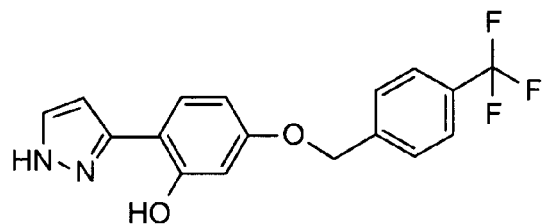
Formula 41 (Compound #44)
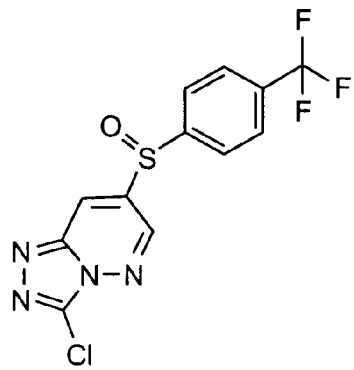
Formula 42 (Compound #45)
Figure 11B

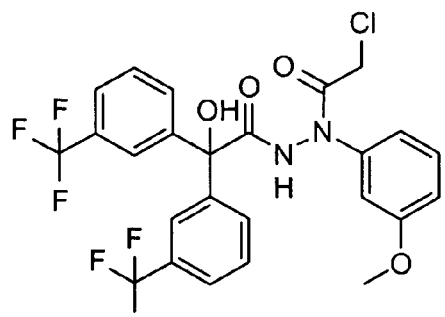
Formula 43 (Compound #51)
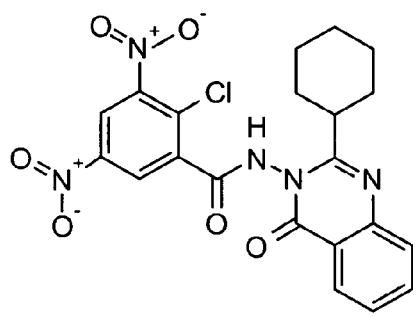
Formula 44 (Compound #53)
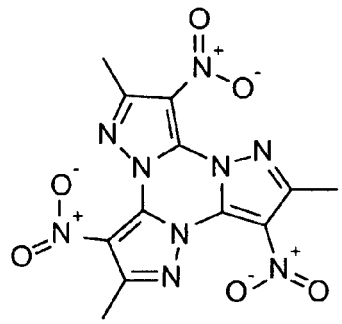
Formula 45 (Compound #54)
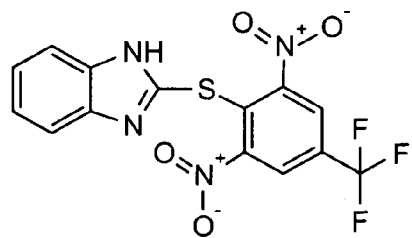
Formula 46 (Compound #55)
Figure 12A

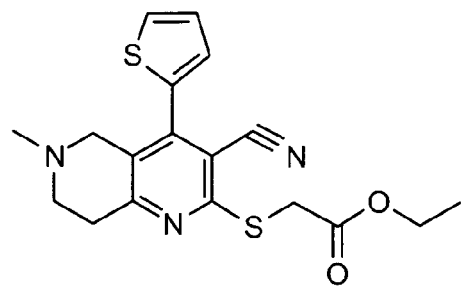
Formula 47 (Compound #56)
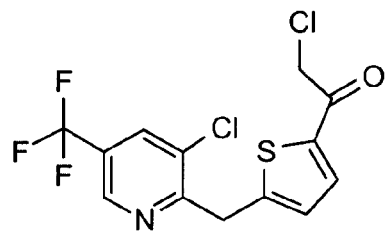
Formula 48 (Compound #57)
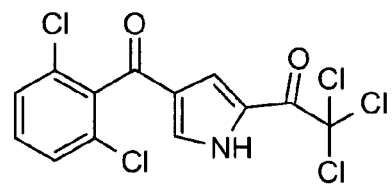
Formula 49 (Compound #58)
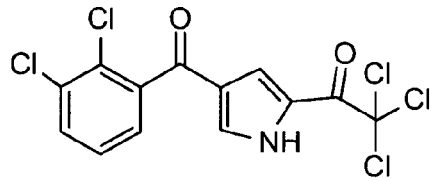
Formula 50 (Compound #59)
Figure 12B

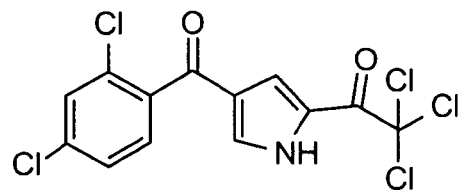
Formula 51 (Compound #62)
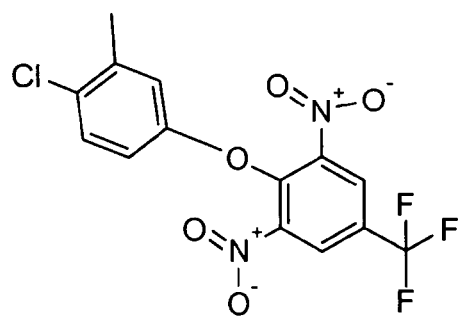
Formula 52 (Compound #64)
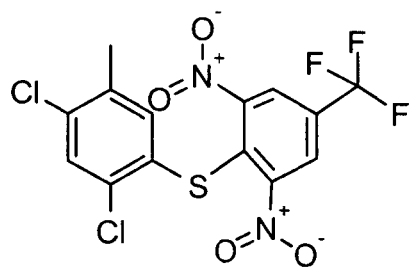
Formula 53 (Compound #65)
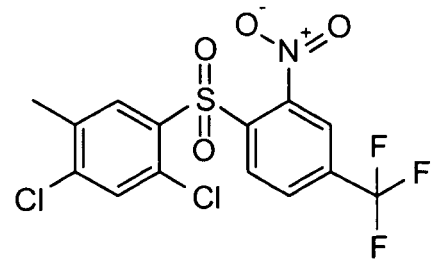
Formula 54 (Compound #66)
Figure 13A

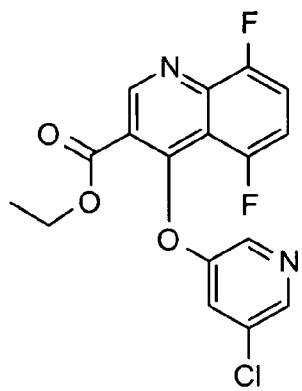
Formula 55 (Compound #67)
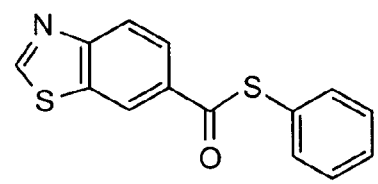
Formula 56 (Compound #68)
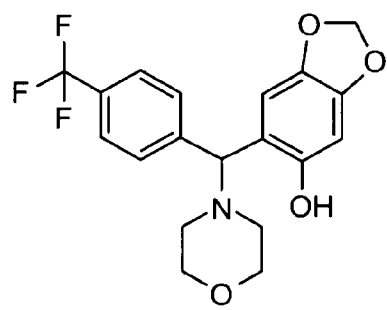
Formula 57 (Compound #69)
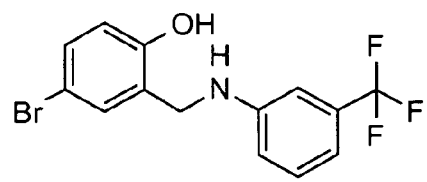
Formula 58 (Compound #70)
Figure 13B

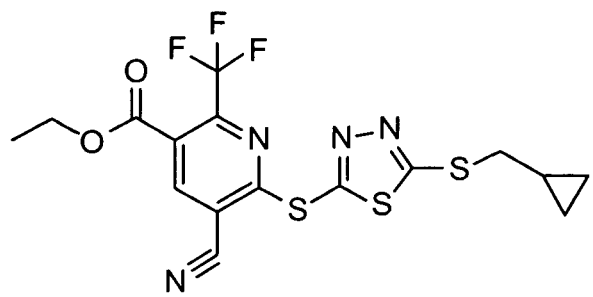
Formula 59 (Compound #71)
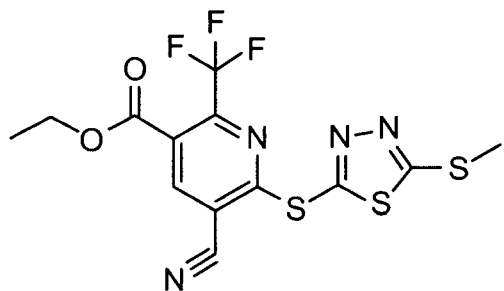
Formula 60 (Compound #72)
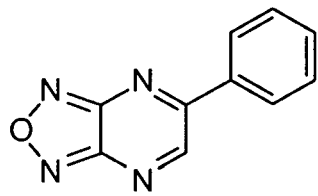
Formula 61 (Compound #74)
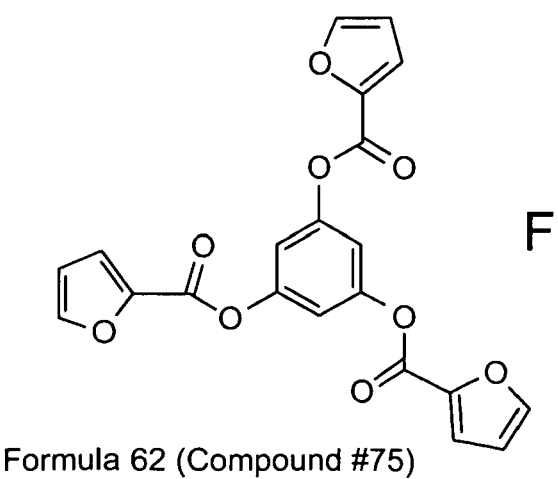
Figure 14A
Formula 62 (Compound #75)

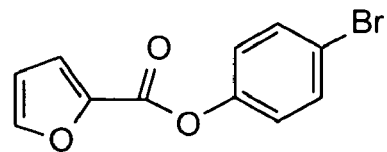
Formula 63 (Compound #76)
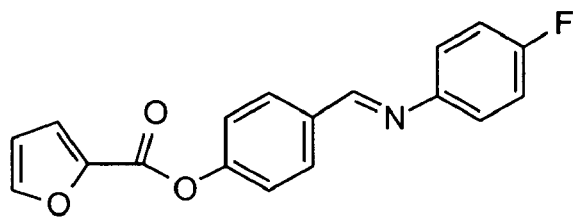
Formula 64 (Compound #77)
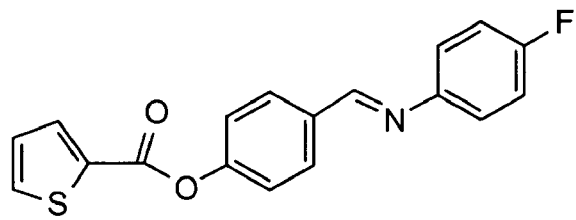
Formula 65 (Compound #78)
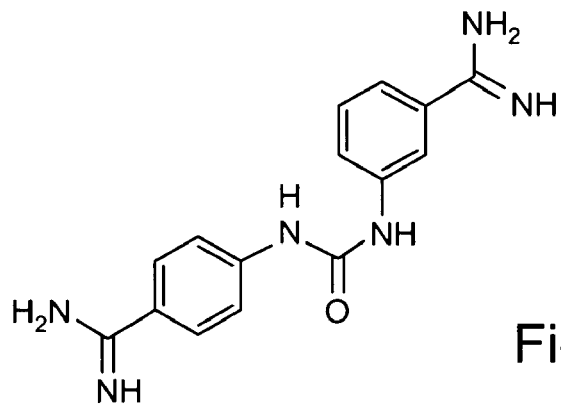
Formula 66 (Compound #80)
Figure 14B

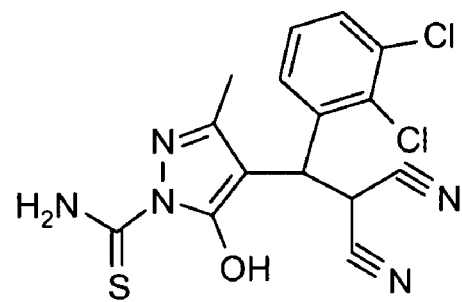
Formula 67 (Compound #81)
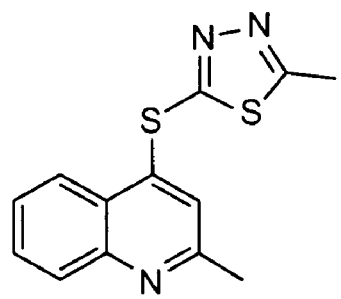
Formula 68 (Compound #82)
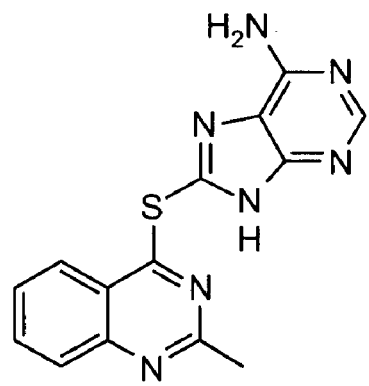
Formula 69 (Compound #83)
Figure 15

```
                        SEQUENCE LISTING

<160> NUMBER OF SEQ ID NOS: 4

<210> SEQ ID NO 1
<211> LENGTH: 96
<212> TYPE: PRT
<213> ORGANISM: Mycobacterium tuberculosis

<400> SEQUENCE: 1

Cys Leu Thr Ala Ser Thr Arg Ile Leu Arg Ala Asp Thr Gly Ala Glu
1               5                   10                  15

Val Ala Phe Gly Glu Leu Met Arg Ser Gly Glu Arg Pro Met Val Trp
            20                  25                  30

Ser Leu Asp Glu Arg Leu Arg Met Val Ala Arg Pro Met Ile Asn Val
        35                  40                  45

Phe Pro Ser Gly Arg Lys Glu Val Phe Arg Leu Arg Leu Ala Ser Gly
    50                  55                  60

Arg Glu Val Glu Ala Thr Gly Ser His Pro Phe Met Lys Phe Glu Gly
65                  70                  75                  80
```

```
Trp Thr Pro Leu Ala Gln Leu Lys Val Gly Asp Arg Ile Ala Ala Pro
                85                  90                  95

<210> SEQ ID NO 2
<211> LENGTH: 96
<212> TYPE: PRT
<213> ORGANISM: Mycobacterium tuberculosis

<400> SEQUENCE: 2

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

<210> SEQ ID NO 3
<211> LENGTH: 38
<212> TYPE: PRT
<213> ORGANISM: Mycobacterium tuberculosis

<400> SEQUENCE: 3

Asp Ala Tyr Trp Asp Thr Val Val Glu Ile Thr Ser Ile Gly Asp Gln
1               5                   10                  15

His Val Phe Asp Gly Thr Val Ser Gly Thr His Asn Phe Val Ala Asn
            20                  25                  30

Gly Ile Ser Leu His Asn
        35

<210> SEQ ID NO 4
<211> LENGTH: 38
<212> TYPE: PRT
<213> ORGANISM: Mycobacterium tuberculosis

<400> SEQUENCE: 4

Glu Leu Arg Tyr Ser Val Ile Arg Glu Val Leu Pro Thr Arg Arg Ala
1               5                   10                  15

Arg Thr Phe Asp Leu Glu Val Glu Leu His Thr Leu Val Ala Glu
            20                  25                  30

Gly Val Val Val His Asn
        35
```

METHODS AND COMPOSITIONS FOR SPECIFIC INHIBITION OF PROTEIN SPLICING BY SMALL MOLECULES

GOVERNMENT SUPPORT

This invention was made with Government support under contract number R43 AI052583-01A1 to Boston Biotechnology Corporation, awarded by the National Institutes of Health. The Government has certain rights in the invention.

BACKGROUND OF THE INVENTION

Globally, tuberculosis (TB) is the most widespread infectious disease. One third of the world's population (2 billion people) are infected with *M. tuberculosis* and 5-10% of these suffer active disease, leading to nearly 3 million deaths annually. Although, in the long-term, vaccination is the only way to eliminate tuberculosis, especially in developing countries where lengthy combination drug therapy is problematic, this does not address the need of the 2 billion individuals who are infected right now nor of the alarmingly growing number of patients in developed countries who are suffering from multidrug-resistant (MDR) TB, which is essentially refractory to drug therapy (Espinal et al., *N. Engl. J. Med.* 344:1294-1303 (2001)). A special concern is the link between AIDS and TB. Thirty-one % of TB cases in Africa and 26% of those in the USA are associated with HIV infection and the death of 11% of all HIV patients is caused by TB (Corbett et al., *Arch. Intern. Med.* 163: 1009-1021 (2003)). The mainline anti-tuberculosis drugs isoniacid, rifampin, pyrazinamide, ethambutol, and, secondarily, streptomycin thus need be supplemented by additional drugs against new targets, until those, too, succumb to resistance mechanisms. It is therefore important to keep developing an armamentarium of drugs against a wide range of targets to use in combination with established drugs and replace these when they begin to fail. In addition, the ability of *M. tuberculosis* to persist in a patient for decades in a state refractory to most known antibacterial agents puts a great premium on the discovery of new drugs capable of targeting the persistent state. Another context in which a new type of anti-mycobacterial drugs would play an important role is in response to bioterrorist attacks that may involve *M. tuberculosis*. In such a situation, it may be desirable to treat large populations prophylactically to avoid the establishment of infections, the treatment of which would require a long course of costly multidrug therapy.

The search for new anti-tuberculosis drugs aimed at new targets therefore deserves to be given high priority. Effective cure of MDR TB requires long-term treatment with anti-TB drugs and that in the event of a bioterrorist attack, large populations must be treated prophylactically with a suitable antibiotic. If the antibiotic to be used in these situations were a broad-spectrum drug, it would not only affect a significant fraction of the subject's normal bacterial flora but could stimulate the emergence of resistance among other pathogens carried by the treated population. These problems would not arise with a drug targeted specifically against *M. tuberculosis*.

DnaB is a DNA helicase that functions in the initiation of lagging-strand DNA synthesis (Arai and Kornberg, *Proc. Natl. Acad. Sci. USA* 76: 4308-4312 (1979)) as a component of the primosome (Saluja and Godson, *J. Bacteriol.* 177: 1104-1111 (1995)). Specifically, it unwinds the DNA duplex ahead of the replication fork and recruits the DnaG primase to the primosome. The essential role of *E. coli* DnaB in DNA replication is indicated by the existence of temperature-sensitive dnaB mutants (Kogama, T., *J. Mol. Biol.* 103: 191-197 (1976)). The functional form of the DnaB protein is a hexamer which interacts directly with 2-3 molecules of the DnaG primase (Bird et al., *Biochemistry* 39: 171-182 (2000)). In the light of the complex protein-protein interactions in which DnaB participates, which may also include the products of the dnaA, dnaC, and dnaX genes, it is quite unlikely that the 465-residue DnaB helicase can function without the excision of the 415-residue intein.

As in enteric bacteria, the *M. tuberculosis* RecA protein initiates the SOS response to DNA damage by polymerizing to filaments at the site of DNA lesions (Movahedzadeh et al., *J. Bacteriol.* 179: 3509-3518 (1997)). However, a major difference between *M. tuberculosis* and other bacteria in the induction of the SOS response is that the *M. tuberculosis* RecA protein is synthesized in an inactive form, which has to undergo protein splicing before it can assume its role in the initiation of DNA repair. It should be noted that RecA is not essential for bacterial growth except under conditions of excessive DNA damage. Since *M. tuberculosis* is an intracellular pathogen, the repair of DNA damage inflicted by the reactive oxygen and nitrogen species produced by macrophages must play an important role in its survival in the infected host. However, recA mutants of *M. bovis* BCG, a non-virulent mycobacterial strain but highly susceptible to killing by DNA damaging agents, were not compromised in terms of survival in a nude mouse model, but, when studied in an in vitro model for persistence, had a greatly enhanced sensitivity to metronidazole (Sander et al., *Inf. Immun.* 69: 3562-3568 (2001)). On the other hand, recent work has suggested an important role of RecA on in vivo survival and the emergence of drug resistant mycobacteria. One of the enzymes, which is induced by the SOS response to DNA damage (Davis et al., *J. Bacteriol.* 184: 3287-3295 (2002)) and whose induction absolutely requires functional RecA (Rand et al., *Mol. Microbiol.* 50: 1031-1041 (2003)), is an error-prone DNA polymerase, DnaE2 (Boshoff et al., *Cell* 113: 183-193 (2003)). In *Mycobacterium smegmatis*, disruption of either dnaE2 or recA reduced the number of UV-induced RifR mutations 10- to 25 fold, respectively, to nearly background levels. In *M. tuberculosis*, only the effect of dnaE2 disruption was examined, which essentially prevented any DNA damage induced RifR mutations and, when tested in an infected mouse model, almost doubled the medium survival time and reduced lung CFU counts nine month post-infection 10-fold (Boshoff et al., *Cell* 113:183-193 (2003)). DnaE2 and, by extension, RecA, which is essential for DnaE2 induction, thus appear to be important players in the emergence of drug-resistance mutations and in the longterm survival of *M. tuberculosis* in the infected host.

Protein splicing is a form of post-translational processing that consists of the excision of an intervening polypeptide sequence, the intein, from a protein, accompanied by the concomitant joining of the flanking polypeptide sequences, the exteins, by a peptide bond (FIG. 1). It proceeds by a series of four reactions that are catalyzed entirely by the intein and require no cofactors or accessory proteins (Paulus, H., *Annu. Rev. Biochem.* 69: 447-496 (2000)). About 200 inteins are known, distributed in unicellular representatives of eukaryotes, archaea, and bacteria (Perler, F. B., *Nucl. Acids Res.* 30: 383-384 (2002)). The fact that protein splicing does not occur in higher eukaryotes and has a limited distribution among eubacteria, with *Mycobacterium* as the only pathogenic representative, makes it a very attractive antimycobacterial target.

*M. tuberculosis* harbors three inteins, which interrupt the DnaB, RecA, and SufB (Rv1461) proteins. As discussed in the next section, the DnaB and RecA proteins play important roles in DNA replication and repair, respectively, whereas SufB is a component of the Fe—S cluster assembly and repair SUF machinery (Huet, G., Daffe, M., and Saves, I. *J Bacteriol* 187: 6137-6146 (2005)) and is essential for growth (Sassetti, C. M., Boyd, D. H., and Rubin, E. *J. Mol. Microbiol* 48: 77-84 (2003)). We have focused our attention on the DnaB and RecA inteins, whose protein splicing domains, compared in FIG. 2, show 29% amino acid identity and 44% similarity, not only in the conserved protein splicing motifs but in other regions, suggesting a close evolutionary relationship. The high degree of similarity of these inteins, as well as the fact that even relatively unrelated inteins have almost identical 3-D structures (e.g., Paulus, Annu. Rev. Biochem. 69:447-496 (2000)), makes it quite likely that substances can be found which are inhibitors of protein splicing catalyzed by both of these inteins. Although we are not specifically focusing on the study of the SufB (Rv1461) intein, its protein splicing domain has 17% identity and 31% similarity to the that of the DnaB intein, suggesting that its structure is similar to the structure of the DnaB and RecA inteins and that all three inteins may be susceptible to the same inhibitors.

Protein splicing inhibitors that inhibit the function of both the DnaB and the RecA inteins hold several important advantages as anti-TB drugs. First, the inhibition of two separate targets, DNA replication (DnaB) and DNA repair (RecA) would produce synergistic effects, leaving more chance of success against infection. Secondly, the inhibitors by design would not interact with DnaB and RecA directly and resistance could therefore not arise from mutations in the catalytic domains of these proteins but only from mutations in the intein. It is known that the majority of intein mutations leads to uncoupling of the protein splicing pathway (Chong et al., *J. Biol. Chem.* 273: 10567-10577 (1998)), which would result in a reduction of protein splicing activity instead of fostering resistance. Additionally, inhibition of DnaB would directly inhibit growth and simultaneous inhibition of RecA would prevent induction of error-prone DNA repair. Since error-prone DNA repair contributes to persistence and most mutations to drug-resistance, inhibition of the same would suppress the emergence and growth of bacterial strains with inhibitor-resistant DnaB and RecA inteins. Finally, because higher eukaryotes, pathogens other than *Mycobacterium*, and bacteria normally associated with humans do not bear inteins, protein splicing inhibitors would therefore be narrow spectrum antibiotics specific for *Mycobacterium*. Resultingly, such inhibitors would be expected to have no major side effects.

DESCRIPTION OF RELATED PRIOR ART

Prior to the present invention, the only known inhibitors of protein splicing, other than unspecific agents that perturb protein structure or chemically modify amino acid side chains, include $Zn^{2+}$ ion, strong reducing agents such as dithiothreitol (DTT) and strong nucleophiles such as hydroxylamine (Mills and Paulus, *J. Biol. Chem.* 241: 10832-10838 (2001); Ghosh et al., *J. Biol. Chem.* 276: 24051-24058 (2001)). While perhaps suitable for in vitro use, such agents are not practical for in vivo use as inhibitors of protein splicing simply because they lack specificity for controlling intein excision. Because of this lack of specificity, such agents administered at concentrations effective to control intein activity would be toxic to any cell or organism and therefore would be expected to exhibit major side effects. Although U.S. Pat. No. 5,834,247, the contents of which are herein incorporated by reference, surmises that peptides may act as inhibitors of protein splicing, no such inhibitors are currently in existence. As such, there is a need for the identification of new small molecule inhibitors of protein splicing suitable for in vivo use.

BRIEF DESCRIPTION OF THE DRAWINGS

FIG. 2 shows an alignment of the protein splicing domains of the *M. tuberculosis* DnaB (SEQ ID NOS 1 and 3, respectively) and RecA (SEQ ID NOS 2 and 4, respectively) inteins. The conserved protein splicing motifs (Pietrokovski, S., *Protein Science* 7: 64-71 (1998)) are shown by boxes and identical residues are highlighted in dark shading, similar residues in light shading.

FIGS. 8A & B depict the structures of compounds represented by Formulas 11-14 (FIG. 8A) and 15-18 (FIG. 8B) depicted as Compounds #1-4 and 6-9.

FIGS. 9A & B depict the structures of compounds represented by Formulas 19-22 (FIG. 9A) and 23-26 (FIG. 9B) and depicted as Compounds #10-13, 17 and 21-23.

FIGS. 10A & B depict the structures of compounds represented by Formulas 27-30 (FIG. 10A) and 31 1-34 (FIG. 10B) depicted as Compounds #24, 27 and 29-34.

FIGS. 11A & B depict the structures of compounds represented by Formulas 35-38 (FIG. 11A) and 39-42 (FIG. 11B) and depicted as Compounds #37-41 and 43-45.

FIGS. 12A & B depict the structures of compounds represented by Formulas 43-46 (FIG. 12A) and 47-50 (FIG. 12B) and depicted as Compounds #51 and 53-59.

FIGS. 13A & B depict the structures of compounds represented by Formulas 51-54 (FIG. 13A) and 55-58 (FIG. 13B) and depicted as Compounds #62 and 64-70.

FIGS. 14A & B depict the structures of compounds represented by Formulas 59-62 (FIG. 14A) and 63-66 (FIG. 14B) and depicted as Compounds #71, 72, 74-78 and 80.

FIG. 15 depicts the structures of compounds represented by Formulas 67-69 and depicted as Compounds 81-83.

DETAILED DESCRIPTION OF THE INVENTION

Figure 1:
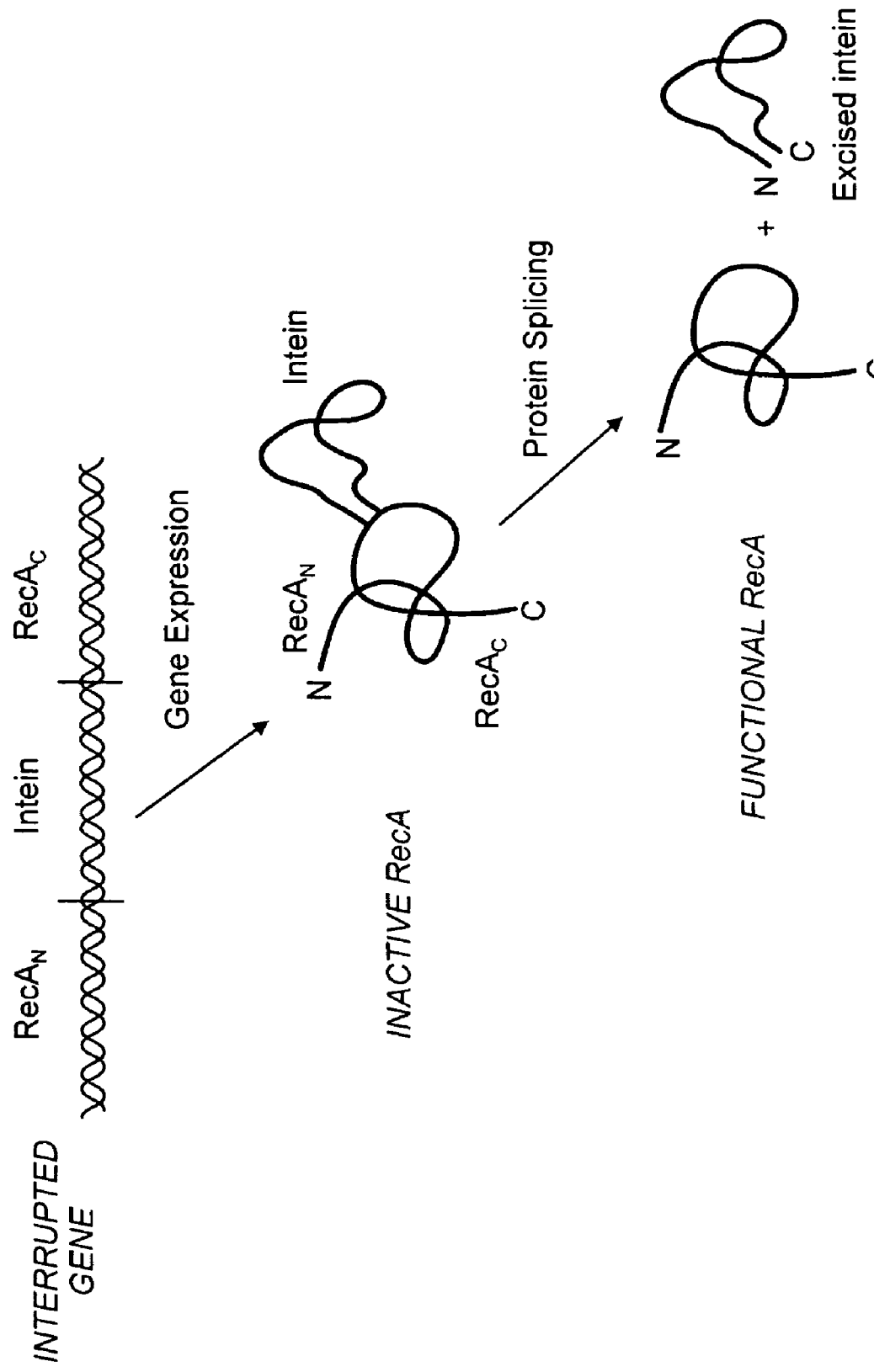
FIG. 1 depicts the role of protein splicing in gene expression. The primary translation product is an inactive protein precursor that is converted to the functional protein by protein splicing.

The present invention is based on the finding that a subset of previously existing small molecules can function as inhibitors of protein splicing. This subset comprises a group of organic small molecules, each of which alone has the ability to specifically bind an intein-containing protein and function as an inhibitor of protein splicing. The present invention is based on the identification of this new class of small molecule inhibitors of protein splicing, and is directed to such compositions and methods for their use. The invention provides the first instance of a small molecule inhibitor of protein splicing with drug-like characteristics.

In one aspect, the invention relates to a method for treating tuberculosis, the method comprising administering a small molecule inhibitor of protein splicing to a human in need of such treatment. The small-molecule inhibitor of protein splicing is to be administered in an amount and for a period of time, effective to therapeutically treat an individual suffering from tuberculosis. In this method, the inhibitor may be a non-peptide inhibitor. The inhibitor may further be characterized as having a molecular weight of greater than 200, or more preferably in the range of from about 200 to about 600. A method for treating tuberculosis may comprise administering to a human in need of such treatment a small-molecule inhibitor selected from the group consisting of compounds of formulas 1-10 as recited in Table 1 or from the group of specific compounds of formulas 11-69 as recited in FIGS. 8-15 (some compounds of the latter group being included in the generic structures recited in Table 1), or pharmaceutical salts thereof. Selected inhibitors of RecA and DnaB intein splicing and their drug-likeness, ClogP, and solubility properties are shown in Table 4 and FIG. 8-15. The likely efficacy and specificity of these inhibitors in treating tuberculosis is apparent in that half of the inhibitors recovered had IC50's below 10 µM, and that many had high drug scores based on the Lipinski criteria (Lipinski et al., *Adv. Drug Delivery Rev.* 46: 3-26 (2001)).

TABLE 1

Selected classes of inhibitors of protein splicing.

| | Structure | Variable chemical groups |
|---|---|---|
| Formula 1 | [structure] | X is oxygen or sulfur; R is an aromatic group |
| Formula 2 | [structure] | R is hydrogen or methyl; Ar is phenyl, which may be substituted with halogen or trifluoromethyl |
| Formula 3 | [structure] | $R_1$ is an aromatic or aromatic carboxamide group; $R_2$ is an aromatic sulfone or sulfoxide group or an aromatic ester. |
| Formula 4 | [structure] | X is H or an alkyl group |
| Formula 5 | [structure] | R is an alkyl or acyl ester group; Ar is an aromatic group |

TABLE 1-continued

Selected classes of inhibitors of protein splicing.

| | Structure | Variable chemical groups |
|---|---|---|
| Formula 6 | 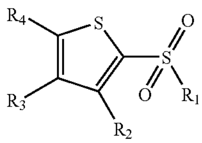 | $R_1$ is a methyl or aromatic group; $R_2$ is H, nitrile, or an acyl group; $R_3$ is H, an alkyl, or an aromatic group; $R_4$ is H or an ester group |
| Formula 7 | 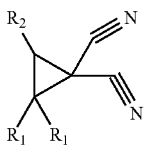 | $R_1$ is nitrile or an aliphatic ketone group; $R_2$ is an aromatic group |
| Formula 8 | 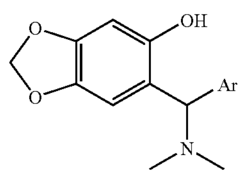 | Ar is an aromatic group |
| Formula 9 | 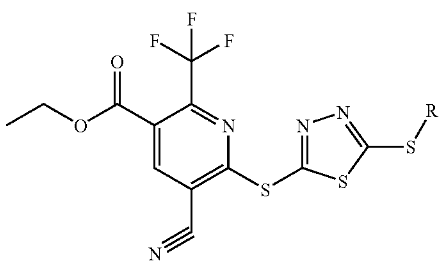 | R is an alkyl group |
| Formula 10 | 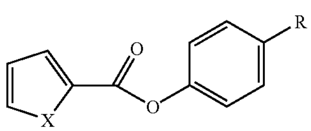 | X Is O or S; R is Br or a CHO as Schiff base with p-F-aniline |

In a method for treating tuberculosis, the inhibitor may be delivered alone or in combination with other therapies, including the delivery of antibiotics effective against *Mycobacterium*. An inhibitor may also be used in conjunction with another inhibitor. The amount of inhibitor and duration of treatment may vary among individuals to be treated, and may depend on the identity of the specific inhibitor compound of choice. Delivery of a small molecule inhibitor of protein splicing to affected individuals may be accomplished intravenously, subcutaneously, intraperitoneally, intramuscularly, whereas oral administration is likely preferred.

In another aspect, the invention relates to a composition comprising a small-molecule inhibitor of protein splicing in a pharmaceutically acceptable carrier, wherein the inhibitor is an organic compound with the ability to specifically interact with an intein-containing protein. While not wishing to be bound by theory, the small-molecule inhibitor of protein splicing may interact covalently or noncovalently with the intein-containing protein. The small-molecule inhibitor may be characterized as a non-peptide inhibitor of protein splicing. Although not required, a small molecule inhibitor of the present invention may further be characterized as having a molecular weight of greater than 200 Da (Daltons), or more preferably in the range of from about 200 Da to about 600 Da. The small-molecule inhibitor of protein splicing may be selected from the group consisting of compounds of formulas 1-10 as recited in Table 1 or from the group of specific compounds of formulas 11-69 as recited in FIGS. 8-15 (some compounds of the latter group being included in the generic structures recited in Table 1), or pharmaceutical salts thereof. A small-molecule compound contained within the pharmaceutical composition of this invention may be provided in the form of a pharmaceutically acceptable salt. A pharmaceutical composition of this invention contains a therapeutically effective amount of active inhibitor, and, as may be necessary, inorganic or organic, solid or liquid pharmaceutically acceptable carriers.

An inhibitor of protein splicing of the present invention is an organic compound that binds specifically to an intein-containing protein with high affinity. A small molecule inhibitor of the present invention differs from any of the relatively nonspecific agents that are known in the art to interfere with protein splicing (e.g. DTT and hydroxylamine) in that the small-molecule inhibitor of the present invention binds to an intein-containing protein in a specific fashion. In contrast, any of the reducing agents or strong nucleophiles in the art that inhibit protein splicing are known to do so non-specifically.

One skilled in the art will recognize that other inhibitor compositions may be found using any effective method for screening for inhibitors of protein splicing. Paulus et al. (*Anal. Chem.* 2003, 75, 2456-2462) teaches an in vitro assay using fluorescence of GFP as a direct measure of intein activity, which may be utilized for this task. A variation of Paulus et al. using GFP for high throughput screening is provided in the Exemplification herein. Alternatively, U.S. Pat. Nos. 5,795,731 and 6,521,425, both of which are herein incorporated by reference, teach cell-based assays for identifying inhibitors of protein splicing. Instead of assaying for in vitro GFP activity, the '731 and '425 patents teach selection of agents that control splicing by monitoring bacterial cells for the production of thymidylate synthase (TS) and cell viability, respectively. The present invention provides the first evidence that specific inhibition of protein splicing by small molecules is achievable. It is very likely that other specific small-molecule inhibitors may be determined using existing screening methods, modified methods thereof, or new methods assaying for intein activity. Compositions identified as inhibitors of protein splicing in such screens may be used in any of the methods of the present invention.

The high degree of similarity of the DnaB and RecA inteins, as well as the fact that even relatively unrelated inteins have almost identical 3-D structures (e.g., Paulus, H., *Annu. Rev. Biochem.* 69: 447-496 (2000)), makes it quite likely that small molecule inhibitors of the present invention may inhibit protein splicing catalyzed by not only these inteins, but also other naturally occurring and man-made inteins. As such, the term "intein" herein is intended to include any naturally occurring or man-made intein and any man-made modification thereof. There are no strict requirements as to the sequence of the intein, and accordingly, a modified intein may contain substitutions and/or modifications which do not substantially affect its activity. The term "activity" in the context of intein function herein is intended to be synonymous with cleavage and/or excision. In some contexts, cleavage without excision may be the preferred embodiment. In other contexts, cleavage with excision may be preferred. An "inhibitor" of the present invention is herein defined as a small-molecule capable of effecting at least about 20% reduction in activity of an intein. An "inhibitor" of the present invention is more preferably capable of effecting at least about 50% reduction in intein activity and most preferably at least about 90% when complete inhibition is required. When modulation of activity, as opposed to complete inhibition, is desired, a weaker inhibitor may be preferred.

The term "protein" in the context of the present invention is intended to encompass any full-length protein as well as any truncation, deletion, and/or substitution of the same. "Protein" is also intended to encompass a polypeptide or peptide. An intein-containing protein is a protein, as defined herein, containing an intein. The intein may be C-terminal or N-terminal when fused to a protein, or it may be an intervening sequence. There are no strict requirements as to the position of an intein within a protein, unless otherwise specified. The intein-containing protein may be expressed from an exogenous transgene or vector. Alternatively, an intein coding sequence may be inserted into an endogenous gene, thereby altering the function of that gene.

It is an object of the invention to provide a method for inhibiting protein splicing. This method comprises contacting an intein-containing protein with a small-molecule inhibitor of protein splicing, wherein the inhibitor is an organic compound which interacts with the protein specifically. The contacting step, carried out in vitro may be used for preventing excision of an intein, and hence activation of an intein-containing protein. The contacting step, carried out in vivo may be used for gene therapy methods in addition to treating tuberculosis. As in the case of DnaB and RecA in *Mycobacterium*, the intein-containing protein may be a naturally occurring protein. As for in vitro methods and methods for gene therapy, the intein-containing protein may be a product of genetic engineering. Any inhibitor composition of the invention may be used in accordance with this method.

Intein-containing proteins which can be used in accordance with the present invention include, for example, enzymes, toxins, cytokines, transcription factors, and growth factors. Many proteins that fall under such categories are known to the skilled artisan. One skilled in the art may design intein-containing proteins using known amino acid and nucleotide sequences of such proteins obtained from databases such as those of NCBI, EMBL, and Swiss-Prot. Alternatively, one skilled in the art may design intein-containing proteins from unknown sequences using standard procedures that are known in the art. Sequences of naturally occurring, modified, and man-made inteins are known in the art and may be adapted for use in the methods of the present invention.

In certain embodiments of the present invention, the intein is to be inserted into a region of a protein whereby the insertion renders the protein substantially inactive. Use of an inhibitor of the present invention allows the maintenance of this inactivity during and subsequent to translation, and further allows controlled intein excision. Inhibition of an intein's self-catalyzed excision and its subsequent induced excision allows the restoration of protein activity at a desired point in time.

If substantial inactivation of a protein is desirable, the intein is to be inserted into a region of a desired protein that will disrupt its activity. Such regions are well known to one skilled in the art and include DNA binding regions, cofactor binding regions, enzyme active sites, and highly conserved regions. Such regions are readily identifiable by sequence analysis or alignment of the amino acid sequence with known protein sequence databases. Alternatively, the effect of an intein on a protein's activity may be determined by trial and error. An intein may be randomly inserted into various region(s) of a protein, and the activity of the protein assayed in both the presence and absence of the inhibitor until a determination of inhibition may definitively be made.

A method for activating the function of a protein may comprise providing a protein which is interrupted by an intein wherein the intein renders the protein inactive, and further wherein the protein is provided in the presence of a small-molecule inhibitor of protein splicing at an effective concentration. The effective concentration is defined in this context as the concentration sufficient to inhibit excision of the intein. The method further comprises thereafter enabling excision of the intein by reducing the inhibitor to a level below the effective concentration. The excision thereby activates the function of the protein to a significant degree. It is an object of the invention that any of the inhibitor compositions herein may be utilized in conjunction with this method. A method for activating the function of a protein may be carried out either in vitro or in vivo. In vivo or in cell culture, this method for activating the function of a protein may be useful for studying the function of a protein (and the consequence of its absence) in living cells.

For use in gene therapy, the intein-containing protein may be expressed under the control of a tissue-specific promoter.

An intein-containing protein may be targeted to a particular cell-type, such as a tumor or other type of cell to be treated. The intein-containing protein may be expressed in that particular cell type and be inactive, provided that the individual to be treated is being treated with an inhibitor of protein splicing. Enabling excision of the intein by reducing the inhibitor in that cell type to a level below the effective concentration may render the protein pharmacologically active and thereby treat the affected cells. In the case of foreign cells such as cancerous cells, enabling excision of the intein may further render the protein cytotoxic, and thereby kill the affected cells. Use of the inhibitor in this context may help to control concentrations of an active desired protein, thereby reducing potential side effects. For example, an inhibitor of the present invention may be administered at low, intermediate, or high dosages, depending on whether high, intermediate, or low activity, respectively, is desired. Alternatively, when modulation of activity, as opposed to complete inhibition, is desired, a weaker inhibitor of the present invention may be employed.

One skilled in the art would recognize that an intein in the context of the present invention may be inserted into a protein in many different ways. The primary amino acid sequence of the intein-containing protein may be chemically synthesized using standard methods in the art. Alternatively, the intein-containing protein may be obtained from expressing the protein from the proper intein-containing DNA sequence. The intein coding sequence may be inserted into the desired protein coding sequence at a desired location, thereby forming a continuous reading frame. The intein DNA sequence may be ligated in-frame to a linear plasmid sequence containing the protein coding sequence, the linear sequence formed by a restriction endonuclease cut at the desired region of intein insertion. An intein DNA sequence may be PCR amplified from an existing genetic pool harboring the sequence, and restriction sites conducive to such a ligation may be engineered onto primers. Or, following PCR amplification, the ends may be blunted with the use of an exonuclease, and the resulting fragment blunt-end ligated to the linearized plasmid containing protein. If intein excision is used to control the activity of the protein, it is important that the excision of the intein leave the protein sequence in-frame. Other examples of intein-containing protein design and construction are disclosed in U.S. Pat. No. 5,496,714, the contents of which are herein incorporated by reference.

An intein used in the context of the present invention may be altered so that cleavage without excision may occur in the absence of the inhibitor. Cleavage in the absence of excision may be desirable for use in protein engineering. U.S. Pat. No. 5,834,247 discloses cleavage and reconstruction of protein splicing precursors via splicing in trans. The present invention provides the researcher with a distinct advantage over the art in that strict control of splicing may be achieved with a small-molecule inhibitor. In contrast, the cleavage-inducing conditions in the art such as temperature and pH can be difficult to control in culture and impossible to use in vivo. A method for controlling the activity of an intein may comprise providing an intein with its N-terminus or its C-terminus or both being fused to a protein, the intein fusion being provided in the presence of a small-molecule inhibitor of protein splicing at an effective concentration wherein the effective concentration provided is sufficient to inhibit activity of the intein. The method further comprises thereafter enabling cleavage of the intein at its N-terminus or its C-terminus or both by reducing the inhibitor to a level below the effective concentration, thereby controlling the activity of the intein.

This method may be carried out in vitro or in vivo. Any inhibitor composition of the invention may be used in accordance with this method.

In in vitro methods for inhibiting protein splicing, for activating the function of a protein, or for controlling the activity of an intein, the intein-containing protein may be provided in the presence of the small molecule inhibitor during synthesis of the protein. Providing the intein-containing protein in the presence of the small molecule inhibitor prevents excision of the intein, and in turn, activation of the protein during synthesis. If the protein is expressed in cells, the inhibitor may be added to cell culture media during cell growth or induction. The intein-containing protein may be further provided in the presence of the small-molecule inhibitor during purification of the protein. In this embodiment, the inhibitor may be added to protein buffers.

As a pharmaceutical for treating tuberculosis, the small molecule inhibitor of protein splicing is to be effective at inhibiting excision of a naturally occurring RecA and/or DnaB intein. Inhibition of intein excision in these cases disrupts the activities of these genes, thereby inhibiting growth of the pathogen. As a pharmaceutical for use in gene therapy, the small molecule inhibitor of protein splicing is to be effective at inhibiting a naturally occurring, man-made, or modified intein, the intein of which has been engineered into a protein sequence whose control is desired.

While not wishing to be bound by theory, a small molecule inhibitor of protein splicing of the present invention may inhibit any one or more of the 3 steps of protein splicing. A small molecule of the present invention may inhibit a first intein-catalyzed reaction by preventing an N—S/O acyl rearrangement at the intein N-terminus, in turn preventing formation of a linear ester intermediate. A small molecule of the present invention may inhibit a second intein-catalyzed reaction by preventing nucleophilic attack of the linear ester intermediate by a nucleophilic residue at the C-terminal splice site, thereby preventing formation of a branched ester intermediate. Additionally, a small molecule of the present invention may inhibit a third intein-catalyzed reaction by preventing cyclization of an Asn residue adjacent to the C-terminal splice junction and cleavage of the branched intermediate, thereby preventing intein excision and the joining of resulting exteins. A small molecule of the present invention may alternatively inhibit protein splicing by some other as yet unidentified process.

While specific compositions of the present invention are provided, it will be apparent to those skilled in the art that various modifications thereto can be made without departing from the spirit and scope of the invention as defined in the appended claims. Regarding any specific composition of the present invention, modifications of chemical groups which do not substantially and negatively alter the function of the inhibitor, or its drug-likeness character, are intended to fall within the scope of the invention.

EXEMPLIFICATION

1. Assay Development

Figure 3A:
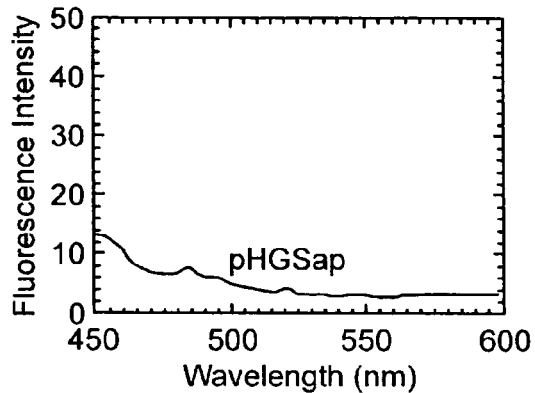
FIG. 3 shows the fluorescence of renatured inclusion bodies derived from *E. coli* transformed with plasmids pHGSap (A) and pHGmU (B). The inclusion bodies were dialyzed or diluted into buffer without urea, incubated for 18 h at 25° C., and equivalent samples were analyzed for fluorescence in response to excitation at 395 nm.
Figure 3B:
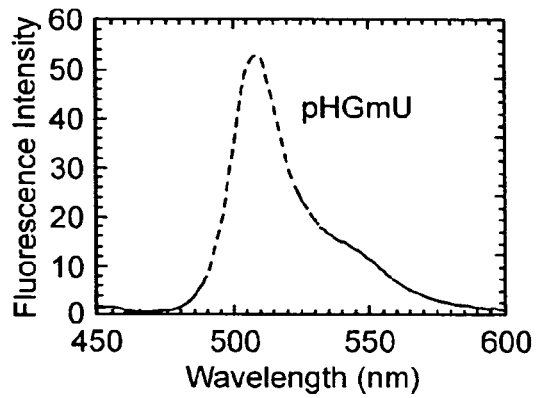
Figure 4A:
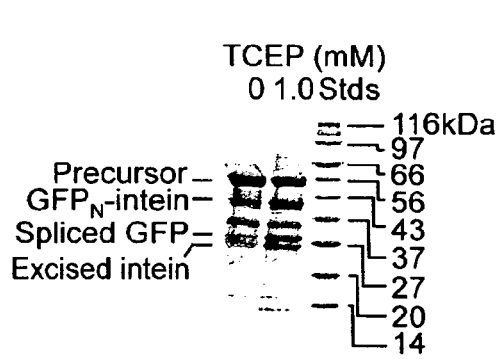
FIG. 4 shows protein splicing in vitro with the GFP/mini-intein fusion protein. Denatured inclusion bodies of GFP/mini-intein fusion protein were renatured by dialysis into buffer and incubated for 18 h at 25° C. in the absence or presence of TCEP. A. Protein splicing was followed by SDS-PAGE. B. Fluorescence generated by excitation at 395 nm was measured after appropriate dilution.
Figure 4B:
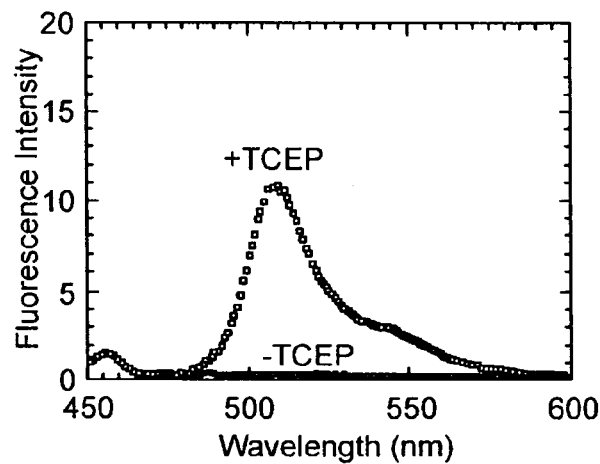

The high-throughput screening system makes use of Green Fluorescent Protein (GFP) as a fluorescent indicator and is based on the observation that GFP, interrupted by an intein, can undergo splicing to produce a functional protein (Ozawa et al., *Anal. Chem.* 72: 5151-5157 (2000)). The protein splicing domain of the *M. tuberculosis* RecA intein, in which the homing endonuclease domain was replaced by a His-tag to yield a so-called mini-intein, was inserted adjacent to a cysteine residue replacing isoleucine-129 of an optimized GFP variant [GFPuv or Cycle 3 mutant (Crameri et al., *Nature Biotech.* 14: 315-319 (1996))], which corresponds to the boundary of a beta-sheet and loop segment, to yield plasmid pHGmU (Gangopadhyay et al., *Anal. Chem.* 75: 2456-2462 (2003)). As a control, the coding sequence of a nonapeptide was inserted at the same site of GFP (pHGSap). When expressed in *E. coli* JM109 (DE3), both GFP fusion proteins were expressed as inclusion bodies and could be solubilized with 8 M urea as a non-fluorescent protein. Upon renaturation, only the GFP-RecA intein fusion protein developed fluorescence, but not GFP interrupted at the same site by the nonapeptide, demonstrated that the gain of fluorescence depends on protein splicing (FIG. 3). Renaturation can be achieved either by dialysis or dilution, but both protein splicing and the gain of fluorescence depends on the presence of a thiol reducing agent such as TCEP (FIG. 4), as expected from the involvement of Cys residues in protein splicing mediated by the RecA intein (Mills et al., *Proc. Natl. Acad. Sci. USA* 95: 3453-3458 (1998)). Possible premature protein splicing in the course of prolonged storage and purification of the GFP-intein fusion proteins can be completely prevented by treating the solubilized inclusion bodies with an excess 4,4'-dipyridine disulfide to block all free Cys residues. Under these conditions, the GFP-RecA intein fusion protein can be stored in 8 M urea for several months and purified by metal ion affinity chromatography without significant loss of TCEP-dependent protein splicing activity and fluorophore formation.

Figure 5:
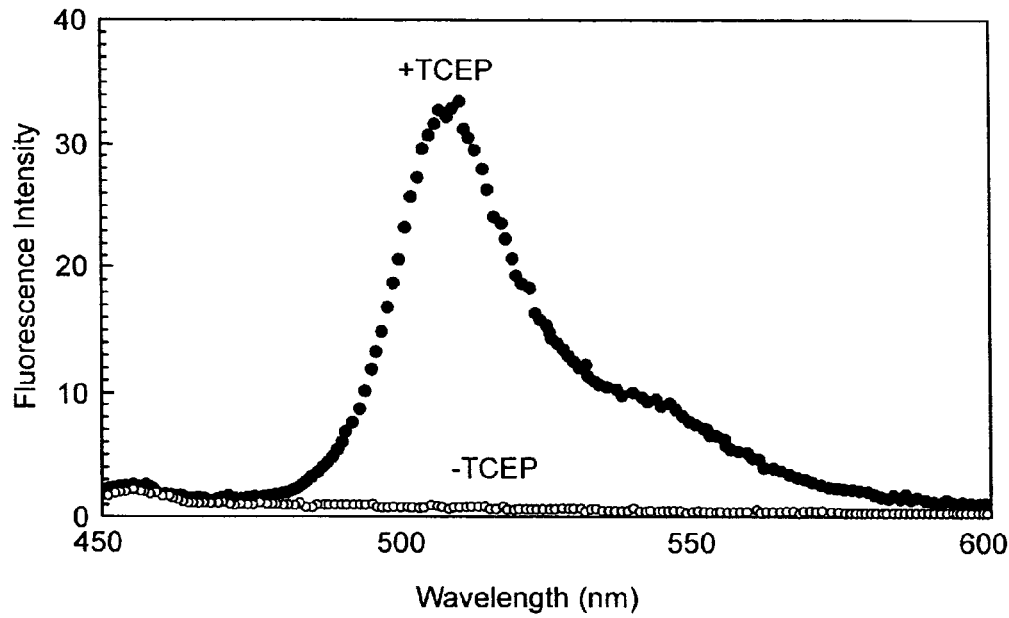
FIG. 5 shows protein splicing in vitro with the GFP-DnaB intein fusion protein. Denatured inclusion bodies of GFP-DnaB intein fusion protein were purified by MIA chromatography and renatured by dialysis into buffer in the absence or presence of TCEP. Protein splicing was allowed to proceed for 18 h at 17° C. and pH 7.0, followed by measurement of fluorescence upon excitation at 395 nm.

In a similar manner, a variant of the *M. tuberculosis* DnaB intein, in which a His-tag was inserted near the AgeI site at the C-terminus of the homing endonuclease domain, was inserted adjacent to a serine residue replacing isoleucine-129 of GFPUV. The resulting fusion protein was also expressed as inclusion bodies, from which it could be solubilized with 8 M urea and purified by metal ion affinity chromatography. The purified GFP-DnaB intein fusion protein, upon renaturation by dilution or dialysis, underwent protein splicing in the presence of TCEP to yield fluorescent GFP (FIG. 5).

2. Library Screening

Owing to the fact that the GFP-RecA intein fusion can be expressed and purified in a highly stable form and the high reproducibility of its protein splicing characteristics, this fusion protein was chosen as the basis of a highly robust HTS system. The protein splicing precursor, which is purified as the 4,4'-dithiodipyridine derivative in 8 M urea, can be refolded by dilution into phosphate buffer at pH 7.0 and retains full competence to undergo protein splicing upon activation by a thiol reducing agent such as TCEP for several hours. This allowed refolding of the precursor protein before addition of the compounds to be tested, thereby precluding possible inhibition of protein refolding. Upon addition of the compounds to be tested for inhibition, a time delay was imposed to allow for interaction of the inhibitor with the precursor protein before protein splicing was initiated by the addition of TCEP. Because the half time of the protein splicing reaction is 6 h under the experimental conditions used, it was possible to make a "0-time" fluorescence measurement to correct for possible fluorescence of the compounds to be tested. After incubation for 2.5 half-times (15 h), the fluorescence of the GFP produced as a result of protein splicing was determined. All assays were done in duplicate and positive inhibition was recorded only if both duplicate values were more than 20% below the uninhibited control values. The assay protocol is summarized below:

(1) His-tagged GFP-intein inclusion bodies are solubilized in 8 M urea, treated with 4,4'-dithiodipyridine to block —SH groups, and purified by MIA chromatography.

(2) The inclusion bodies are renatured by dilution into 30 ml of assay buffer in 384-well plates.

(3) After 30 min, 100 nl of the compounds to be tested is added by pin transfer to give a final concentration of 8.3 mg/ml. Each compound is tested in duplicate.

(4) After 30 min, 30 ml of buffer containing 2 mM TCEP is added to each sample to initiate the splicing reaction by unblocking the thiol groups.

(5) Fluorescence is measured immediately ("0 time") to correct for fluorescence of the compounds tested. Highly fluorescent compounds are eliminated from further consideration.

(6) Fluorescence is measured after incubation at room temperature for 2.5 reaction half-times (15 h). Compounds are considered hits for secondary screen if both duplicate values are >20% less than the uninhibited controls. Each plate contains at least two control columns which agree with a SD of 5%.

The library screening utilized the facilities of the Institute of Chemistry and Cell Biology (ICCB) of Harvard University. The robustness of the assay and the quality of the liquid handling equipment used assured excellent reproducibility, with a Z' factor of 0.88 [Zhang et al. (1999) J. Biomol. Screening 4, 66-73].

The compound libraries screened and the resulting positives are summarized in Table 2. The hit rates in the various libraries tested differed significantly, but the average rate of positives of 0.3% is typical for an in vitro screening system that is not unduly susceptible to perturbation.

TABLE 2

LIBRARIES SCREENED FOR PROTEIN SPLICING INHIBITORS

| Library | # of compounds | # of positives |
|---|---|---|
| Commercial Diversity Set | 5,056 | 21 (0.42%) |
| Diversity Oriented Synthesis | 16,030 | 23 (0.14%) |
| ICCB Bioactives | 489 | 4 (0.82%) |
| ChemDiv Combilab/International | 28,864 | 91 (0.32%) |
| Bionet | 6,168 | 33 (0.54%) |
| Maybridge | 16,807 | 68 (0.40%) |
| Peakdale | 3,168 | 2 (0.06%) |
| Biomol-TimTec | 8,158 | 72 (0.88%) |
| Mixed Commercial Plates | 1,254 | 9 (0.72%) |
| Total | 85,724 | 323 (0.38%) |

3. Secondary Screening

Figure 6:
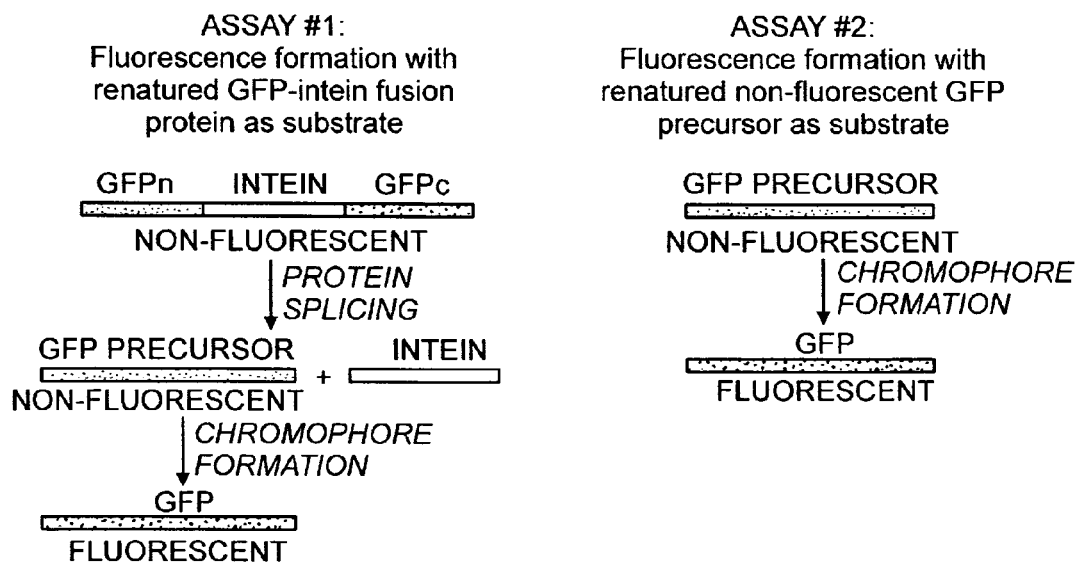
FIG. 6 represents the secondary screening of hits obtained with the primary HTS assay. Specific protein splicing inhibitors can be identified by inhibition in Assay #1 and absence of inhibition in Assay #2.

With nearly 200 positives resulting from the HTS of about 60,000 compounds at an average concentration of about 20 mM, it was important to reanalyze these hits to determine whether the inhibition seen in the original screen could also be seen at lower concentrations, and whether its target was indeed protein splicing. The latter issue arises from the fact that our HTS couples protein splicing to GFP chromophore formation. As illustrated in FIG. 6, the inhibition of fluorescence observed in our assay could arise not only from the inhibition of protein splicing, but also from the inhibition of GFP chromophore formation, the self-catalyzed oxidative rearrangement of an internal Ser-Tyr-Gly tripeptide (Niva et al., *Proc. Natl. Acad. Sci. USA* 93: 13617-13622 (1996)). These possibilities were distinguished by a secondary screen in which GFP chromophore formation was assayed separately, based on the isolation of non-fluorescent GFP inclusion bodies expressed in *E. coli* at 43° C. as the 4,4'-dithio-dipyridine adduct, involving their renaturation by dilution from 8 M urea, incubation with the compounds to be tested as inhibitors, followed by the addition of TCEP to initiate chromophore formation, which occurred with a half-time of about 2 h under our experimental conditions.

Table 3 illustrates such a secondary screen of the hits from the Bionet compound library, in which the 29 positives were assayed side-by-side for inhibition in the two assays illustrated in FIG. 6, i.e. the intein-based assay and the GFP chromophore formation assay, at a compound concentration of 5.6 mg/ml (approx. 15 mM). The results of this secondary screening clearly revealed two classes of inhibitors: those that inhibited the intein-based assay significantly more than GFP-chromophore formation and those that inhibited the two assays equally. In cases where it was possible to identify common structural scaffolds among the hits from this library, the members of a structural group generally had similar selectivity for the inhibition of protein splicing or GFP chromophore formation, indicative of clear structure-activity relationships. The fact that it was possible to define distinct SARs for protein splicing and GFP inhibitors suggested that the inhibition of these processes is not just a consequence of strong protein binding and unspecific perturbation of protein structure. About 30% of the compounds subjected to the secondary screening exhibited less that 20% inhibition in the secondary screen shown in Table 3, which was carried out a slightly lower compound concentration than the initial HTS, suggesting an IC50 less than 20 mM. The hits from each library were subjected to similar secondary screens based on the two assays outlined in FIG. 6 at two compound concentrations, at least one of which was less than that used in the original HTS. By eliminating compounds that inhibited the intein-based assay and GFP chromophore formation to similar extents and those that appeared to have an IC50 significantly above 20 M, the initial list of 196 hits was reduced to 59 confirmed hits.

TABLE 3

Secondary screen of the hits from the Bionet library, carried out at a compound concentration of 5.6 μg/ml. Assays #1 (Intein) and #2 (GFP) (see FIG. 6) were run in duplicate on all hits. The compounds marked * primarily inhibit protein splicing, those marked ** inhibit protein splicing and GFP chromophore formation to similar extents. The last column indicates recurring structure scaffolds in the library.

| Plate | Well | | Intein 1 | Intein 2 | 11% inh | 12% inh | GFP1 | GFP2 | G1 % inh | G2 % inh | Structure type |
|---|---|---|---|---|---|---|---|---|---|---|---|
| PL-0569 | L020 | * | 44529 | 44624 | 59 | 59 | 71493 | 75291 | 21 | 11 | F |
| PL-0569 | N014 | * | 53264 | 50321 | 51 | 54 | 72728 | 74627 | 19 | 17 | F |
| PL-0569 | N022 | * | 69974 | 74816 | 34 | 30 | 84501 | 80228 | 5 | 10 | F |
| PL-0569 | P008 | * | 73677 | 73107 | 31 | 31 | 87634 | 92097 | 2 | −4 | F |
| PL-0569 | P010 | * | 62948 | 64088 | 41 | 40 | 75576 | 86875 | 16 | 3 | F |
| PL-0569 | P012 | * | 42535 | 43959 | 61 | 60 | 73772 | 70639 | 18 | 22 | F |
| PL-0570 | P015 | * | 46333 | 48801 | 58 | 55 | 71114 | 79184 | 21 | 12 | G |
| PL-0570 | P017 | * | 67316 | 65512 | 37 | 39 | 85735 | 64942 | 4 | 28 | G |
| PL-0570 | P019 | * | 33895 | 36838 | 70 | 67 | 74627 | 76620 | 17 | 15 | G |
| PL-0571 | B013 | | 93141 | 94470 | 12 | 10 | 98553 | 100547 | −11 | −13 | G |
| PL-0571 | N022 | | 85166 | 91337 | 20 | 13 | 78804 | 80703 | 12 | 10 | H |
| PL-0571 | P006 | | 93521 | 91147 | 11 | 14 | 84216 | 84121 | 6 | 6 | H |
| PL-0571 | P016 | * | 51175 | 53834 | 53 | 50 | 79279 | 76905 | 12 | 14 | H |
| PL-0574 | E003 | | 73582 | 74816 | 31 | 30 | 75006 | 77285 | 17 | 14 | I |
| PL-0574 | E005 | ** | 34560 | 36364 | 69 | 67 | 54973 | 50795 | 40 | 45 | I |
| PL-0574 | J003 | * | 65987 | 57726 | 38 | 46 | 91907 | 80988 | −3 | 10 | K |
| PL-0574 | J009 | * | 26299 | 29433 | 77 | 74 | 68930 | 67221 | 24 | 26 | K |
| PL-0576 | E009 | * | 49751 | 52599 | 54 | 51 | 64562 | 67221 | 29 | 26 | G |
| PL-0576 | E015 | | 88109 | 88963 | 17 | 16 | 84311 | 81368 | 6 | 9 | G |
| PL-0576 | G004 | ** | 75101 | 78899 | 29 | 26 | 70259 | 64657 | 22 | 29 | |
| PL-0576 | I019 | * | 41301 | 50605 | 63 | 53 | 64372 | 62474 | 29 | 31 | G |
| PL-0576 | O013 | * | 22597 | 24590 | 61 | 79 | 66041 | 67411 | 26 | 26 | |
| PL-0577 | C020 | | 101306 | 100547 | 4 | 4 | 90672 | 85071 | −2 | 5 | |
| PL-0577 | E022 | | 99217 | 91432 | 6 | 13 | 95230 | 92097 | −7 | −4 | |
| PL-0578 | L017 | | 133872 | 130454 | −28 | −25 | 93141 | 85071 | −5 | 5 | |
| PL-0581 | O021 | * | 29717 | 28768 | 74 | 75 | 71778 | 69310 | 20 | 23 | |
| PL-0581 | P005 | | 106148 | 106433 | −1 | −1 | 91337 | 94375 | −3 | −6 | |
| PL-0582 | I008 | ** | 16045 | 15760 | 87 | 88 | 29528 | 31616 | 70 | 68 | J |
| PL-0582 | I016 | ** | 11298 | 7975 | 92 | 95 | 18609 | 16045 | 83 | 86 | J |

4. Data Analysis

The positives that were confirmed by our secondary screening were subjected preliminary evaluation of drug-likeness, to a large extent relying on the criteria formulated by Lipinski (Lipinski et al., *Adv. Drug Delivery Rev.* 46: 3-26 (2001)). This preliminary assessment made use of the Osiris Property Explorer (http://www.organic-chemistry.org), a compound registration system made available for public use by Actelion, a Swiss pharmaceutical company. Besides computing molecular weight, ClogP and solubility (logs) from the structure of a compound, this program compares substructure fragments with those of traded drugs to assess drug-likeness. For 80% of traded drugs, the drug-likeness score has a positive value and very few drugs have a score <−5, whereas most of the commercially available Fluka chemicals have a negative score. Substructure analysis was also used for toxicity risk assessment (mutagenicity, tumorigenicity, irritation, and reproductive effects). All these parameters are then combined with the Lipinski criteria of Mr <500 and ClogP <5 and estimated solubility to yield a drug-score. The results of this analysis, which are summarized in Table 4, indicate that about 20% of our confirmed positives have a high drug score and are thus candidates for lead optimization. The structures of these high-ranking positives and those of lower-ranking related compounds may be analyzed to define the structural scaffolds that promote inhibition of intein function. Together with quantitative information provided by IC50, this will provide insights into SAR and pave the way to lead optimization.

TABLE 4

Analysis of the drug-like properties of the protein splicing inhibitors identified by HTS and verified by secondary screening, using the Osiris Property Explorer (http://www.organic-chemistry.org) as described in the text.

| Cpd. # | $M_r$ | ClogP | log Sol. | Muta-genic | Tumor-igenic | Irri-tant | Repro-ductive effect | Drug-likeness | Drug-score | Library | Form. Type | RecA intein IC50 (μM) | DnaB intein IC50 (μM) | BCG MIC (μg/ml) | Mtu H37Rv MIC (μg/ml) |
|---|---|---|---|---|---|---|---|---|---|---|---|---|---|---|---|
| 1 | 366 | 5.00 | −4.69 | N | N | N | N | 2.30 | 0.50 | MixCom | 8 | 5 | 30 | — | — |
| 2 | 388 | 3.26 | −3.35 | N | N | N | N | −0.95 | 0.49 | Maybridge | | 8 | 13 | — | — |
| 3 | 380 | −0.07 | −3.64 | N | N | N | N | −10.90 | 0.40 | Maybridge | | 10 | 17 | 20 | 20[a] |
| 4 | 314 | 4.58 | −5.31 | N | N | N | N | −5.34 | 0.27 | Maybridge | | 5 | 5 | — | — |
| 6 | 381 | 1.66 | −5.42 | N | N | N | N | −3.18 | 0.32 | Bionet | 3 | 4 | 13 | — | [b] |
| 7 | 371 | 2.18 | −6.06 | N | N | N | N | −1.19 | 0.34 | Bionet | 3 | 4 | 6 | — | [c] |
| 8 | 386 | 3.92 | −5.01 | N | N | N | N | −3.04 | 0.31 | Bionet | | 5 | 5 | — | — |
| 9 | 385 | 0.57 | −5.08 | N | Med | Med | N | 0.16 | 0.33 | Bionet | 4 | 10 | 7 | 5 | 5[d] |
| 10 | 380 | 1.02 | −5.08 | N | N | N | N | 0.20 | 0.51 | Bionet | 3 | 8 | 7 | — | — |
| 11 | 356 | −2.29 | −4.17 | N | N | N | N | 2.05 | 0.75 | Bionet | 3 | 4 | 8 | 5 | 5 |
| 12 | 398 | 1.08 | −5.39 | N | N | N | N | 0.69 | 0.51 | Bionet | 3 | 3 | 5 | 20 | 10 |
| 13 | 361 | 3.11 | −3.66 | Hi | N | N | N | 1.35 | 0.42 | Bionet | | 4 | 8 | 20 | 10 |
| 17 | 466 | 2.83 | −5.33 | N | N | Med | N | −3.20 | 0.20 | MixCom | | 20 | 15 | — | — |
| 21 | 253 | 2.71 | −4.58 | N | N | Med | N | −6.40 | 0.30 | Maybridge | 7 | 8 | 15 | — | — |
| 22 | 302 | 3.14 | −4.79 | N | N | Med | N | −4.01 | 0.28 | Maybridge | | 3 | 5 | — | 20 |
| 23 | 317 | 2.23 | −5.35 | N | N | N | N | 1.37 | 0.59 | Maybridge | 3 | 3 | <5 | — | — |
| 24 | 174 | 2.35 | −3.62 | Hi | N | Med | N | −7.15 | 0.21 | Maybridge | | 11 | 12 | — | 5 |
| 27 | 425 | 4.45 | −5.66 | N | N | N | Hi | −2.75 | 0.15 | Maybridge | | 2 | <5 | — | — |
| 29 | 341 | 4.79 | −5.37 | N | N | N | N | −3.92 | 0.26 | Maybridge | | 30 | <5 | — | — |
| 30 | 392 | 3.59 | −5.13 | N | N | Med | Med | −12.43 | 0.19 | Maybridge | 6 | 5 | <5 | 20 | — |
| 31 | 251 | 0.42 | −2.04 | N | N | N | N | −5.80 | 0.48 | Maybridge | 6 | 5 | 5 | 6 | 10 |
| 33 | 381 | 3.66 | −6.27 | N | N | N | N | −9.89 | 0.25 | Maybridge | 6 | 4 | <5 | — | — |
| 35 | 370 | 1.72 | −5.36 | N | N | N | N | −11.90 | 0.32 | Bionet | 3 | 1 | <<5 | 20 | — |
| 36 | 384 | 1.66 | −5.82 | N | N | N | N | −11.00 | 0.29 | Bionet | 3 | 5 | 5 | — | — |
| 37 | 361 | 4.07 | −5.55 | N | N | Med | N | −5.90 | 0.20 | ChemDiv | 7 | 5 | <5 | — | — |
| 38 | 367 | 3.39 | −4.72 | N | Med | Med | N | −7.62 | 0.21 | MixCom | | 0.8 | <5 | — | — |
| 39 | 351 | 4.32 | −5.00 | N | N | N | N | −7.70 | 0.30 | Bionet | 5 | 0.8 | <5 | — | — |
| 40 | 399 | 4.52 | −5.78 | Hi | N | N | N | −6.38 | 0.14 | Bionet | 2 | 5 | <5 | — | — |
| 41 | 395 | 3.89 | −4.50 | N | N | N | N | −6.10 | 0.30 | Bionet | 5 | 2 | <5 | — | — |
| 43 | 399 | 0.88 | −5.42 | N | Med | Med | N | −1.12 | 0.24 | Bionet | 4 | 3 | <5 | 1 | 2.5 |
| 44 | 334 | 3.40 | −3.79 | N | N | N | N | −8.19 | 0.38 | Bionet | | 5 | <<5 | — | — |
| 45 | 347 | 3.46 | −4.59 | N | N | N | N | −8.39 | 0.34 | Bionet | | 5 | <5 | 5 | 2.5 |
| 51 | 561 | 4.43 | −5.53 | Hi | N | N | N | −2.46 | 0.12 | ChemDiv | | 2 | <5 | — | — |
| 53 | 472 | 3.10 | −6.20 | Hi | N | Med | Med | −6.50 | 0.10 | ChemDiv | 1 | 1 | <<5 | ~20 | — |
| 54 | 375 | 5.49 | −5.95 | N | N | N | N | −7.45 | 0.20 | ChemDiv | | 6 | 11 | 5 | 10 |
| 55 | 384 | 4.54 | −5.08 | N | N | N | N | −14.00 | 0.21 | ChemDiv | 1 | 15 | 7 | 5 | 20 |
| 56 | 373 | 2.84 | −4.23 | N | N | N | N | −3.14 | 0.38 | ChemDiv | 9 | <35* | 10* | — | — |
| 57 | 354 | 4.19 | −5.28 | N | N | N | N | −8.25 | 0.28 | Bionet | | <5 | 5 | — | — |
| 58 | 385 | 4.66 | −6.12 | Hi | N | N | N | −6.15 | 0.13 | Bionet | 2 | <5 | 7 | — | — |
| 59 | 385 | 4.66 | −6.12 | Hi | N | N | N | −6.70 | 0.13 | Bionet | 2 | <5 | <5 | — | — |
| 62 | 385 | 4.66 | −6.12 | Hi | N | N | N | −5.25 | 0.13 | Maybridge | 2 | <5 | 5 | — | — |
| 64 | 377 | 4.82 | −6.69 | Med | N | N | N | −1.61 | 0.16 | Maybridge | 1 | 6 | <5 | — | — |
| 65 | 427 | 6.11 | −6.92 | Med | N | N | N | −14.10 | 0.12 | Maybridge | 1 | <<5 | <<5 | — | — |
| 66 | 414 | 4.77 | −6.21 | Med | N | N | N | −15.00 | 0.20 | Maybridge | 1 | <<5 | <<5 | >20 | — |
| 67 | 365 | 3.77 | −5.63 | N | N | N | N | −6.42 | 0.27 | Maybridge | | <5 | 5 | — | — |
| 68 | 271 | 3.70 | −4.50 | N | N | N | N | −1.40 | 0.42 | Maybridge | | 8 | 9 | — | — |
| 69 | 381 | 3.64 | −3.65 | N | N | N | N | −6.87 | 0.36 | Maybridge | 8 | <5 | 37 | — | — |
| 70 | 346 | 4.08 | −4.32 | Med | N | N | N | −7.41 | 0.27 | Maybridge | | 12 | 5 | — | — |
| 71 | 446 | 5.68 | −5.63 | N | N | N | N | −14.20 | 0.19 | Maybridge | 9 | <<5 | <<5 | 10 | 10 |
| 72 | 406 | 4.90 | −4.88 | N | N | N | N | −15.40 | 0.26 | Maybridge | 9 | <<5 | <<5 | 10 | 10 |
| 74 | 198 | 1.85 | −3.13 | N | N | N | N | −1.70 | 0.52 | TimTec | | <5 | nd | — | — |
| 75 | 408 | 3.52 | −5.07 | N | N | N | N | −6.46 | 0.29 | TimTec | 10 | <5 | nd | — | — |
| 76 | 267 | 3.19 | −3.60 | Med | N | N | N | −2.78 | 0.34 | TimTec | 10 | 8 | nd | — | — |
| 77 | 309 | 3.51 | −4.62 | N | N | N | N | −2.13 | 0.38 | TimTec | 10 | 30 | nd | — | — |
| 78 | 325 | 4.25 | −4.95 | N | N | N | N | −1.53 | 0.35 | TimTec | 10 | 13 | nd | — | — |
| 80 | 369 | −0.29 | −2.18 | N | N | N | N | 1.32 | 0.83 | TimTec | | 8 | nd | — | — |
| 81 | 380 | 4.46 | −3.93 | N | N | Med | N | −6.34 | 0.26 | TimTec | | 12 | nd | — | — |

TABLE 4-continued

Analysis of the drug-like properties of the protein splicing inhibitors identified by HTS and verified by secondary screening, using the Osiris Property Explorer (http://www.organic-chemistry.org) as described in the text.

| Cpd. # | $M_r$ | ClogP | log Sol. | Muta-genic | Tumor-igenic | Irri-tant | Repro-ductive effect | Drug-likeness | Drug-score | Library | Form. Type | RecA intein IC50 (µM) | DnaB intein IC50 (µM) | BCG MIC (µg/ml) | Mtu H37Rv MIC (µg/ml) |
|---|---|---|---|---|---|---|---|---|---|---|---|---|---|---|---|
| 82 | 295 | 4.19 | −3.90 | N | N | N | N | −0.46 | 0.50 | TimTec | | 8 | nd | — | — |
| 83 | 273 | 1.86 | −4.08 | N | Med | N | N | −1.95 | 0.36 | TimTec | | 7 | nd | — | 10 |

Footnotes:
*Compound fluorescence interfered with activity measurements
[a]37%, [b]32%, [c]96%, [d]100% inhibition of Alamar Blue reduction at 6.25 µg/ml, as measured by TAACF.
Abbreviations: cpd., compound; nd, not determined; sol., solubility; form. type, formula type as defined in Table 1

5. Determination of the IC50 for the Inhibition of the DnaB and the RecA Inteins The positives that were confirmed by our secondary screening were subjected preliminary evaluation of drug-likeness, to a large extent relying on the criteria formulated by Lipinski (Lipinski et al., Adv. Drug Delivery Rev. 46: 3-26 (2001)). This preliminary assessment made use of the Osiris Property Explorer (www.organic-chemistry.org), a compound registration system made available for public use by Actelion, a Swiss pharmaceutical company. Besides computing molecular weight, ClogP and solubility (logS) from the structure of a compound, this program compares substructure fragments with those of traded drugs to assess drug-likeness. For 80% of traded drugs, the drug-likeness score has a positive value and very few drugs have a score <−5, whereas most of the commercially available Fluka chemicals have a negative score. Substructure analysis was also used for toxicity risk assessment (mutagenicity, tumorigenicity, irritation, and reproductive effects). All these parameters are then combined with the Lipinski criteria of Mr <500 and ClogP <5 and estimated solubility to yield a drug-score. The results of this analysis, which are summarized in Table 4, indicate that about 20% of our confirmed positives have a high drug score and are thus candidates for lead optimization. The structures of these high-ranking positives and those of lower-ranking related compounds may be analyzed to define the structural scaffolds that promote inhibition of intein function. Together with quantitative information provided by IC50, this will provide insights into SAR and pave the way to lead optimization.

Figure 7A:
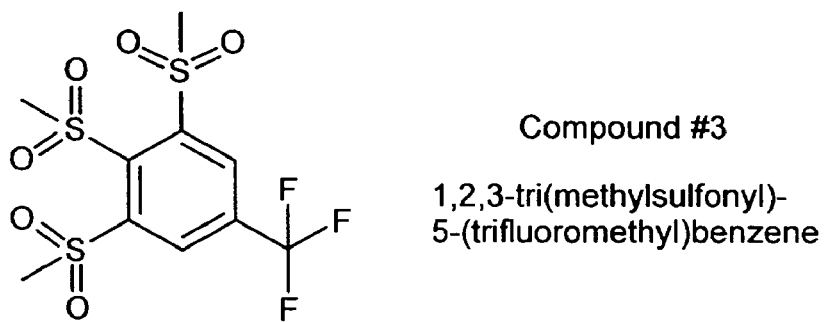
FIG. 7 shows determination of the IC50 of ICCB 29865 (Compound #3) in an in vitro assay of protein splicing. (A) Structure of ICCB 29865. (B) Effect of ICCB 29865 on the fluorometric assay of protein splicing mediated by the RecA and DnaB inteins inserted at position 129 of GFP, as on GFP chromophore formation. (C) Effect of ICCB 29865 on protein splicing mediated by the RecA intein, measured by the conversion of the precursor protein to spliced products by SDSPAGE.
Figure 7B:
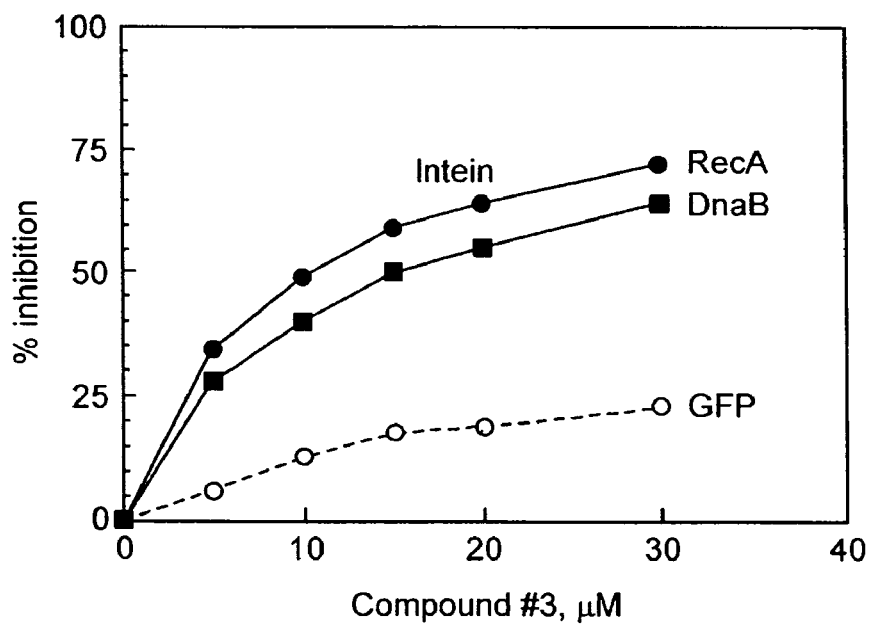
Figure 7C:
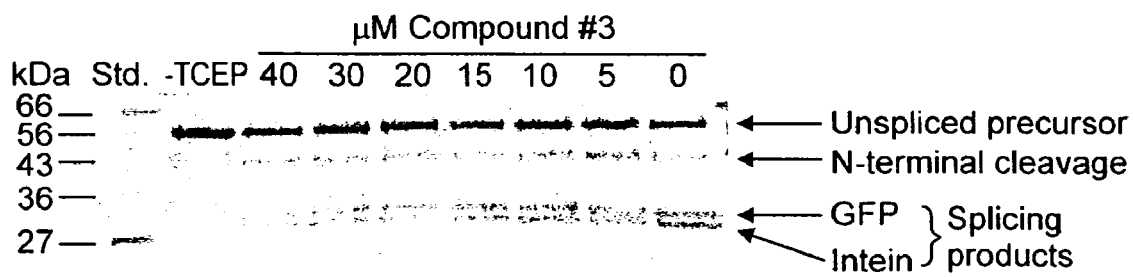

Although ICCB 29865, the compound used in this example, lacks drug-like properties and is therefore not a lead candidate, the results in FIG. 7 represent an important proof-of-concept by demonstrating that it is possible to find compounds that inhibit protein splicing by the M. tuberculosis RecA and DnaB intein to similar extents (IC50>>10 mM). Inhibition of protein splicing was also followed by SDS-PAGE, independent of GFP fluorescence, to verify that the target of inhibition is indeed protein splicing.

A selected subgroup of 59 compounds, which were chosen on the basis of specificity as indicated by secondary screening and relatively high estimated drug scores (see Table 4), were purchased from the suppliers and tested by in vitro assay for the inhibition of protein splicing at concentrations ranging from 5 to 40 µM. Results are shown in Table 4. Although the quantitative inhibition measurements were made using fluorescent GFP-linked protein splicing system, they were confirmed in every case by a direct protein splicing assay that measured the conversion of the precursor protein to the protein splicing products by SDS-PAGE (see FIG. 7).

The invention claimed is:

1. A method for inhibiting protein splicing, the method comprising contacting an intein-containing protein with one or more small-molecule inhibitors of protein splicing, the inhibitors being organic compounds which interact specifically with the intein-containing protein and wherein the inhibitors are selected from the group consisting of:

Formula 11 (Compound #1)

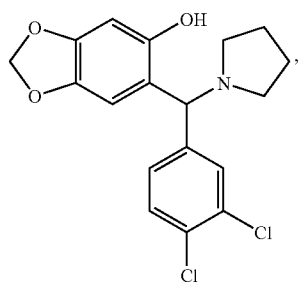

Formula 12 (Compound #2)

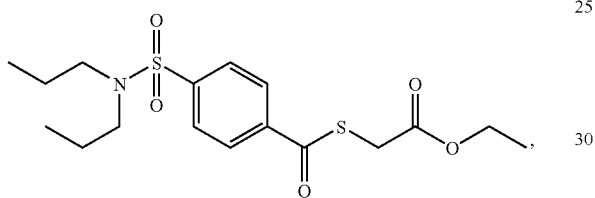

Formula 13 (Compound #3)

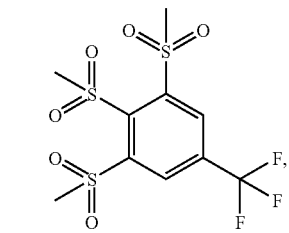

Formula 14 (Compound #4)

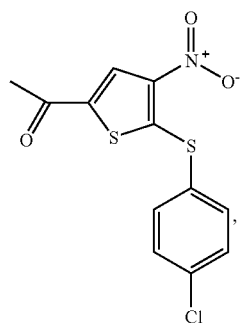

Formula 15 (Compound #6)

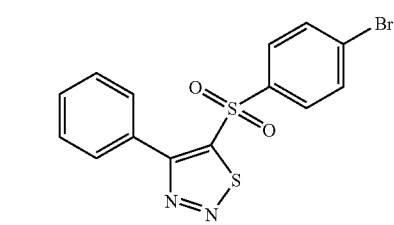

-continued

Formula 16 (Compound #7)

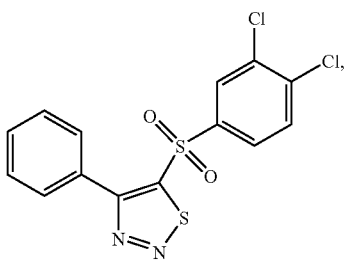

Formula 17 (Compound #8)

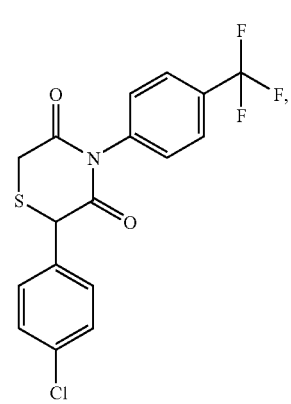

Formula 18 (Compound #9)

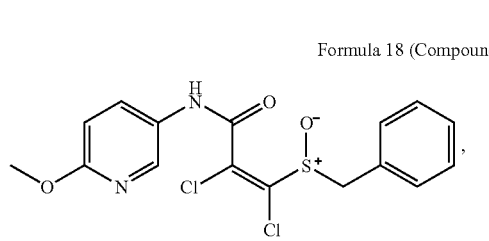

Formula 19 (Compound #10)

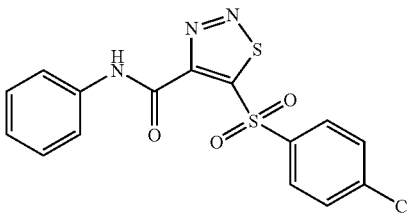

Formula 20 (Compound #11)

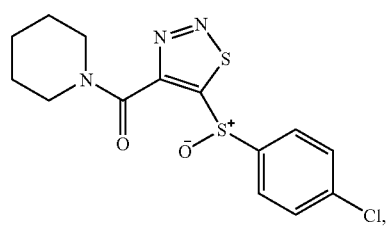

-continued
Formula 21 (Compound #12)
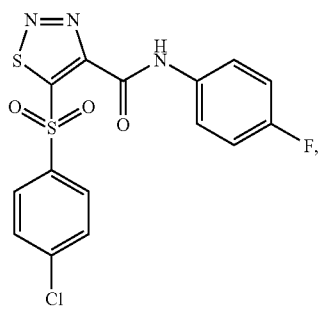
Formula 22 (Compound #13)
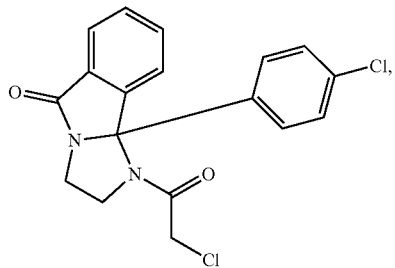
Formula 23 (Compound #17)
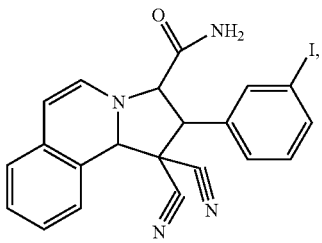
Formula 24 (Compound #21)
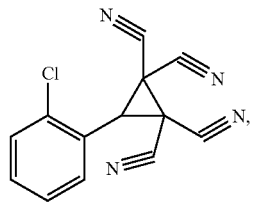
Formula 25 (Compound #22)
Formula 26 (Compound #23)
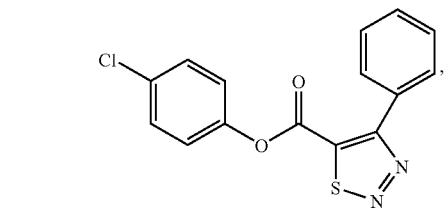
Formula 27 (Compound #24)
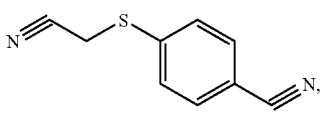
-continued
Formula 28 (Compound #27)
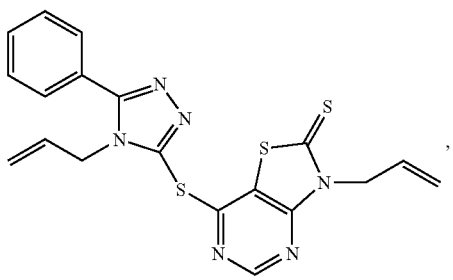
Formula 29 (Compound #29)
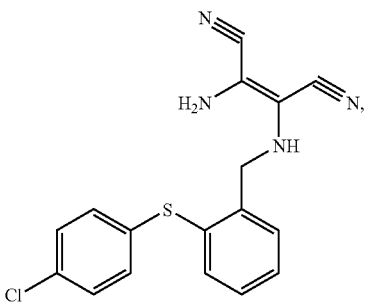
Formula 30 (Compound #30)
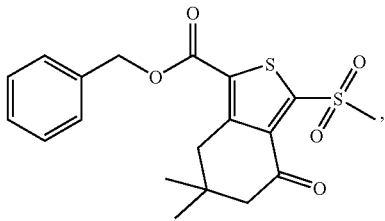
Formula 31 (Compound #31)
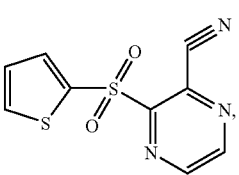
Formula 32 (Compound #33)
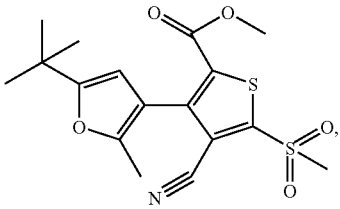
Formula 33 (Compound #35)
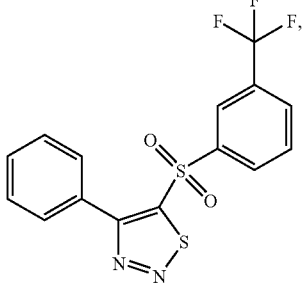

Formula 34 (Compound #36)
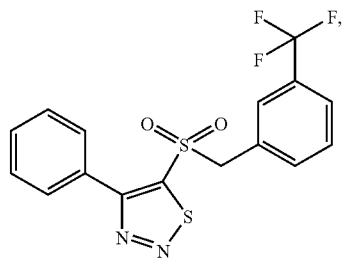
Formula 35 (Compound #37)
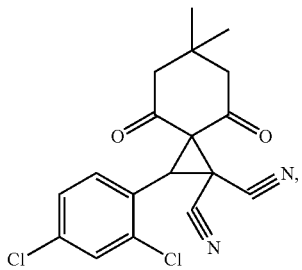
Formula 36 (Compound #38)
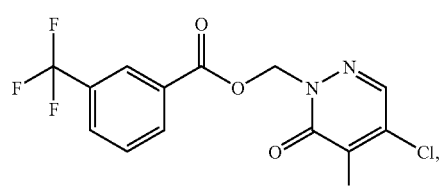
Formula 37 (Compound #39)
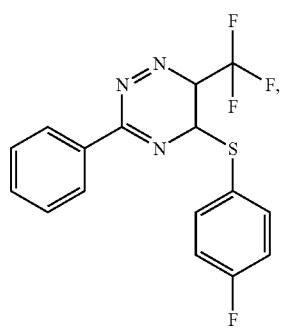
Formula 38 (Compound #40)
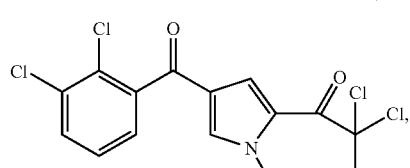
Formula 39 (Compound #41)
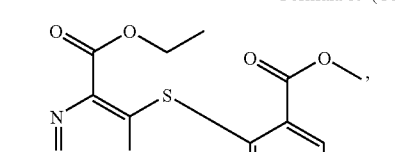
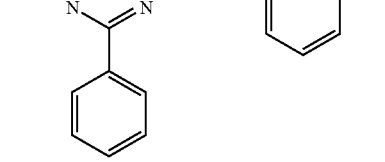
Formula 40 (Compound #43)
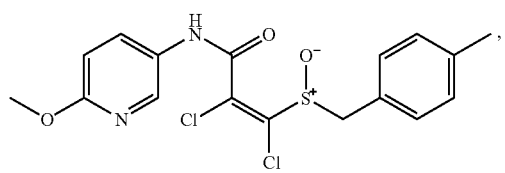
Formula 41 (Compound #44)
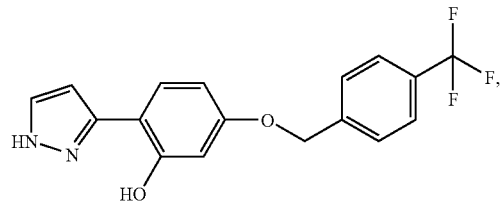
Formula 42 (Compound #45)
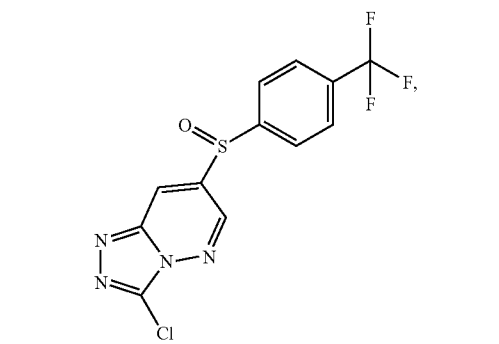
Formula 43 (Compound #51)
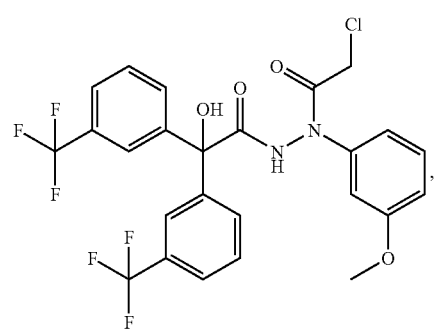
Formula 44 (Compound #53)
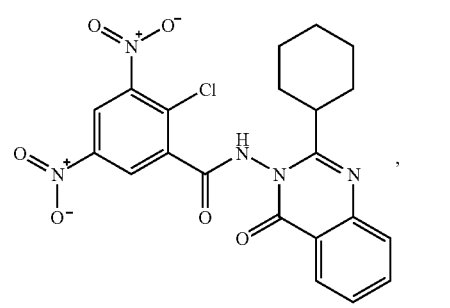

-continued
Formula 45 (Compound #54)
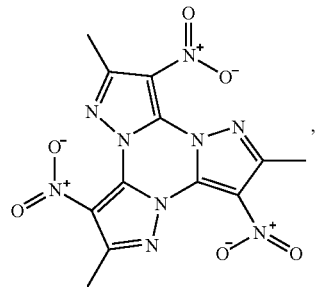
Formula 46 (Compound #55)
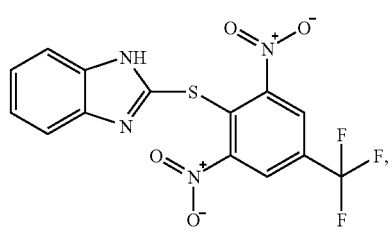
Formula 47 (Compound #56)
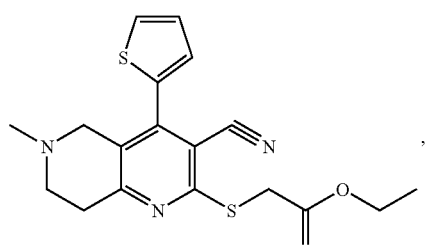
Formula 48 (Compound #57)
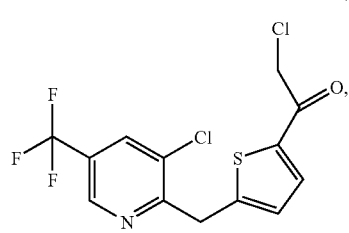
Formula 49 (Compound #58)
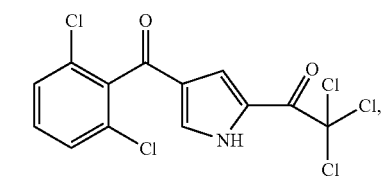
Formula 50 (Compound #59)
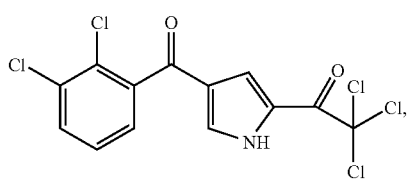
-continued
Formula 51 (Compound #62)
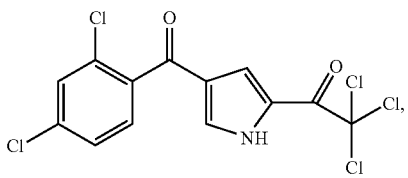
Formula 52 (Compound #64)
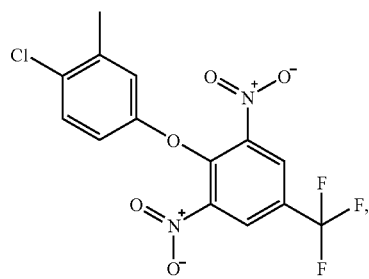
Formula 53 (Compound #65)
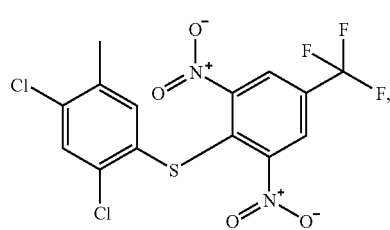
Formula 54 (Compound #66)
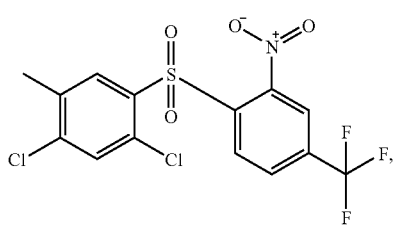
Formula 55 (Compound #67)
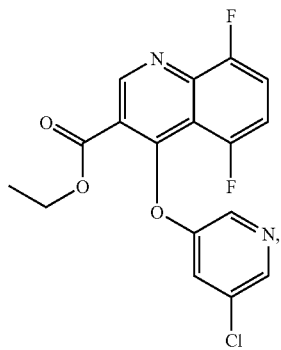
Formula 56 (Compound #68)
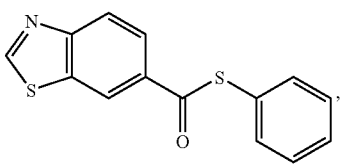

-continued
Formula 57 (Compound #69)
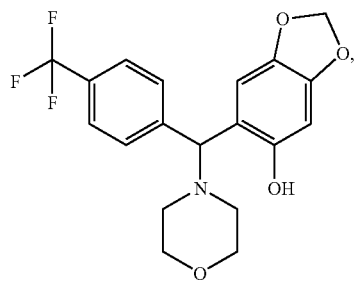
Formula 58 (Compound #70)
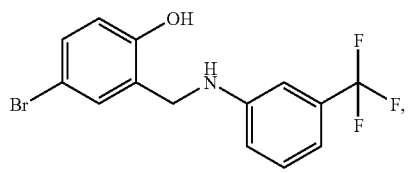
Formula 59 (Compound #71)
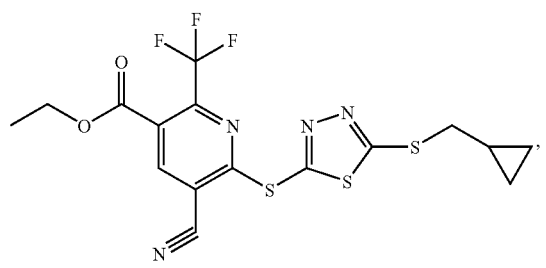
Formula 60 (Compound #72)
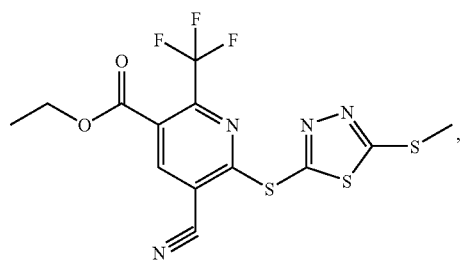
Formula 61 (Compound #74)
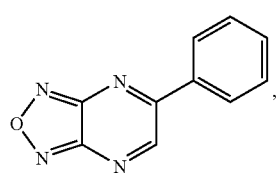
-continued
Formula 62 (Compound #75)
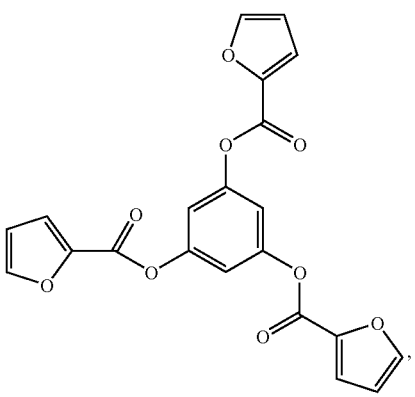
Formula 63 (Compound #76)
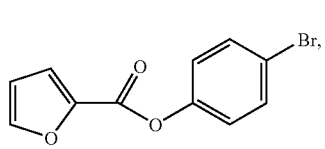
Formula 64 (Compound #77)
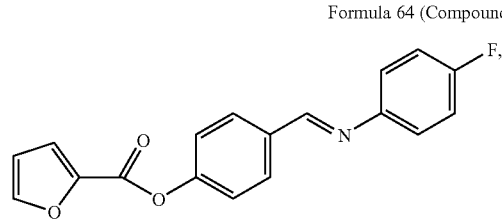
Formula 65 (Compound #78)
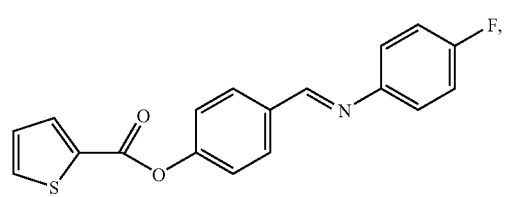
Formula 66 (Compound #80)
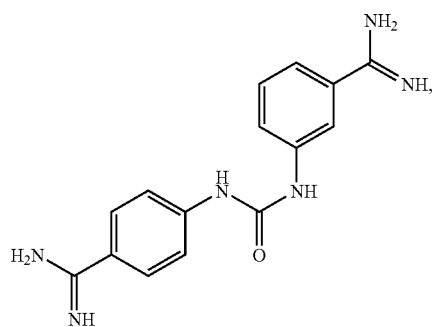
Formula 67 (Compound #81)
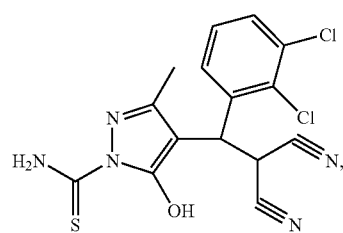

-continued

Formula 68 (Compound #82)

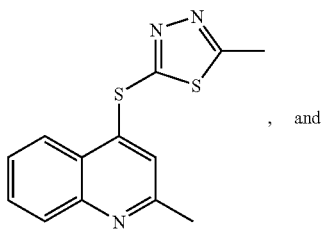
, and

Formula 69 (Compound #83)

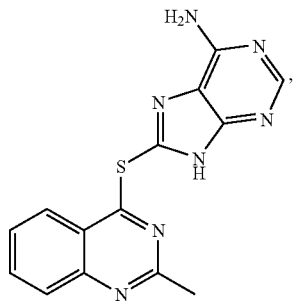

or pharmaceutical salts thereof.

2. The method of claim 1 wherein the contacting step is carried out in vitro.

3. The method of claim 1 wherein the contacting step is carried out in vivo.

4. The method of claim 1 wherein the protein containing the intein is selected from the group consisting of enzymes, toxins, cytokines, transcription factors, and growth factors.

5. The method of claim 1 wherein the contacting occurs during purification of the protein.

6. The method of claim 1 wherein the contacting occurs during synthesis of the protein.

7. A method for activating the function of a protein, the method comprising:

a) contacting a protein which is interrupted by an intein wherein the intein renders the protein inactive, with a small-molecule inhibitor of protein splicing at an effective concentration, the inhibitor of protein splicing being selected from the group consisting of the compounds of:

Formula 11 (Compound #1)

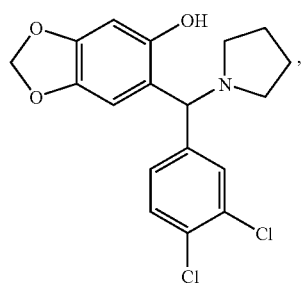

Formula 12 (Compound #2)

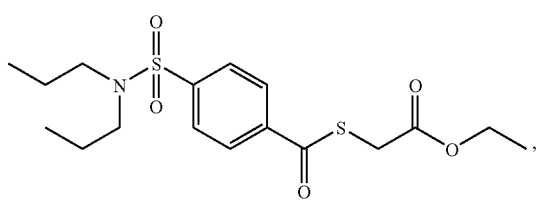

-continued

Formula 13 (Compound #3)

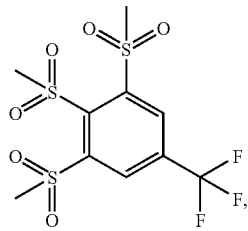

Formula 14 (Compound #4)

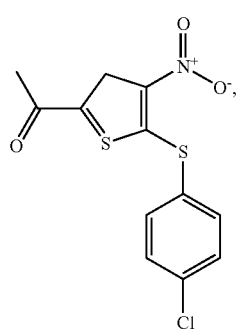

Formula 15 (Compound #6)

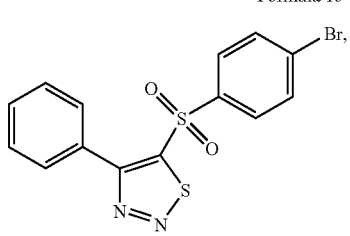

Formula 16 (Compound #7)

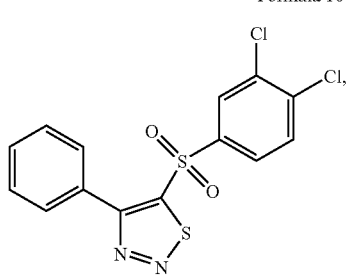

Formula 17 (Compound #8)

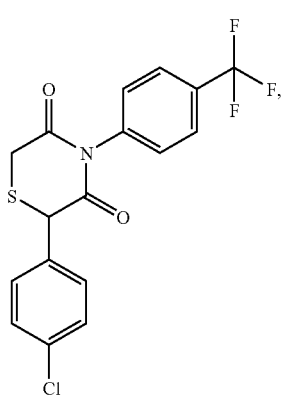

-continued
Formula 18 (Compound #9)
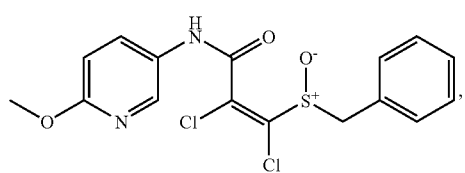
Formula 19 (Compound #10)
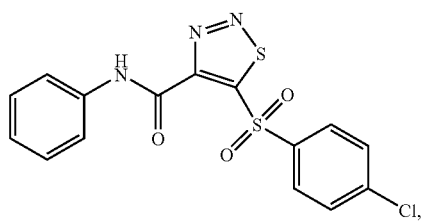
Formula 20 (Compound #11)
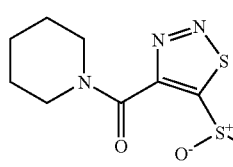
Formula 21 (Compound #12)
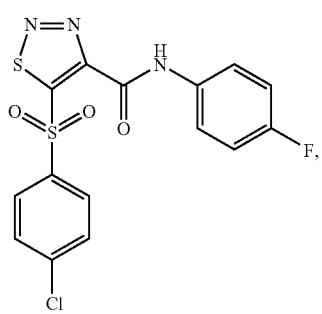
Formula 22 (Compound #13)
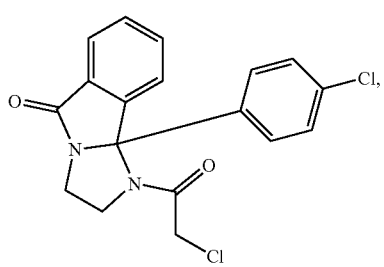
Formula 23 (Compound #17)
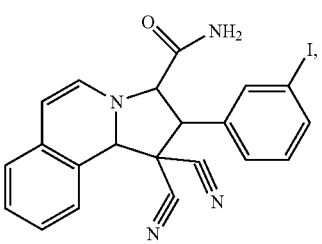
-continued
Formula 24 (Compound #21)
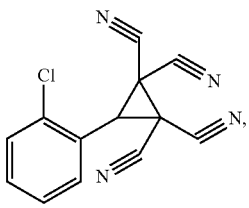
Formula 25 (Compound #22)
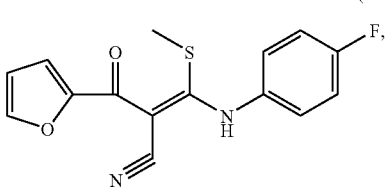
Formula 26 (Compound #23)
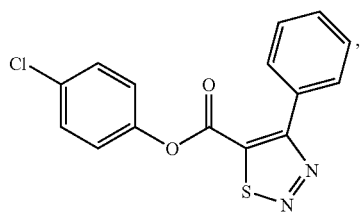
Formula 27 (Compound #24)
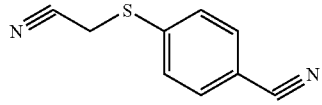
Formula 28 (Compound #27)
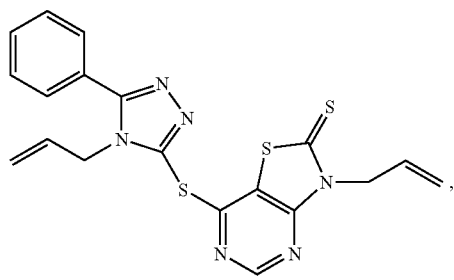
Formula 29 (Compound #29)
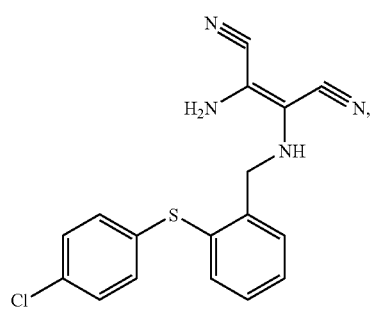

-continued
Formula 30 (Compound #30)
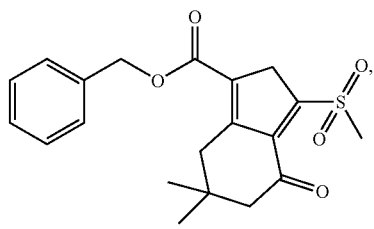
Formula 31 (Compound #31)
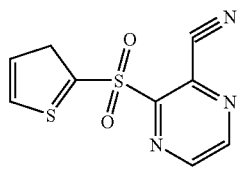
Formula 32 (Compound #33)
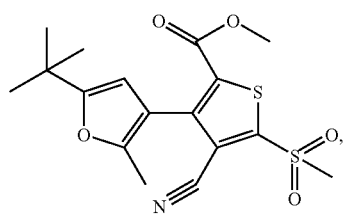
Formula 33 (Compound #35)
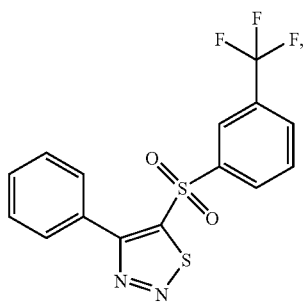
Formula 34 (Compound #36)
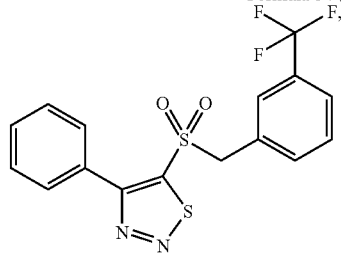
Formula 35 (Compound #37)
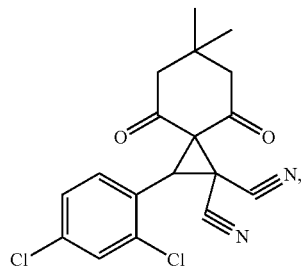
-continued
Formula 36 (Compound #38)
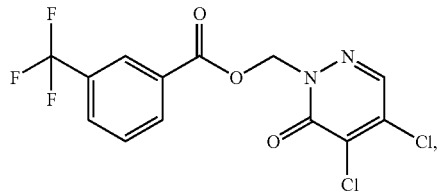
Formula 37 (Compound #39)
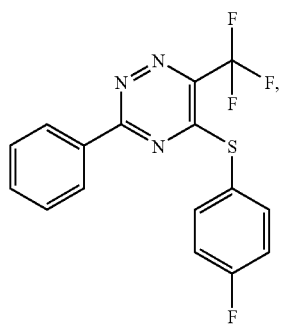
Formula 38 (Compound #40)
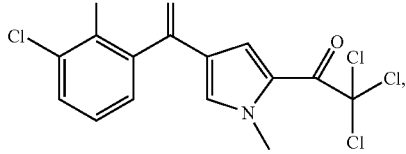
Formula 39 (Compound #41)
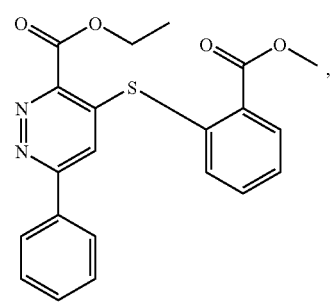
Formula 40 (Compound #43)
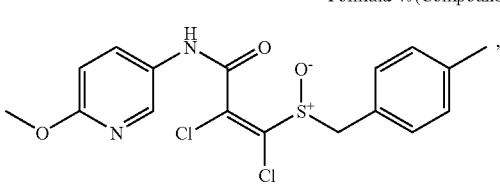
Formula 41 (Compound #44)
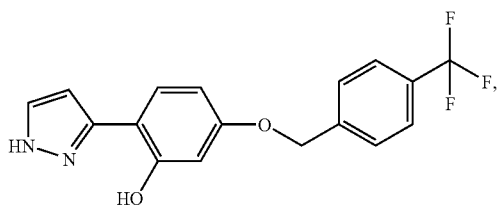

-continued

Formula 42 (Compound #45)

Formula 43 (Compound #51)

Formula 44 (Compound #53)

Formula 45 (Compound #54)

Formula 46 (Compound #55)

-continued

Formula 57 (Compound #56)

Formula 48 (Compound #57)

Formula 49 (Compound #58)

Formula 50 (Compound #59)

Formula 51 (Compound #62)

Formula 52 (Compound #64)

-continued
Formula 53 (Compound #65)
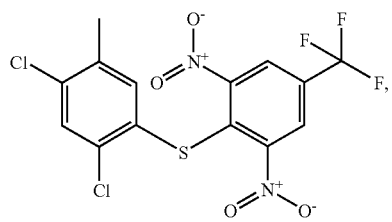
Formula 54 (Compound #66)
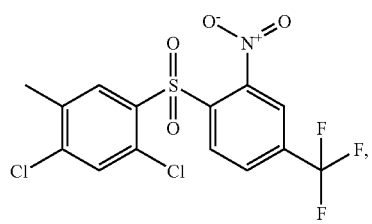
Formula 55 (Compound #67)
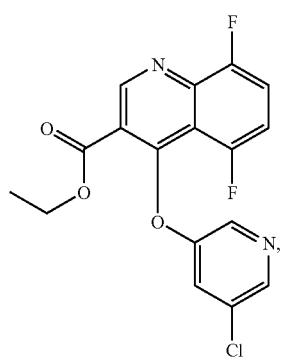
Formula 56 (Compound #68)
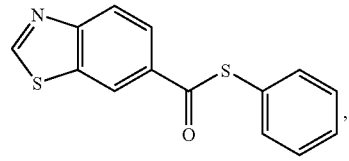
Formula 57 (Compound #69)
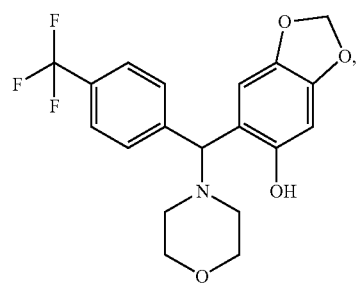
Formula 58 (Compound #70)
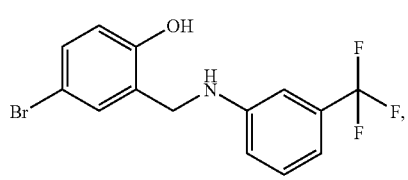
-continued
Formula 59 (Compound #71)
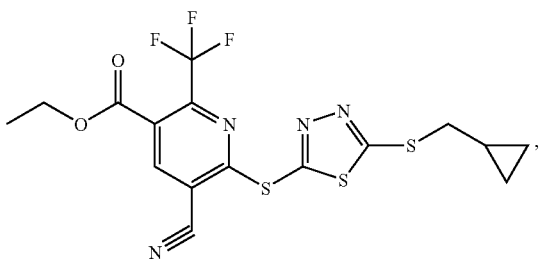
Formula 60 (Compound #72)
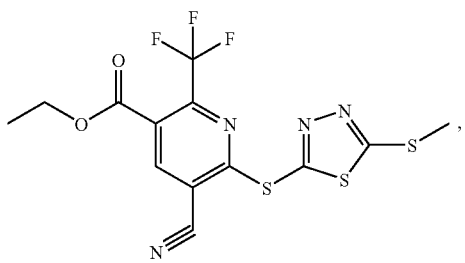
Formula 61 (Compound #74)
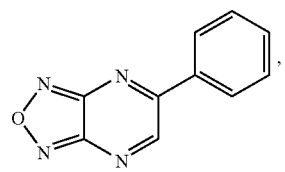
Formula 62 (Compound #75)
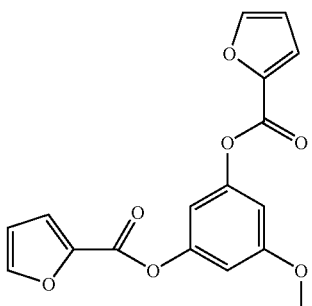
Formula 63 (Compound #79)
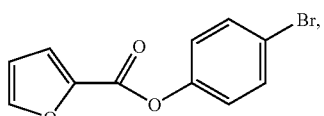
Formula 64 (Compound #77)
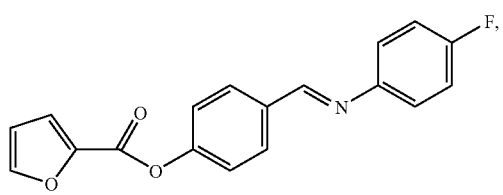

-continued

Formula 65 (Compound #78)

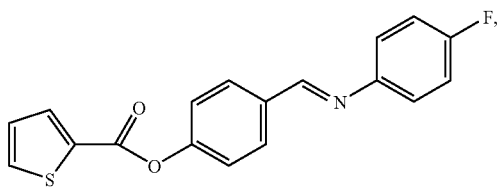

Formula 66 (Compound #80)

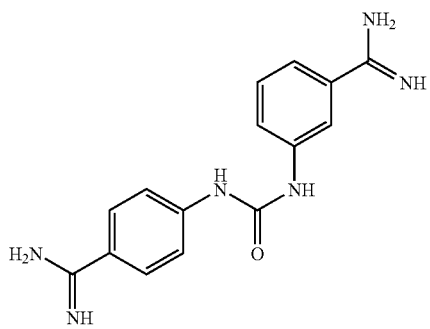

Formula 67 (Compound #81)

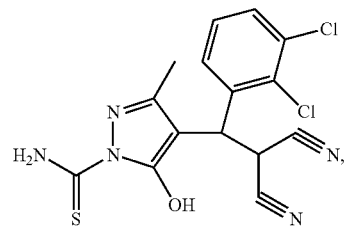

Formula 68 (Compound #82)

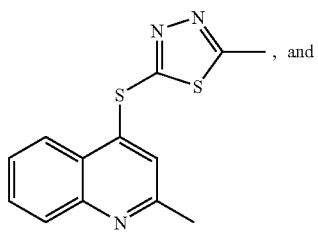, and

Formula 69 (Compound #83)

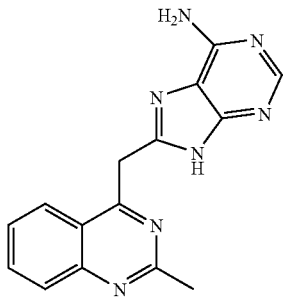

or pharmaceutical salts thereof, the effective concentration being sufficient to inhibit excision of the intein; and b) thereafter enabling excision of the intein by reducing the inhibitor to a level below the effective concentration, the excision thereby activating the function of the protein to a significant degree.

8. The method of claim 7 wherein the intein excision is carried out in vitro.

9. The method of claim 7 wherein the intein excision is carried out in vivo.

10. The method of claim 7 wherein the protein interrupted by the intein is expressed under the control of a tissue-specific promoter.

11. The method of claim 7 wherein the contacting occurs during purification of the protein.

12. The method of claim 7 wherein contacting occurs during synthesis of the protein.

13. The method of claim 7 wherein the protein interrupted by the intein is selected from the group consisting of enzymes, toxins, cytokines, transcription factors, and growth factors.

14. The method of claim 7 wherein excision of the intein renders the protein cytotoxic.

15. The method of claim 7 wherein excision of the intein renders the protein pharmacologically active.

16. A method for controlling the activity of an intein, the method comprising:

a) contacting an intein with its N-terminus or its C-terminus or both being fused to a protein, with a small-molecule inhibitor of protein splicing at an effective concentration, the inhibitor of protein splicing being selected from the group consisting of the compounds of:

Formula 11 (Compound #1)

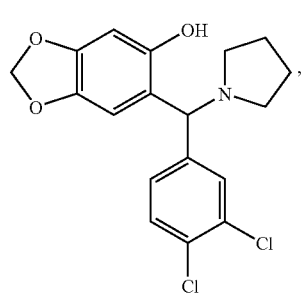

Formula 12 (Compound #2)

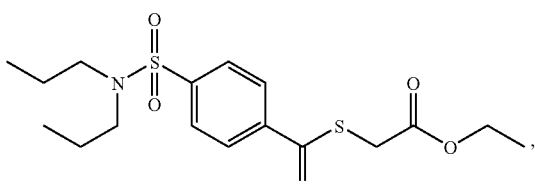

Formula 13 (Compound #3)

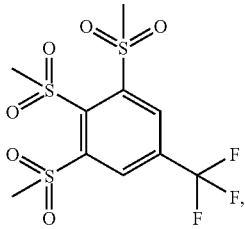

-continued
Formula 14 (Compound #4)
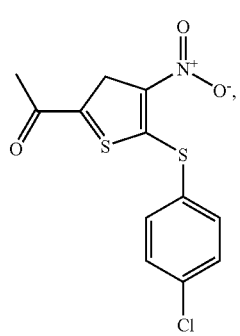
Formula 15 (Compound #6)
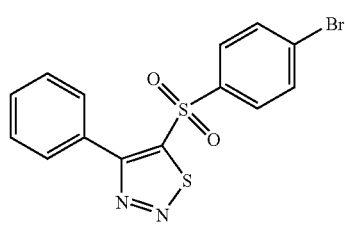
Formula 16 (Compound #7)
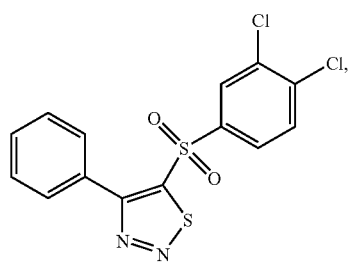
Formula 17 (Compound #8)
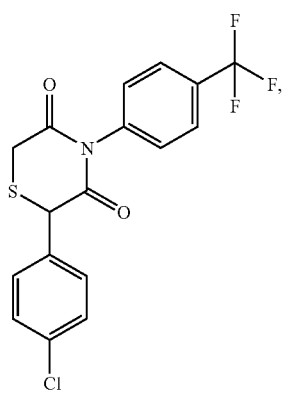
Formula 18 (Compound #9)
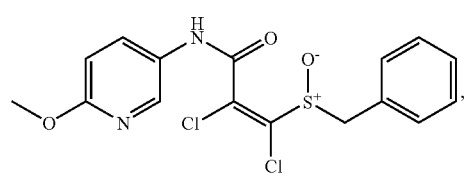
-continued
Formula 19 (Compound #10)
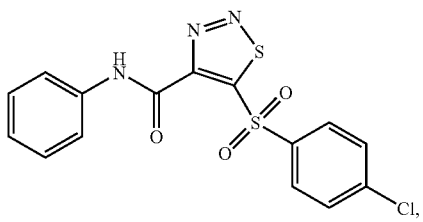
Formula 20 (Compound #11)
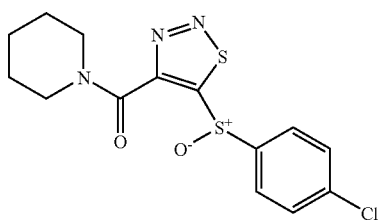
Formula 21 (Compound #12)
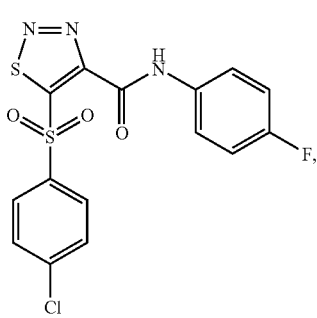
Formula 22 (Compound #13)
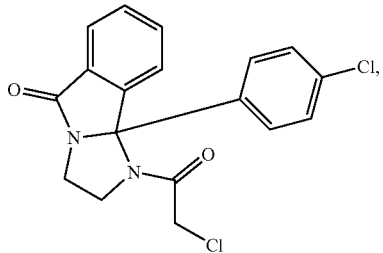
Formula 23 (Compound #17)
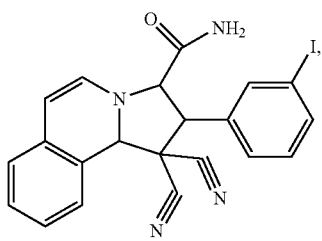
Formula 24 (Compound #21)
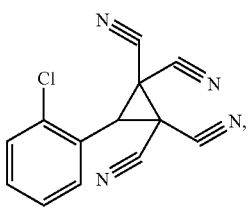

-continued

Formula 25 (Compound #22)

Formula 26 (Compound #23)

Formula 27 (Compound #24)

Formula 28 (Compound #27)

Formula 29 (Compound #29)

Formula 30 (Compound #30)

Formula 31 (Compound #31)

-continued

Formula 32 (Compound #33)

Formula 33 (Compound #35)

Formula 34 (Compound #36)

Formula 35 (Compound #37)

Formula 36 (Compound #38)

-continued
Formula 37 (Compound #39)
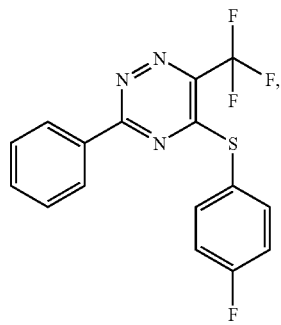
Formula 38 (Compound #40)
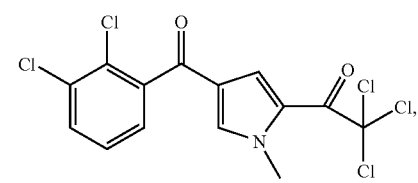
Formula 39 (Compound #41)
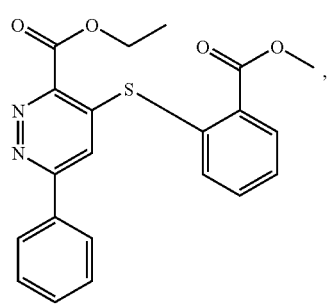
Formula 40 (Compound #43)
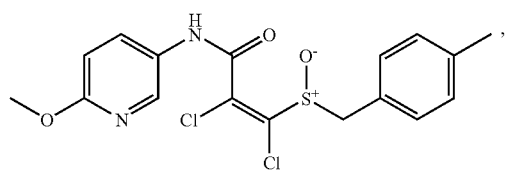
Formula 41 (Compound #44)
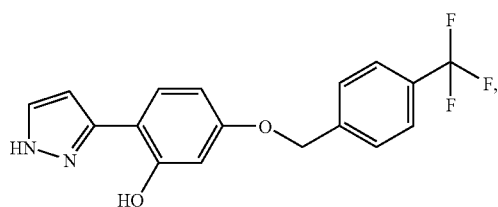
Formula 42 (Compound #45)
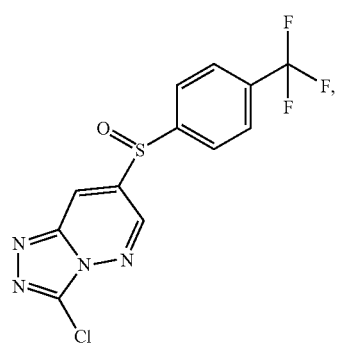
-continued
Formula 43 (Compound #51)
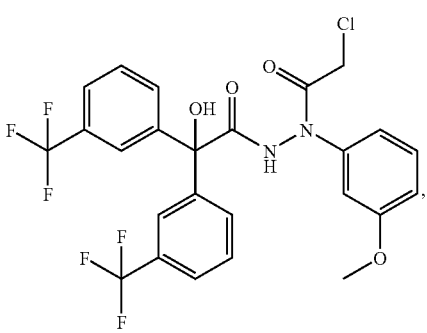
Formula 44 (Compound #53)
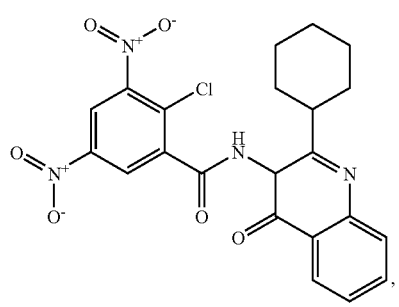
Formula 45 (Compound #54)
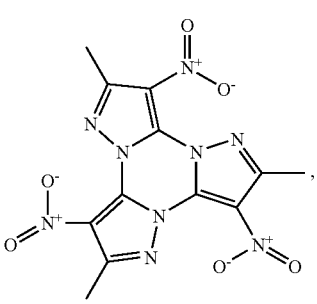
Formula 46 (Compound #55)
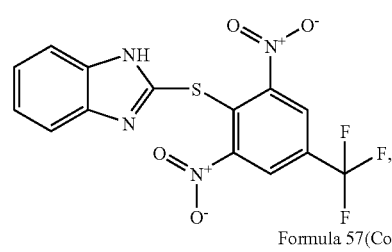
Formula 57 (Compound #56)
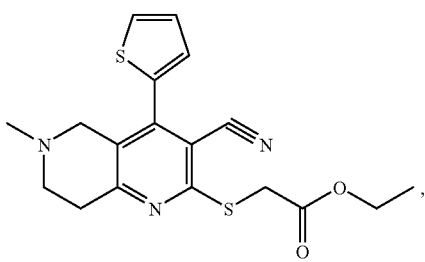

-continued
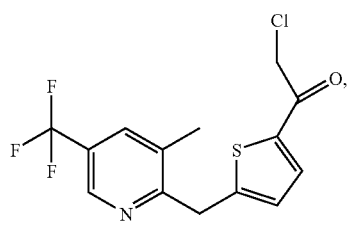
Formula 48 (Compound #57)
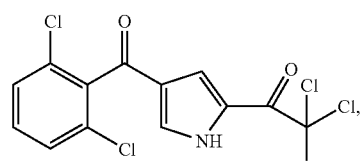
Formula 49 (Compound #58)
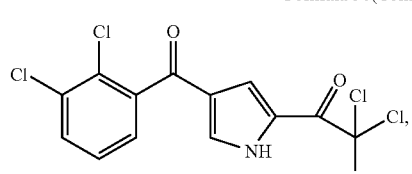
Formula 50 (Compound #59)
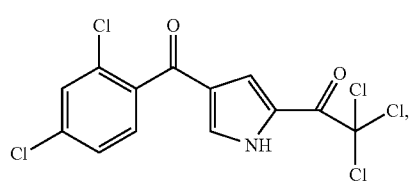
Formula 51 (Compound #62)
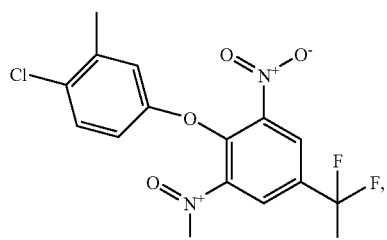
Formula 52 (Compound #64)
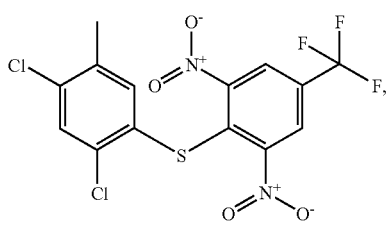
Formula 53 (Compound #65)
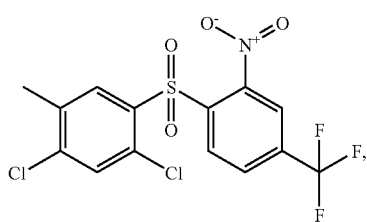
Formula 54 (Compound #66)
-continued
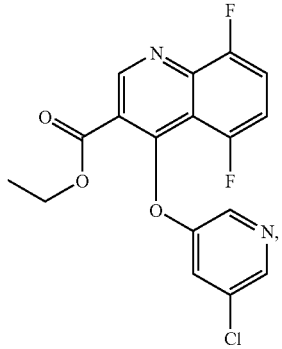
Formula 55 (Compound #67)
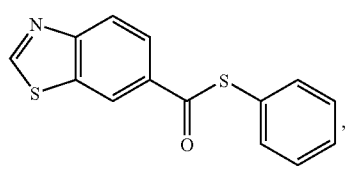
Formula 56 (Compound #68)
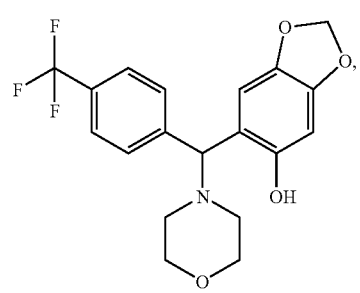
Formula 57 (Compound #69)
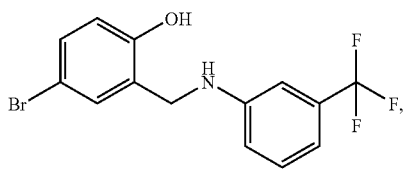
Formula 58 (Compound #70)
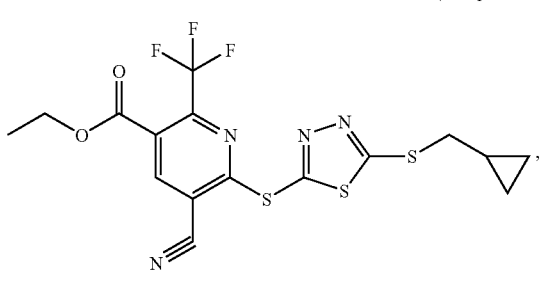
Formula 59 (Compound #71)
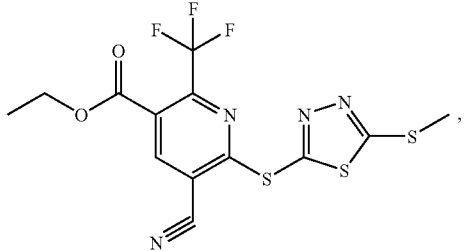
Formula 60 (Compound #72)

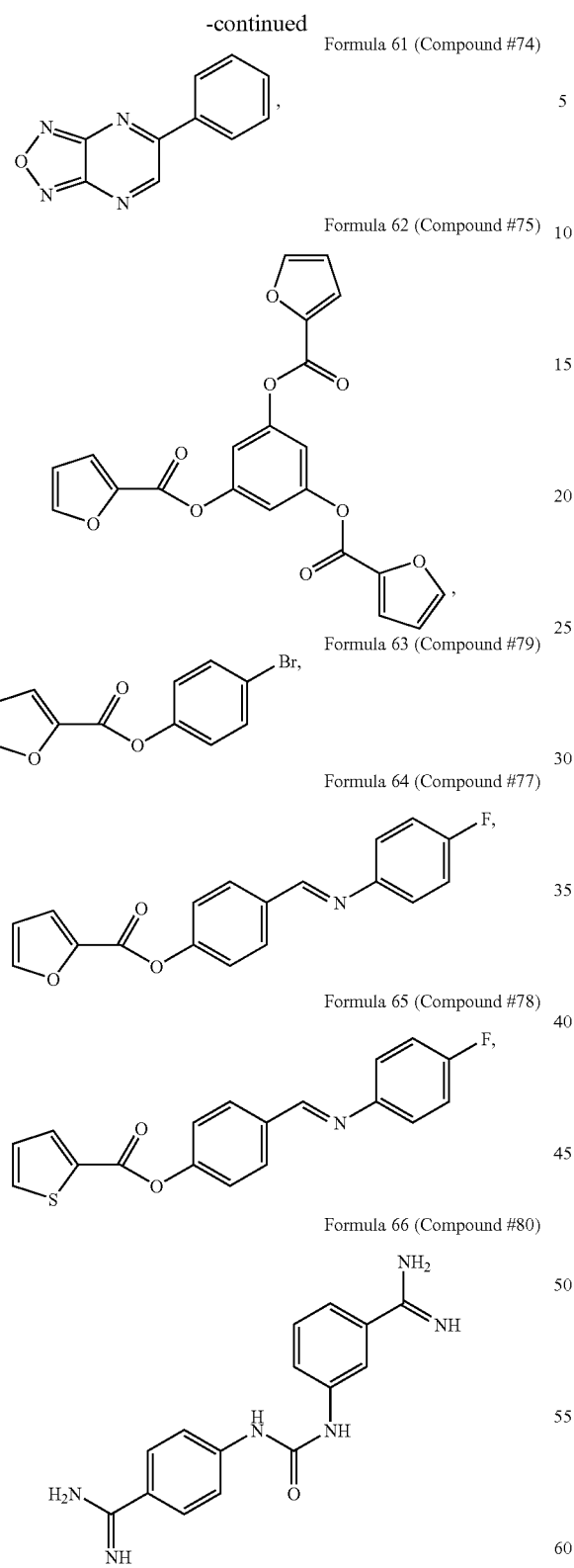
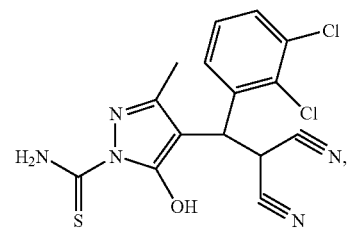
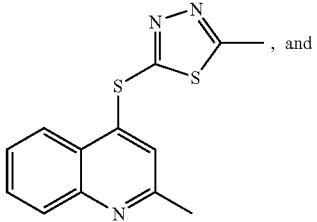
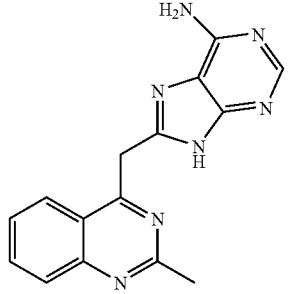

or pharmaceutical salts thereof, the effective concentration being sufficient to inhibit activity of the intein; and b) thereafter enabling cleavage of the intein at its N-terminus or its C-terminus or both by reducing the inhibitor to a level below the effective concentration, thereby controlling the activity of the intein.

17. The method of claim 16 wherein the intein cleavage is carried out in vitro.

18. The method of claim 16 wherein the intein cleavage is carried out in vivo.

19. The method of claim 16 wherein the intein interrupts a protein expressed under the control of a tissue-specific promoter.

20. The method of claim 16 wherein the contacting occurs during purification of the protein.

21. The method of claim 16 wherein the contacting occurs during synthesis of the protein.

* * * * *

UNITED STATES PATENT AND TRADEMARK OFFICE
CERTIFICATE OF CORRECTION

| | | |
|---|---|---|
| PATENT NO. | : 7,553,832 B2 | |
| APPLICATION NO. | : 11/338383 | |
| DATED | : June 30, 2009 | |
| INVENTOR(S) | : Paulus | |

It is certified that error appears in the above-identified patent and that said Letters Patent is hereby corrected as shown below:

Delete column 23 lines 1 through column 54 line 59 and insert column 23 lines 1 through column 59 line 59 as attached Signed and Sealed this
First Day of March, 2011

David J. Kappos
*Director of the United States Patent and Trademark Office*

The invention claimed is:

1. A method for inhibiting protein splicing, the method comprising contacting an intein-containing protein with one or more small-molecule inhibitors of protein splicing, the inhibitors being organic compounds which interact specifically with the intein-containing protein and wherein the inhibitors are selected from the group consisting of:

Formula 11 (Compound #1)

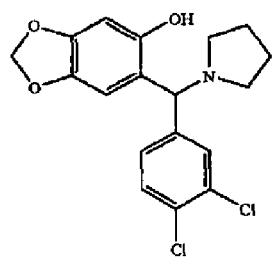

Formula 12 (Compound #2)

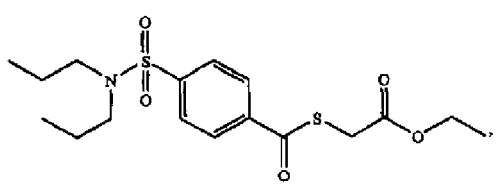

Formula 13 (Compound #3)

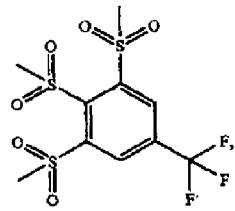

Formula 14 (Compound #4)

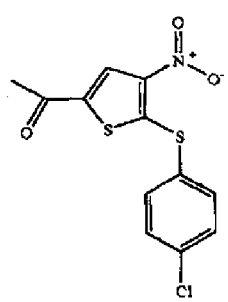

Formula 15 (Compound #6)

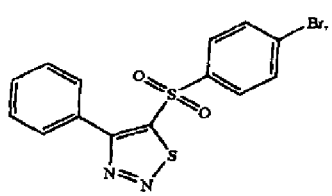

-continued

Formula 16 (Compound #7)

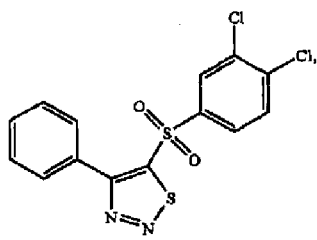

Formula 17 (Compound #8)

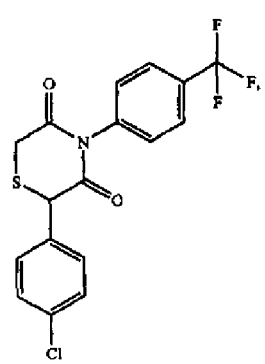

Formula 18 (Compound #9)

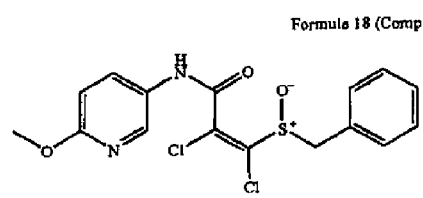

Formula 19 (Compound #10)

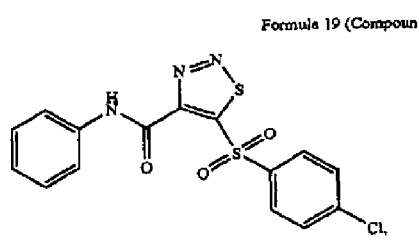

Formula 20 (Compound #11)

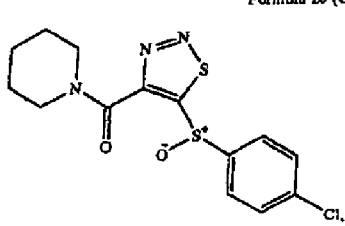

25
-continued
Formula 21 (Compound #12)
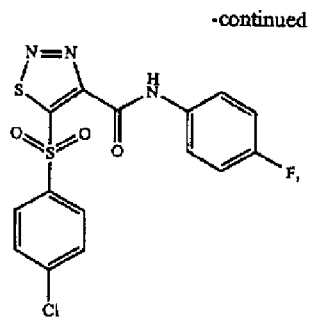
Formula 22 (Compound #13)
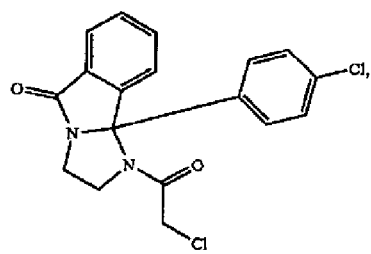
Formula 23 (Compound #17)
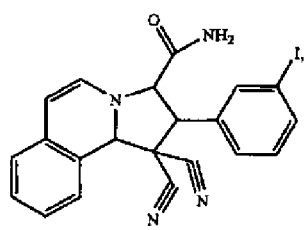
Formula 24 (Compound #21)
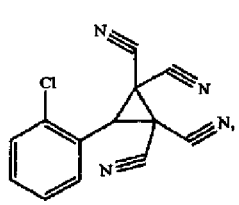
Formula 25 (Compound #22)
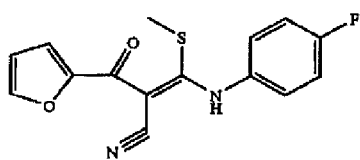
Formula 26 (Compound #23)
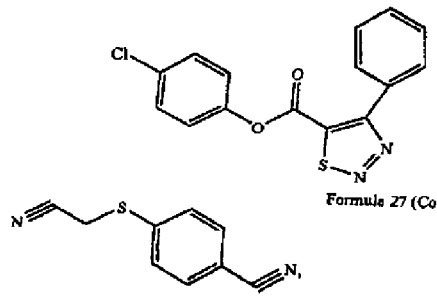
Formula 27 (Compound #24)
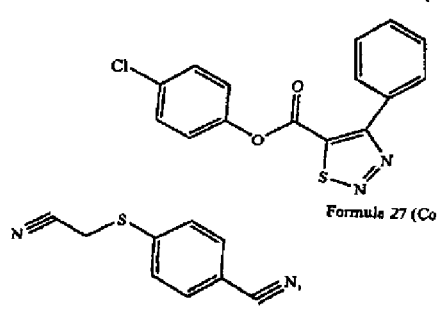
26
-continued
Formula 28 (Compound #27)
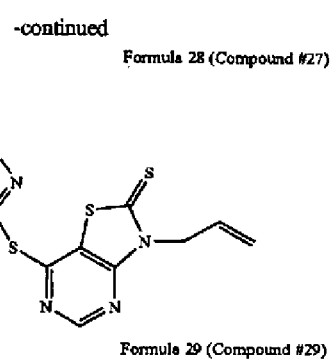
Formula 29 (Compound #29)
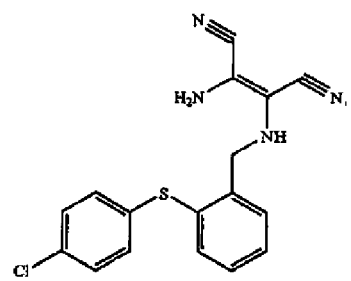
Formula 30 (Compound #30)
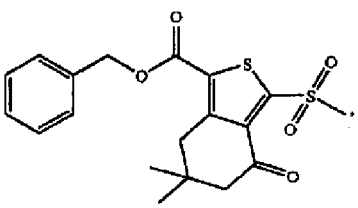
Formula 31 (Compound #31)
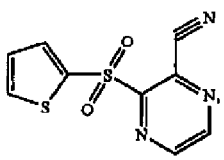
Formula 32 (Compound #33)
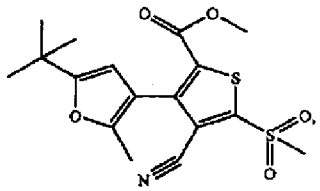
Formula 33 (Compound #35)
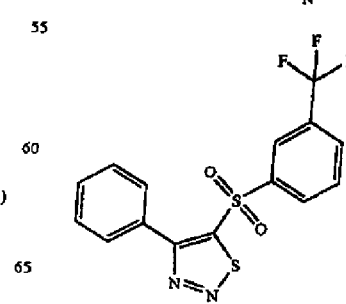

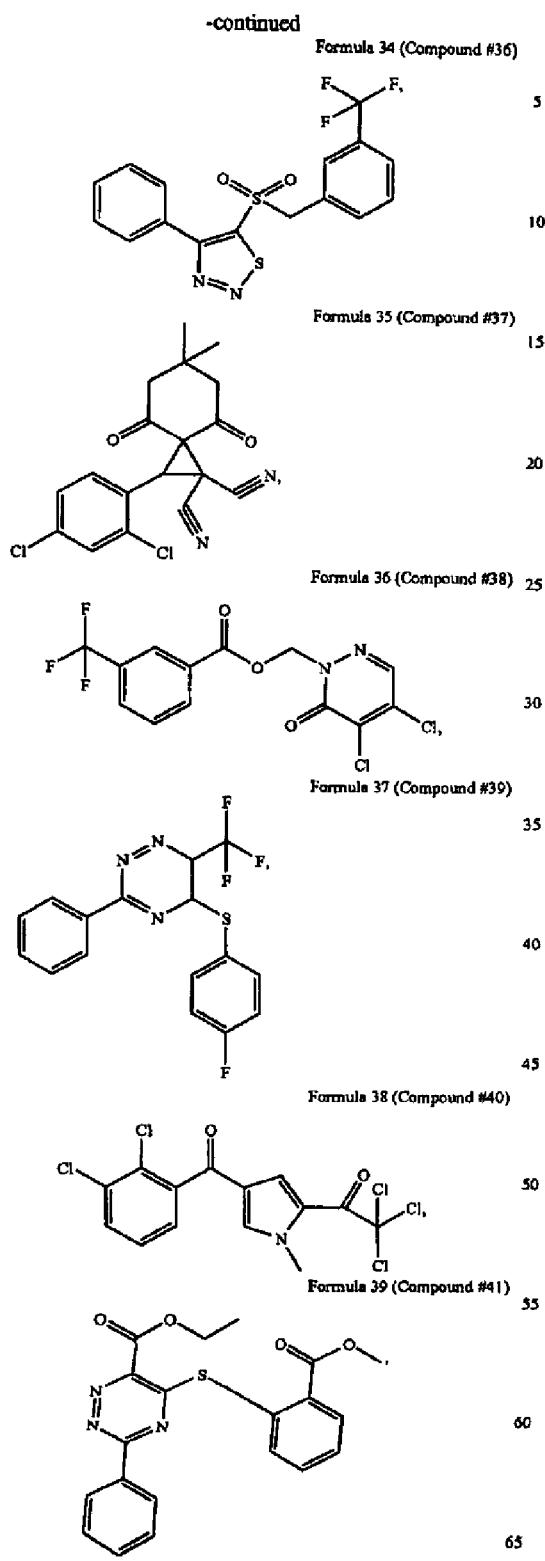

-continued
Formula 45 (Compound #54)
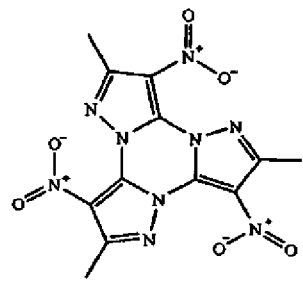
Formula 46 (Compound #55)
Formula 47 (Compound #56)
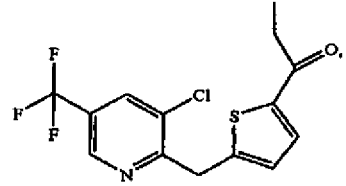
Formula 48 (Compound #57)
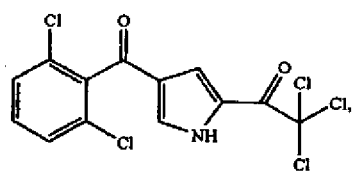
Formula 49 (Compound #58)
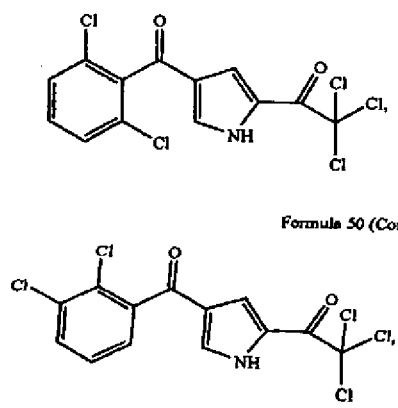
Formula 50 (Compound #59)
-continued
Formula 51 (Compound #62)
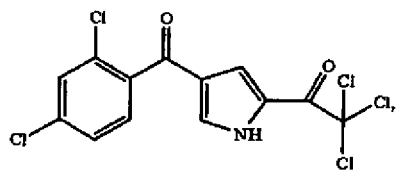
Formula 52 (Compound #64)
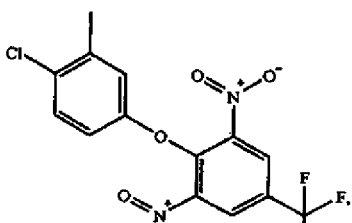
Formula 53 (Compound #65)
Formula 54 (Compound #66)
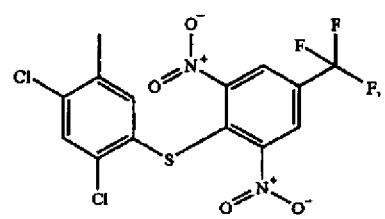
Formula 55 (Compound #67)
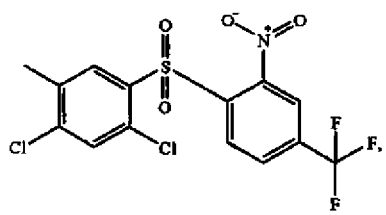
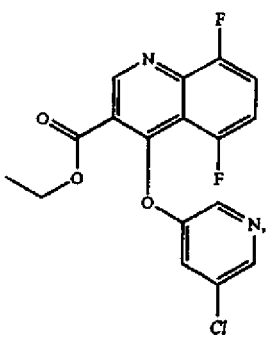
Formula 56 (Compound #68)
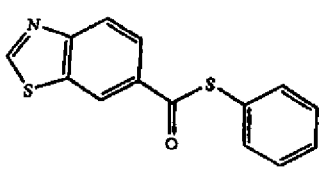

-continued
Formula 57 (Compound #69)
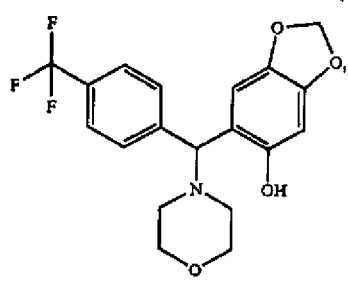
Formula 58 (Compound #70)
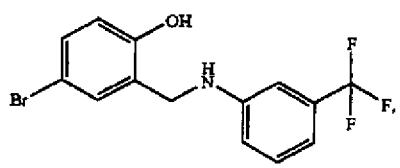
Formula 59 (Compound #71)
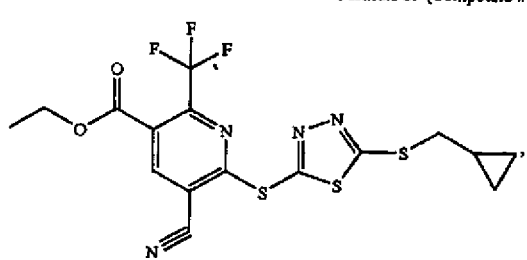
Formula 60 (Compound #72)
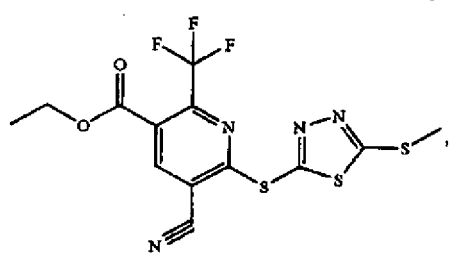
Formula 61 (Compound #74)
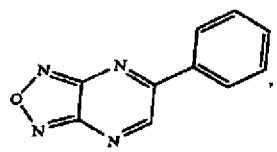
-continued
Formula 62 (Compound #75)
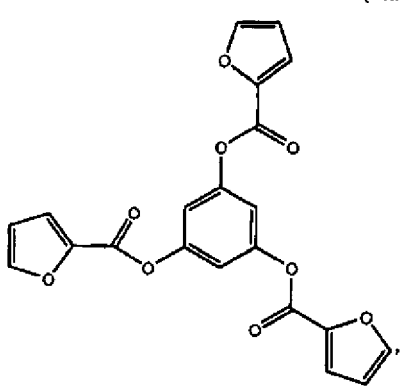
Formula 63 (Compound #76)
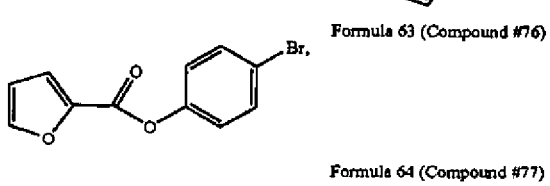
Formula 64 (Compound #77)
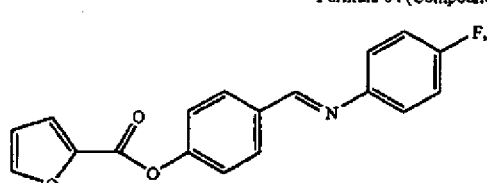
Formula 65 (Compound #78)
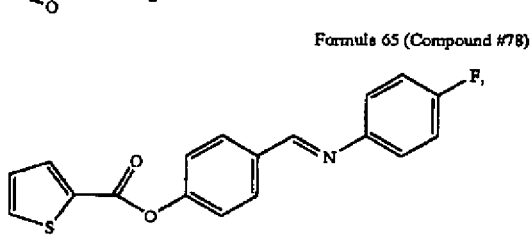
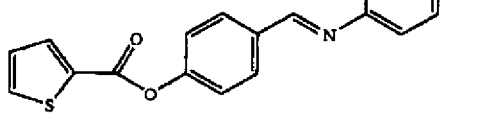
Formula 66 (Compound #80)
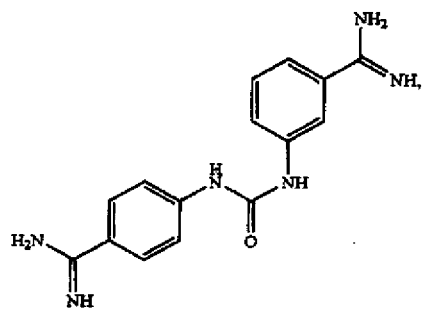
Formula 67 (Compound #81)
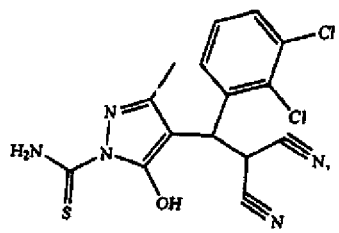

-continued

Formula 68 (Compound #82)

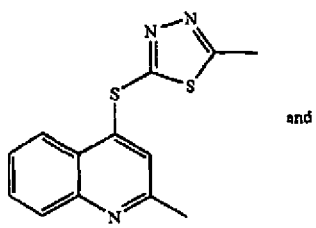

and

Formula 69 (Compound #83)

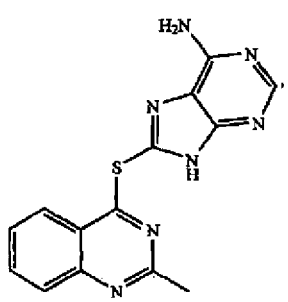

or pharmaceutical salts thereof.

2. The method of claim 1 wherein the contacting step is carried out in vitro.
3. The method of claim 1 wherein the contacting step is carried out in vivo.
4. The method of claim 1 wherein the protein containing the intein is selected from the group consisting of enzymes, toxins, cytokines, transcription factors, and growth factors.
5. The method of claim 1 wherein the contacting occurs during purification of the protein.
6. The method of claim 1 wherein the contacting occurs during synthesis of the protein.
7. A method for activating the function of a protein, the method comprising:
   a) contacting a protein which is interrupted by an intein wherein the intein renders the protein inactive, with a small-molecule inhibitor of protein splicing at an effective concentration, the inhibitor of protein splicing being selected from the group consisting of the compounds of:

Formula 11 (Compound #1)

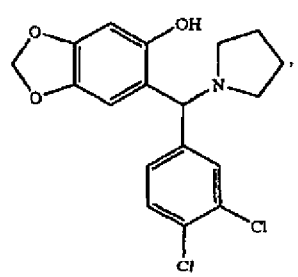

Formula 12 (Compound #2)

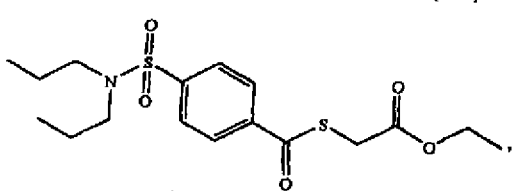

-continued

Formula 13 (Compound #3)

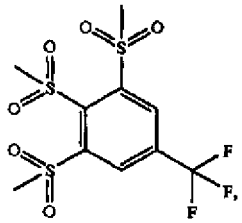

Formula 14 (Compound #4)

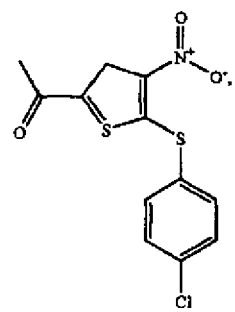

Formula 15 (Compound #6)

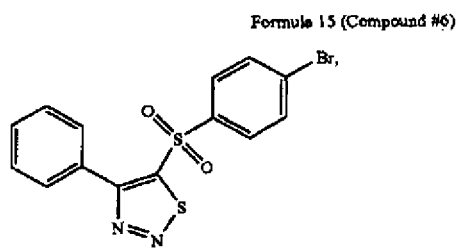

Formula 16 (Compound #7)

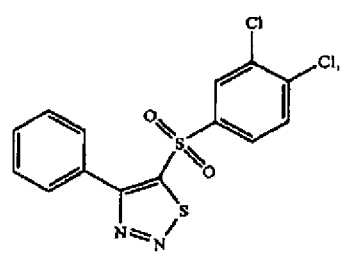

Formula 17 (Compound #8)

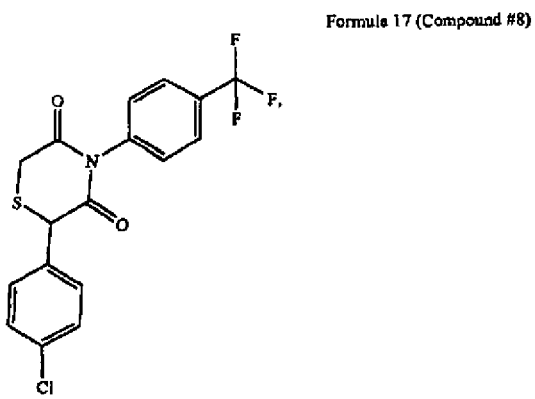

-continued
Formula 18 (Compound #9)
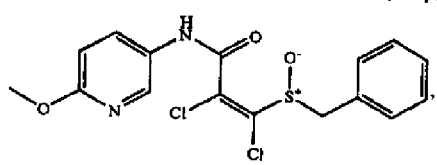
Formula 19 (Compound #10)
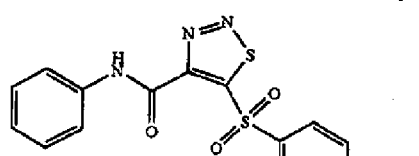
Formula 20 (Compound #11)
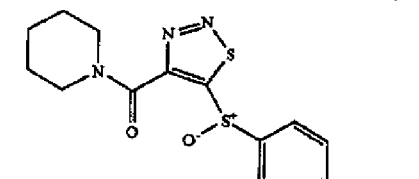
Formula 21 (Compound #12)
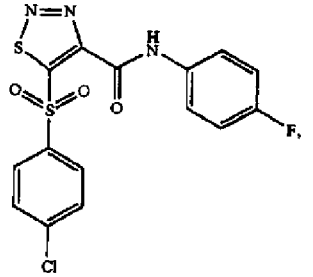
Formula 22 (Compound #13)
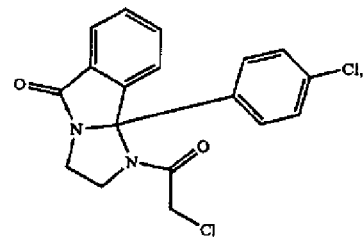
Formula 23 (Compound #17)
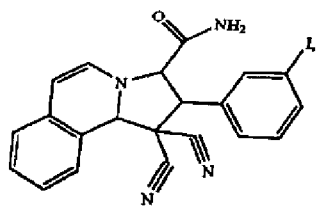
-continued
Formula 24 (Compound #21)
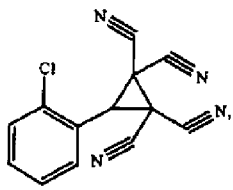
Formula 25 (Compound #22)
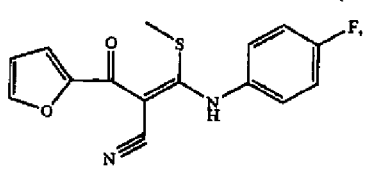
Formula 26 (Compound #23)
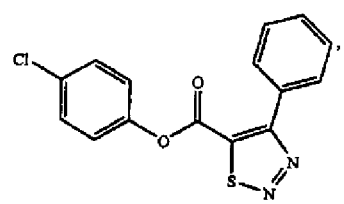
Formula 27 (Compound #24)
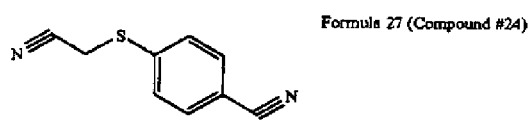
Formula 28 (Compound #27)
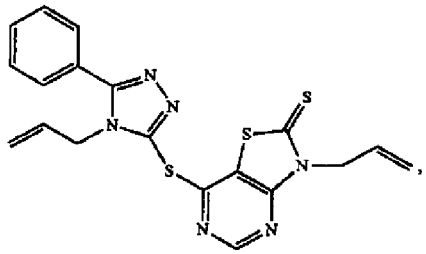
Formula 29 (Compound #29)
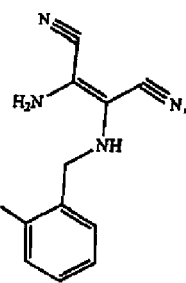

-continued
Formula 30 (Compound #30)
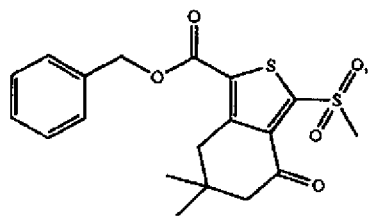
Formula 31 (Compound #31)
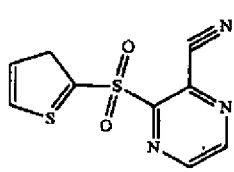
Formula 32 (Compound #33)
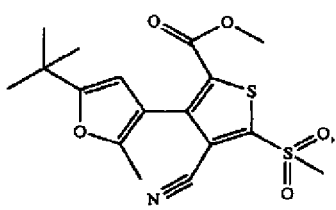
Formula 33 (Compound #35)
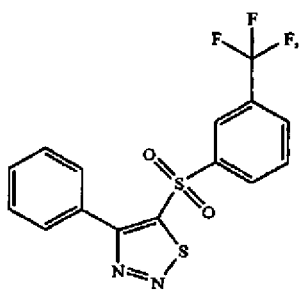
Formula 34 (Compound #36)
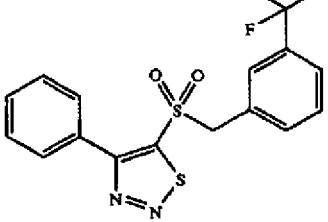
Formula 35 (Compound #37)
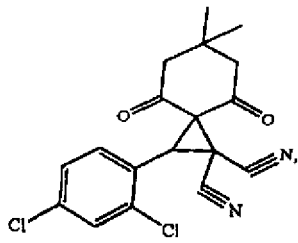
-continued
Formula 36 (Compound #38)
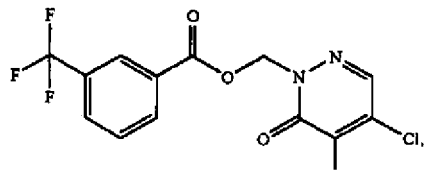
Formula 37 (Compound #39)
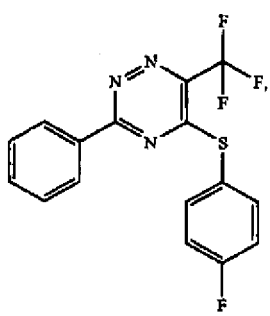
Formula 38 (Compound #40)
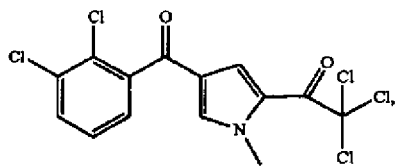
Formula 39 (Compound #41)
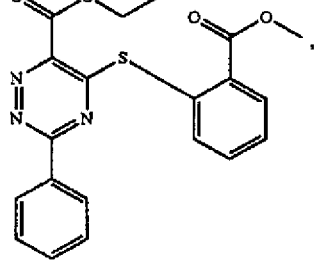
Formula 40 (Compound #43)
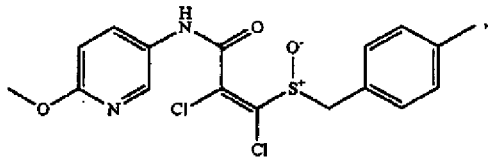
Formula 41 (Compound #44)
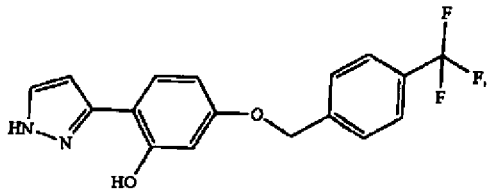

-continued
Formula 42 (Compound #45)
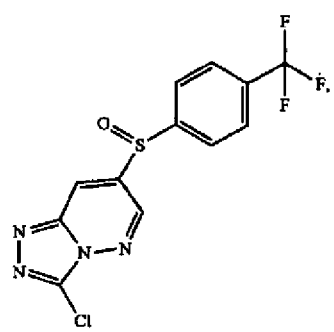
Formula 43 (Compound #51)
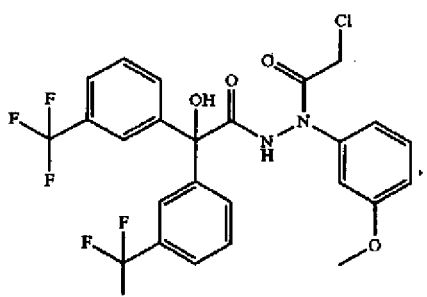
Formula 44 (Compound #53)
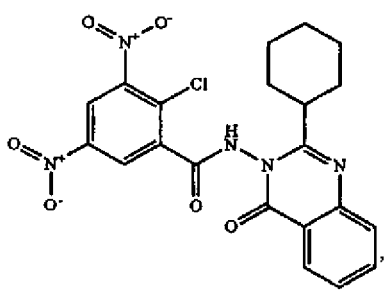
Formula 45 (Compound #54)
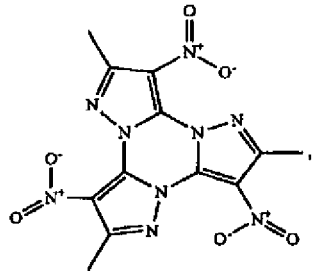
Formula 46 (Compound #55)
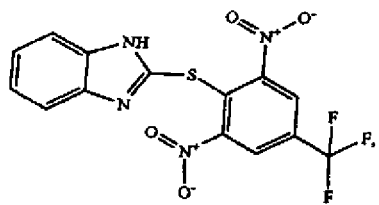
-continued
Formula 47 (Compound #56)
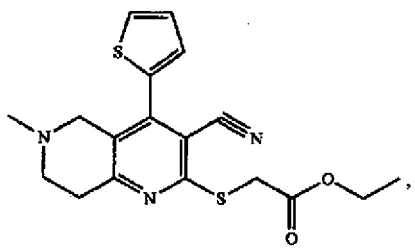
Formula 48 (Compound #57)
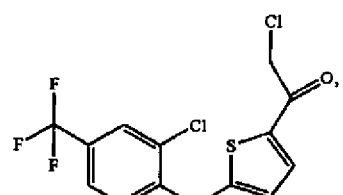
Formula 49 (Compound #58)
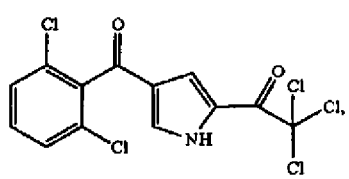
Formula 50 (Compound #59)
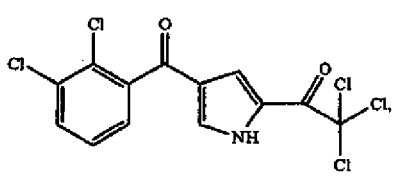
Formula 51 (Compound #62)
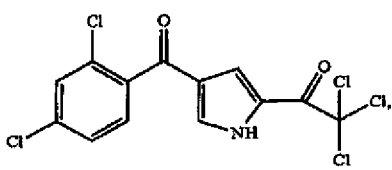
Formula 52 (Compound #64)
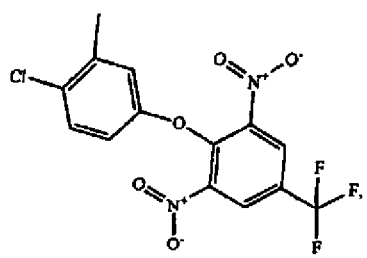

-continued
Formula 53 (Compound #65)
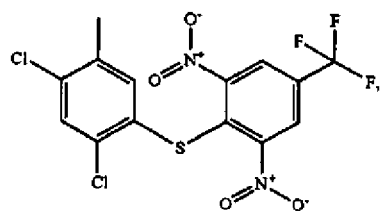
Formula 54 (Compound #66)
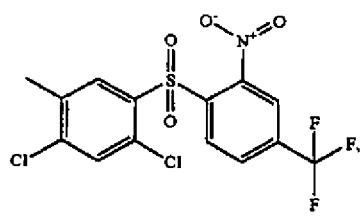
Formula 55 (Compound #67)
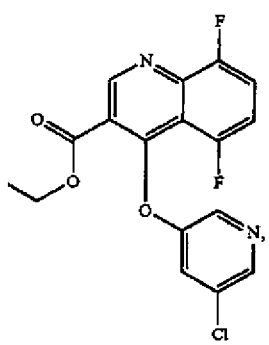
Formula 56 (Compound #68)
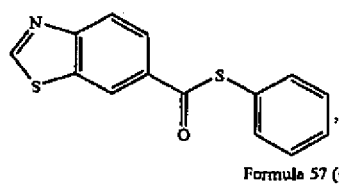
Formula 57 (Compound #69)
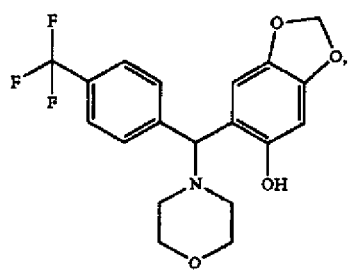
Formula 58 (Compound #70)
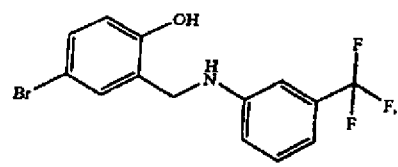
-continued
Formula 59 (Compound #71)
Formula 60 (Compound #72)
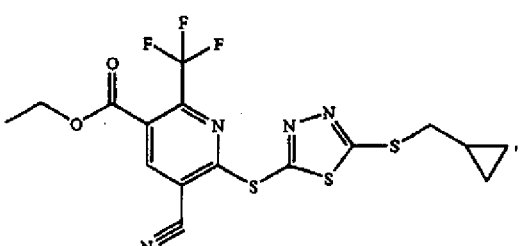
Formula 61 (Compound #74)
Formula 62 (Compound #75)
Formula 63 (Compound #79)
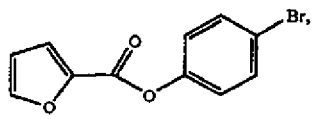
Formula 64 (Compound #77)
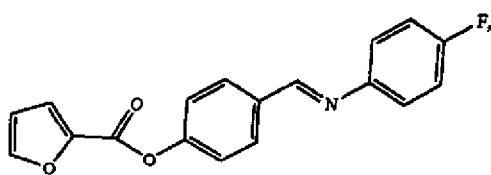

-continued

Formula 65 (Compound #78)
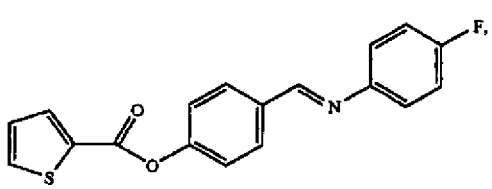

Formula 66 (Compound #80)
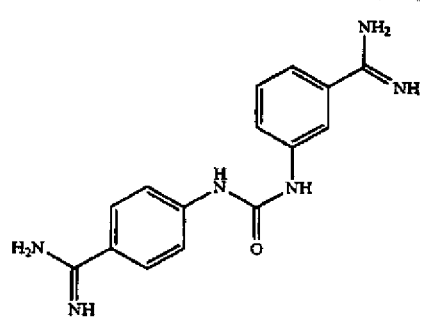

Formula 67 (Compound #81)
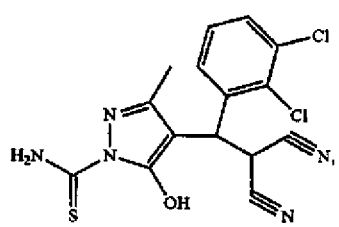

Formula 68 (Compound #82)
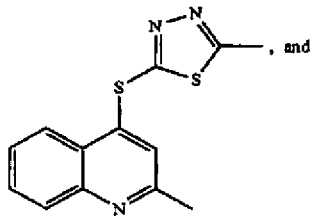, and

Formula 69 (Compound #83)
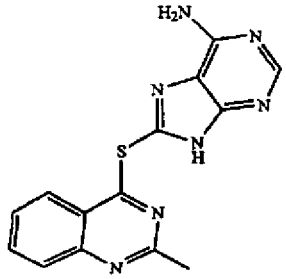

or pharmaceutical salts thereof, the effective concentration being sufficient to inhibit excision of the intein; and b) thereafter enabling excision of the intein by reducing the inhibitor to a level below the effective concentration, the excision thereby activating the function of the protein to a significant degree.

8. The method of claim 7 wherein the intein excision is carried out in vitro.

9. The method of claim 7 wherein the intein excision is carried out in vivo.

10. The method of claim 7 wherein the protein interrupted by the intein is expressed under the control of a tissue-specific promoter.

11. The method of claim 7 wherein the contacting occurs during purification of the protein.

12. The method of claim 7 wherein contacting occurs during synthesis of the protein.

13. The method of claim 7 wherein the protein interrupted by the intein is selected from the group consisting of enzymes, toxins, cytokines, transcription factors, and growth factors.

14. The method of claim 7 wherein excision of the intein renders the protein cytotoxic.

15. The method of claim 7 wherein excision of the intein renders the protein pharmacologically active.

16. A method for controlling the activity of an intein, the method comprising:

a) contacting an intein with its N-terminus or its C-terminus or both being fused to a protein, with a small-molecule inhibitor of protein splicing at an effective concentration, the inhibitor of protein splicing being selected from the group consisting of the compounds of:

Formula 11 (Compound #1)
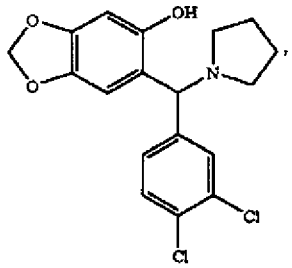

Formula 12 (Compound #2)
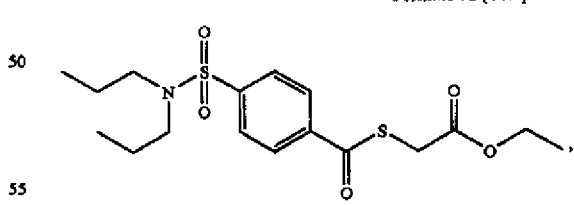

Formula 13 (Compound #3)
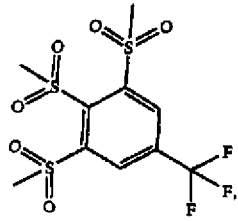

-continued
Formula 14 (Compound #4)
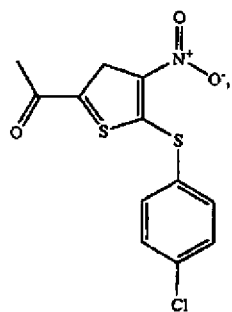
Formula 15 (Compound #6)
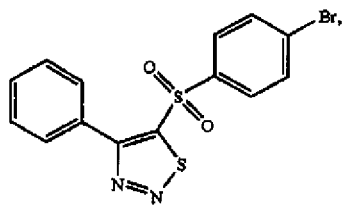
Formula 16 (Compound #7)
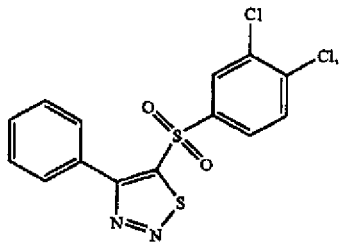
Formula 17 (Compound #8)
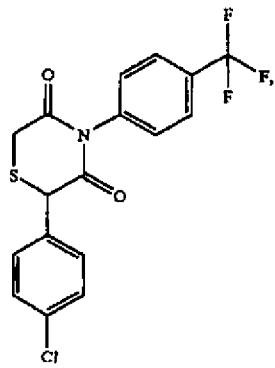
Formula 18 (Compound #9)
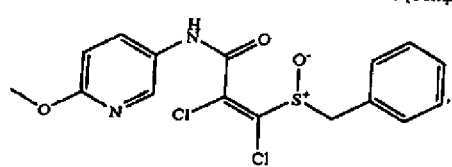
-continued
Formula 19 (Compound #10)
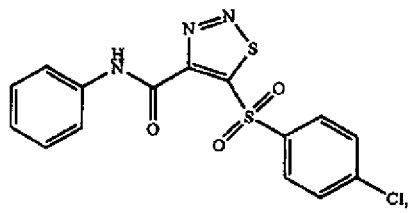
Formula 20 (Compound #11)
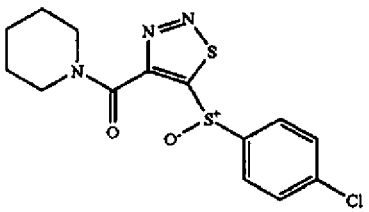
Formula 21 (Compound #12)
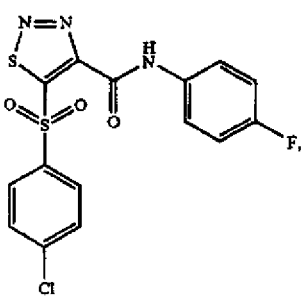
Formula 22 (Compound #13)
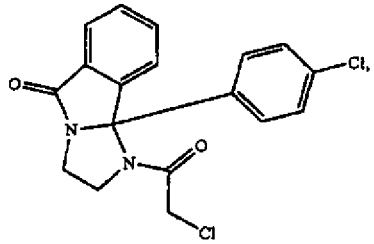
Formula 23 (Compound #17)
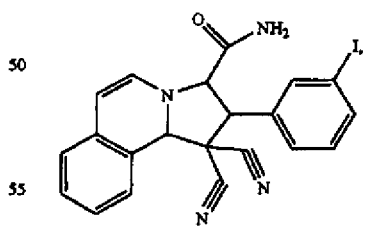
Formula 24 (Compound #21)
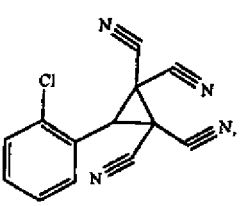

47
-continued
Formula 25 (Compound #22)
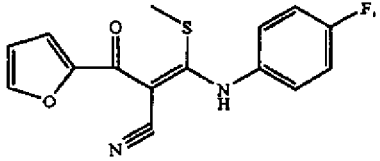
Formula 26 (Compound #23)
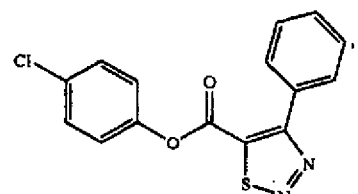
Formula 27 (Compound #24)
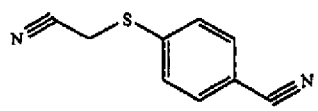
Formula 28 (Compound #27)
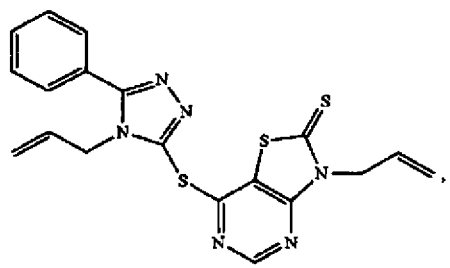
Formula 29 (Compound #29)
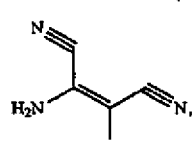
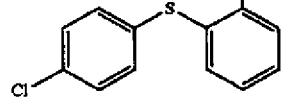
Formula 30 (Compound #30)
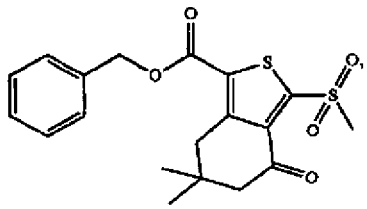
Formula 31 (Compound #31)
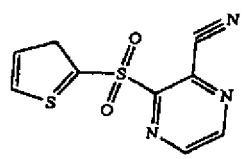
48
-continued
Formula 32 (Compound #33)
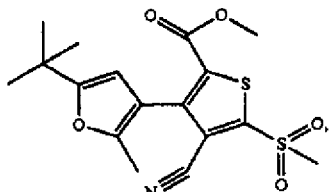
Formula 33 (Compound #35)
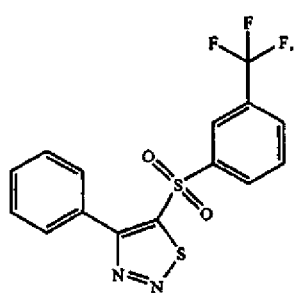
Formula 34 (Compound #36)
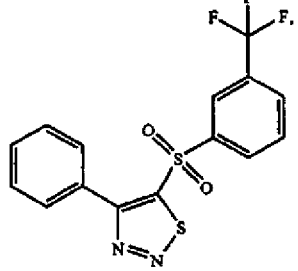
Formula 35 (Compound #37)
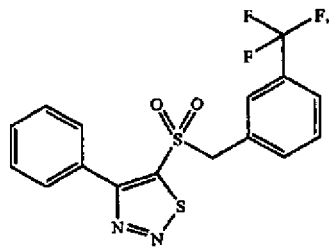
Formula 36 (Compound #38)
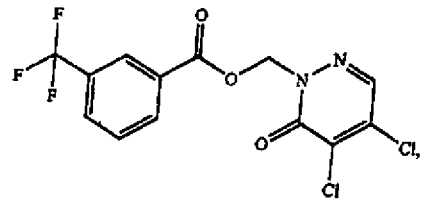

-continued

Formula 37 (Compound #39)

Formula 38 (Compound #40)

Formula 39 (Compound #41)

Formula 40 (Compound #43)

Formula 41 (Compound #44)

Formula 42 (Compound #45)

-continued

Formula 43 (Compound #51)

Formula 44 (Compound #53)

Formula 45 (Compound #54)

Formula 46 (Compound #55)

Formula 47 (Compound #56)

-continued
Formula 48 (Compound #57)
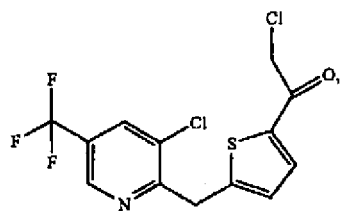
Formula 49 (Compound #58)
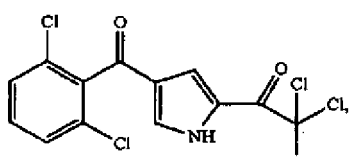
Formula 50 (Compound #59)
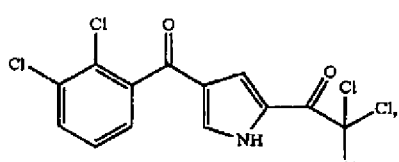
Formula 51 (Compound #62)
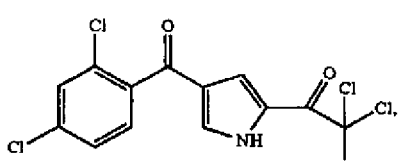
Formula 52 (Compound #64)
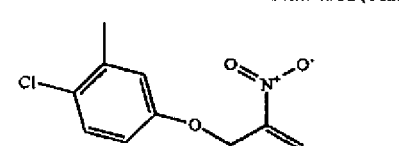
Formula 53 (Compound #65)
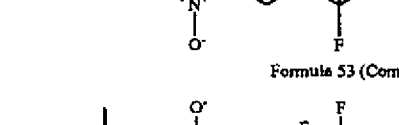
Formula 54 (Compound #66)
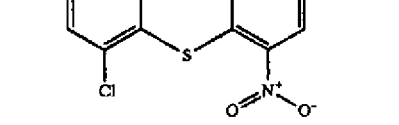
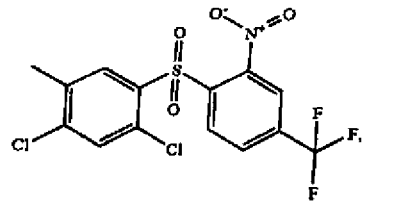
-continued
Formula 55 (Compound #67)
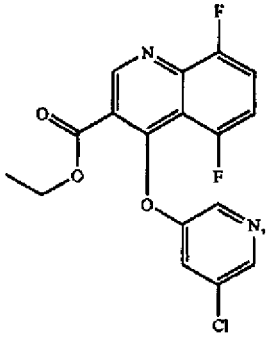
Formula 56 (Compound #68)
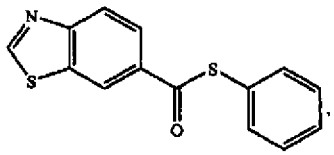
Formula 57 (Compound #69)
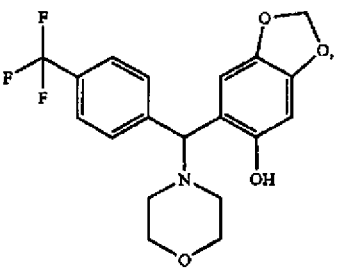
Formula 58 (Compound #70)
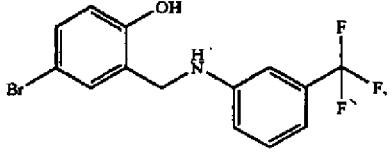
Formula 59 (Compound #71)
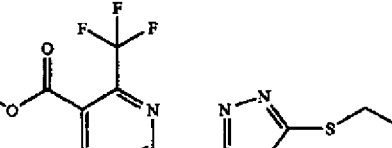
Formula 60 (Compound #72)
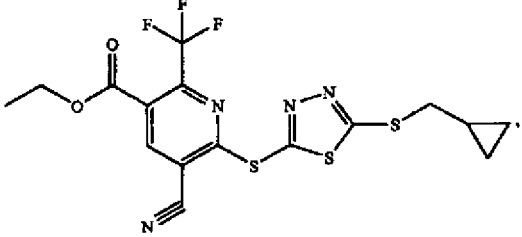
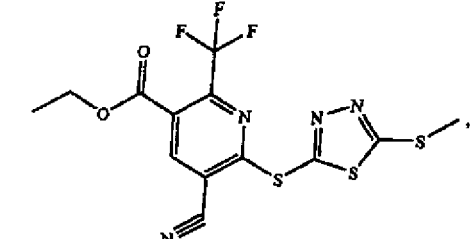

53

-continued

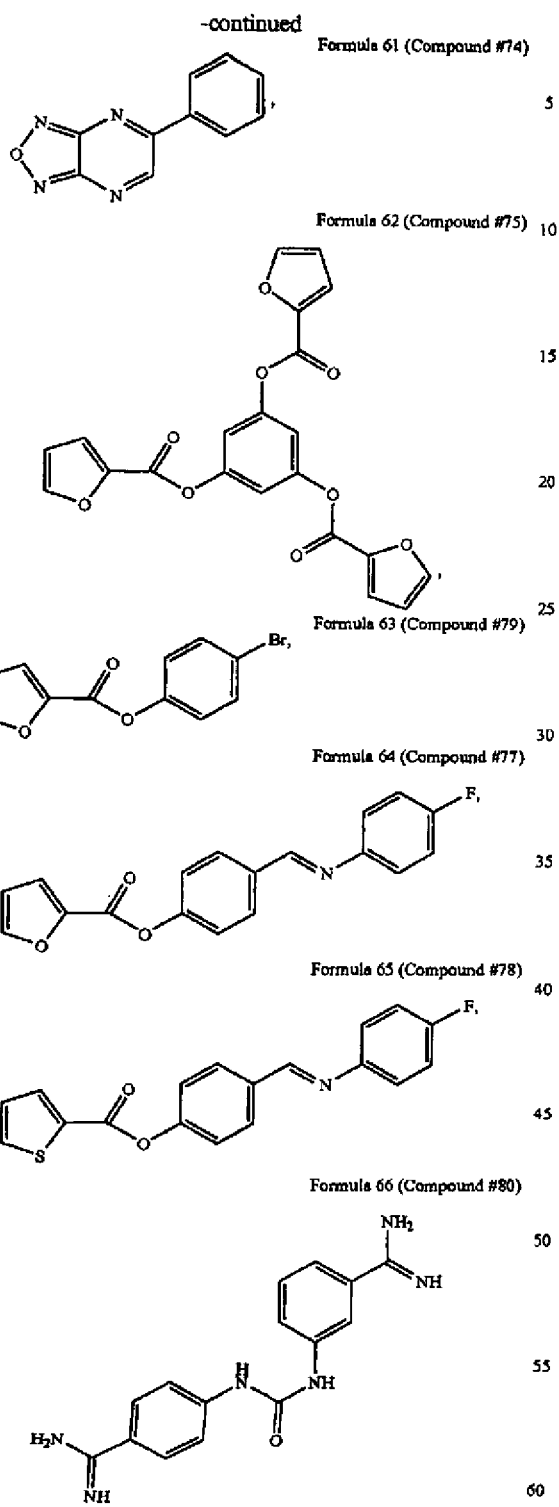

54

-continued

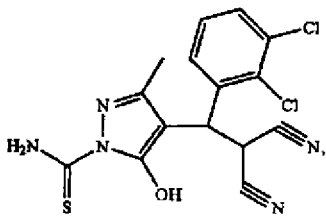

Formula 67 (Compound #81)

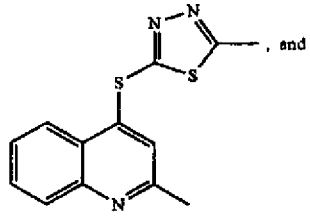

Formula 68 (Compound #82), and

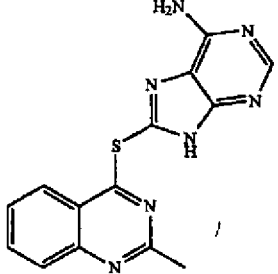

Formula 69 (Compound #83)

or pharmaceutical salts thereof, the effective concentration being sufficient to inhibit activity of the intein; and b) thereafter enabling cleavage of the intein at its N-terminus or its C-terminus or both by reducing the inhibitor to a level below the effective concentration, thereby controlling the activity of the intein.

17. The method of claim 16 wherein the intein cleavage is carried out in vitro.

18. The method of claim 16 wherein the intein cleavage is carried out in vivo.

19. The method of claim 16 wherein the intein interrupts a protein expressed under the control of a tissue-specific promoter.

20. The method of claim 16 wherein the contacting occurs during purification of the protein.

21. The method of claim 16 wherein the contacting occurs during synthesis of the protein.

* * * * *